US009498593B2

(12) United States Patent
Karpas et al.

(10) Patent No.: US 9,498,593 B2
(45) Date of Patent: Nov. 22, 2016

(54) CUSTOMIZED MEDICAL DEVICES AND APPAREL

(71) Applicant: MetaMason, Inc., Pasadena, CA (US)

(72) Inventors: Leslie Oliver Karpas, Pasadena, CA (US); Robert William Moore, Sandhurst (GB)

(73) Assignee: MetaMason, Inc., Los Angeles, CA (US)

( * ) Notice: Subject to any disclaimer, the term of this patent is extended or adjusted under 35 U.S.C. 154(b) by 117 days.

(21) Appl. No.: 14/102,370

(22) Filed: Dec. 10, 2013

(65) Prior Publication Data

US 2015/0157822 A1    Jun. 11, 2015

Related U.S. Application Data

(60) Provisional application No. 61/861,376, filed on Aug. 1, 2013, provisional application No. 61/828,618, filed on Jun. 17, 2013.

(51) Int. Cl.

| | |
|---|---|
| *G06F 19/00* | (2011.01) |
| *A61M 16/06* | (2006.01) |
| *B29C 67/00* | (2006.01) |
| *B29C 33/52* | (2006.01) |
| *G06F 17/50* | (2006.01) |
| *B33Y 10/00* | (2015.01) |
| *B29K 101/12* | (2006.01) |

(52) U.S. Cl.
CPC .......... *A61M 16/0605* (2014.02); *B29C 33/52* (2013.01); *B29C 67/0055* (2013.01); *B29C 67/0092* (2013.01); *B33Y 10/00* (2014.12); *G06F 17/50* (2013.01); *A61M 2016/0661* (2013.01); *A61M 2207/00* (2013.01); *B29K 2101/12* (2013.01); *B29K 2995/0059* (2013.01); *B29K 2995/0062* (2013.01)

(58) Field of Classification Search
CPC ................. A61M 16/0605; A61M 2016/0661; G06F 17/50; B33Y 10/00; B29C 67/0092
USPC ........................... 700/118, 98, 163; 703/1, 6
See application file for complete search history.

(56) References Cited

U.S. PATENT DOCUMENTS

| | | |
|---|---|---|
| 6,728,589 B1 | 4/2004 | Delache |
| 7,904,193 B2 | 3/2011 | Janbakhsh |

(Continued)

FOREIGN PATENT DOCUMENTS

| | | |
|---|---|---|
| WO | WO 2005/106087 A1 | 11/2005 |
| WO | WO 2013/088293 A1 | 6/2013 |

*Primary Examiner* — Kristen Matter
(74) *Attorney, Agent, or Firm* — KPPB LLP

(57) ABSTRACT

Systems and methods for making a custom sleep apnea mask or other wearable article are disclosed. The sleep apnea system comprises a face mask, a headband integrally connected to the face mask, and at least one air duct configured to direct air from the CPAP machine to nasal tubes. The face mask preferably comprises: an inner surface having the same shape as the user's face; an upper surface configured to sit at a first predetermined distance between the user's nose and eyes; and an outer surface configured to extend a second predetermined distance from the inner surface. Nearly shape and position of substantially all the surfaces of the mask are configured based on the shape and or location of facial features, resulting in a highly customized mask optimized for each individual patient.

5 Claims, 59 Drawing Sheets

(56) References Cited

U.S. PATENT DOCUMENTS

| | | | |
|---|---|---|---|
| 8,005,651 B2 | 8/2011 | Summit | |
| 8,254,637 B2 | 8/2012 | Abourizk | |
| 2004/0079374 A1* | 4/2004 | Thornton | A61M 16/06 128/206.21 |
| 2006/0023228 A1 | 2/2006 | Geng | |
| 2007/0244670 A1* | 10/2007 | Sakaguchi | A41H 3/007 703/1 |
| 2008/0006273 A1 | 1/2008 | Thornton | |
| 2008/0060652 A1* | 3/2008 | Selvarajan | A61M 16/06 128/206.21 |
| 2009/0065005 A1* | 3/2009 | Ades | A61M 16/06 128/205.25 |
| 2012/0305003 A1 | 12/2012 | Mark | |

\* cited by examiner

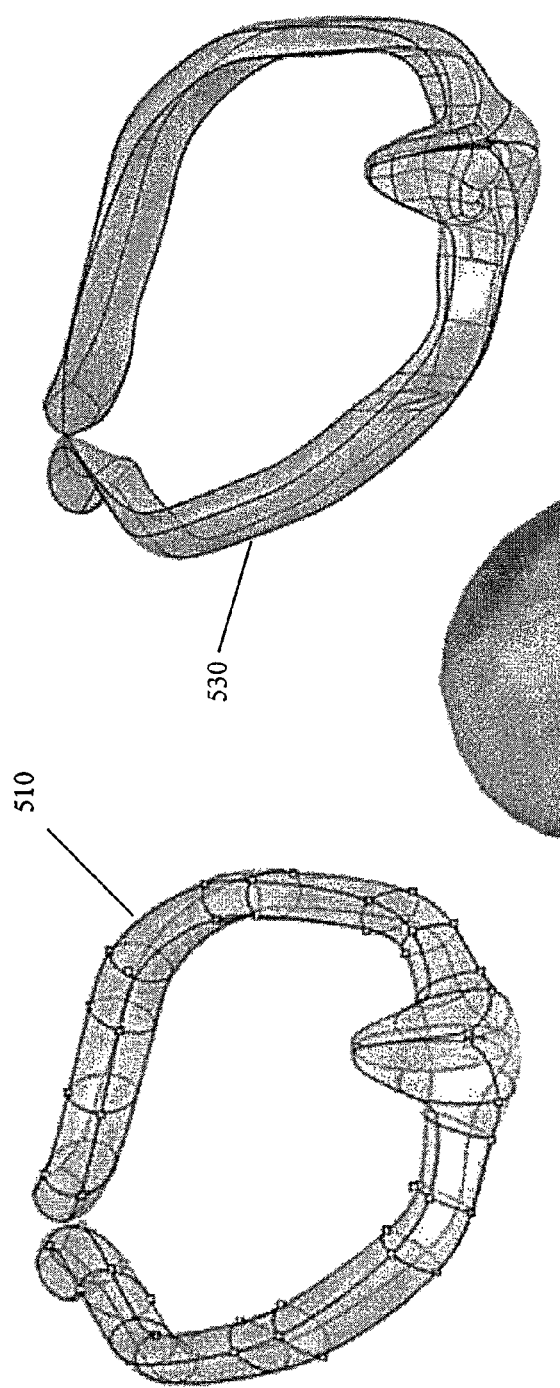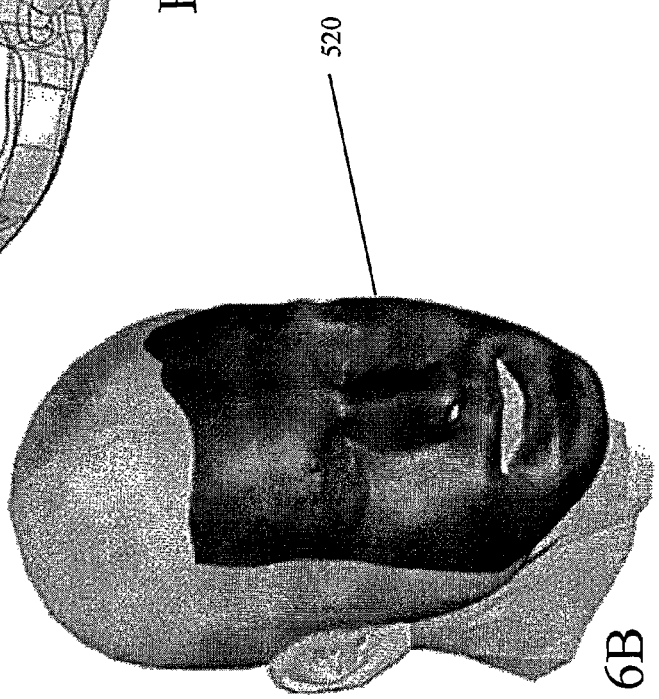
FIG. 6A
FIG. 6B
FIG. 6C

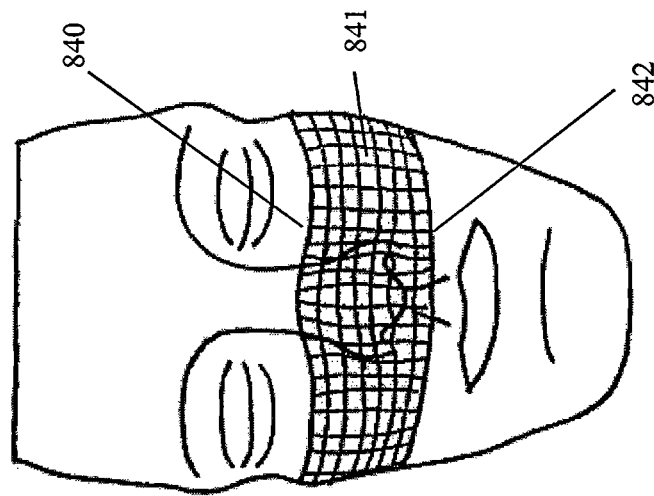
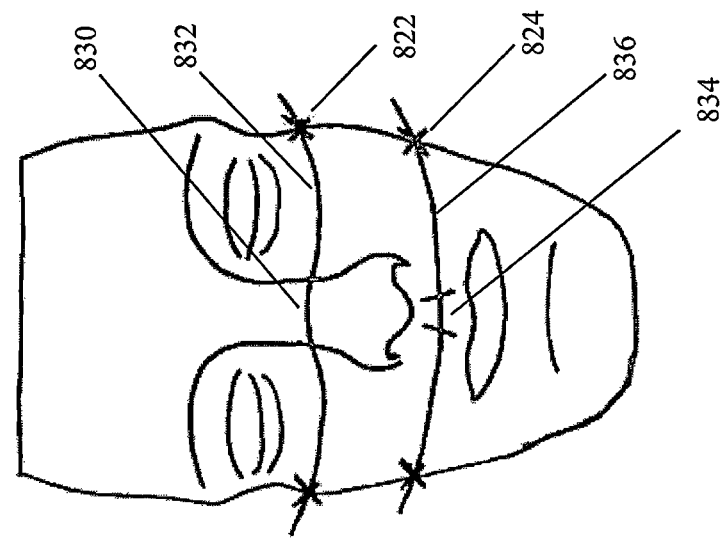
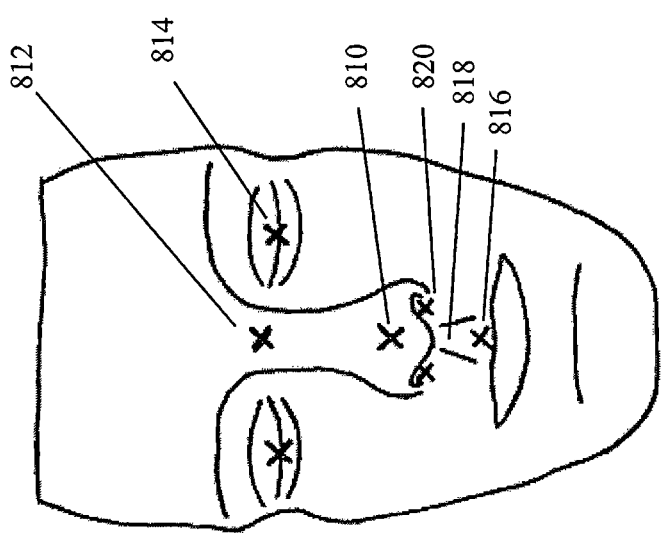
FIG. 8C
FIG. 8B
FIG. 8A

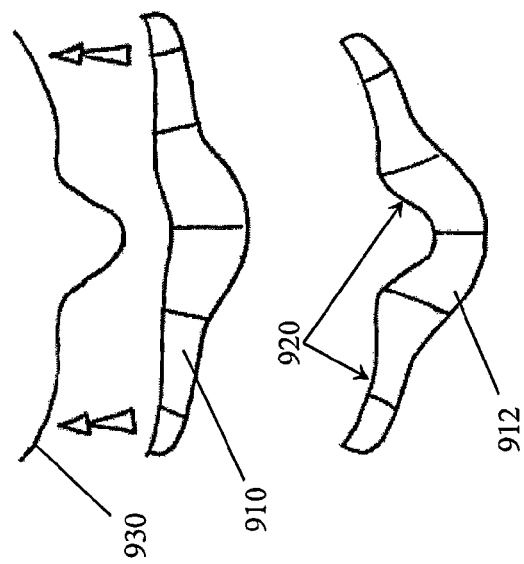
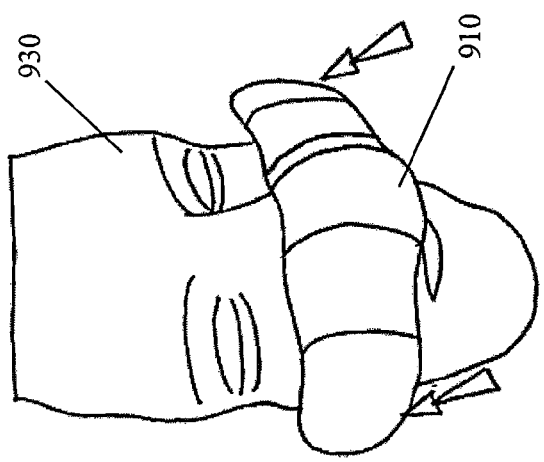
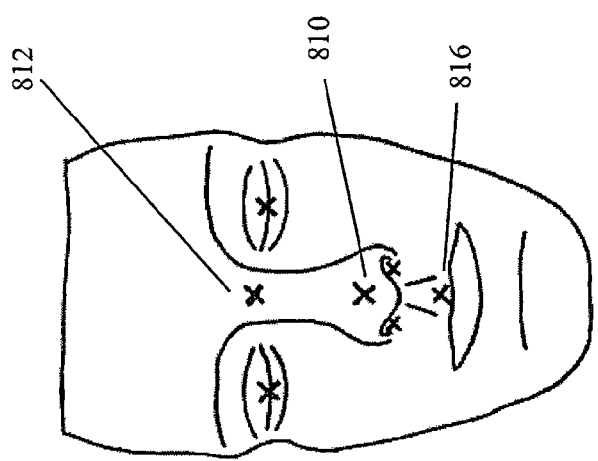
FIG. 9C  FIG. 9D  FIG. 9B  FIG. 9A

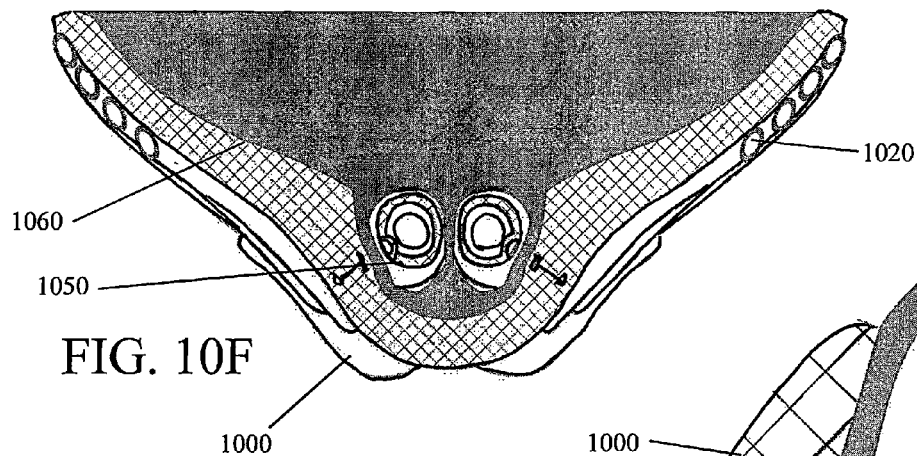
FIG. 10F
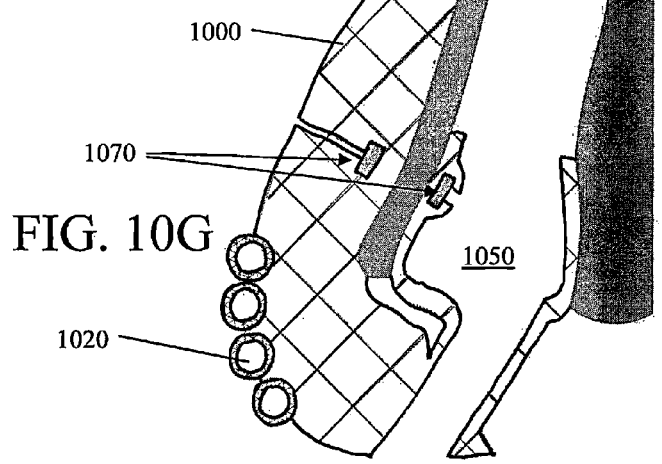
FIG. 10G
FIG. 10H
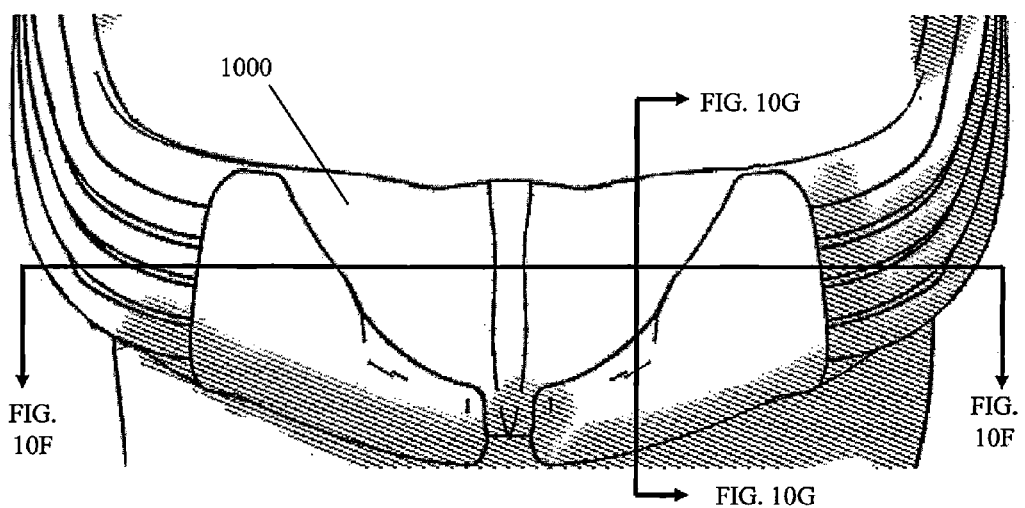

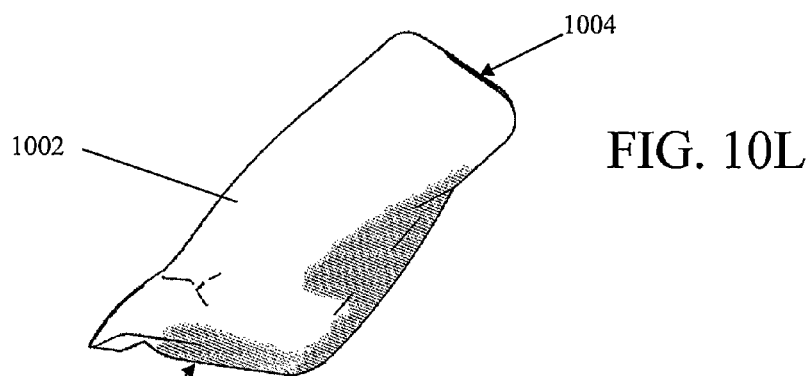
FIG. 10L
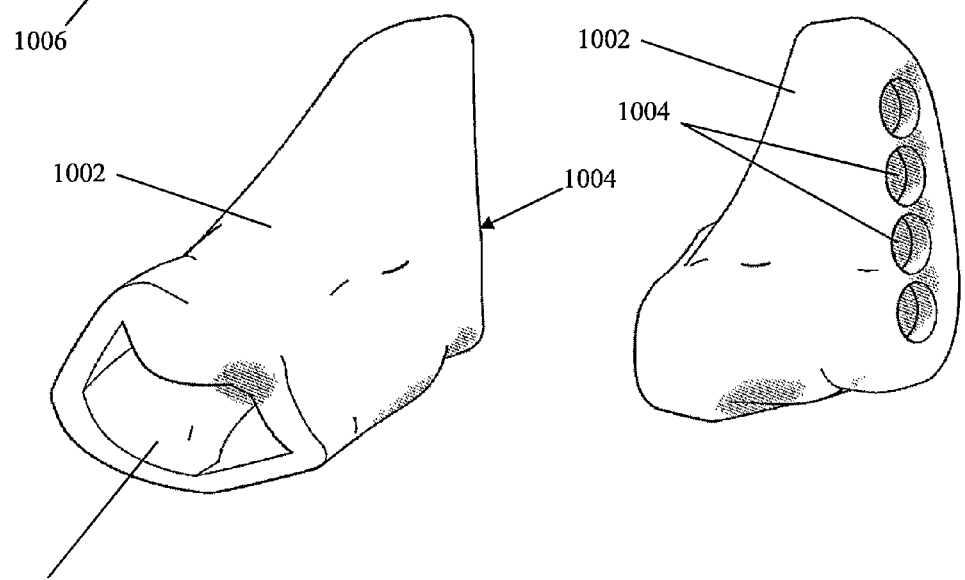
FIG. 10M
FIG. 10N

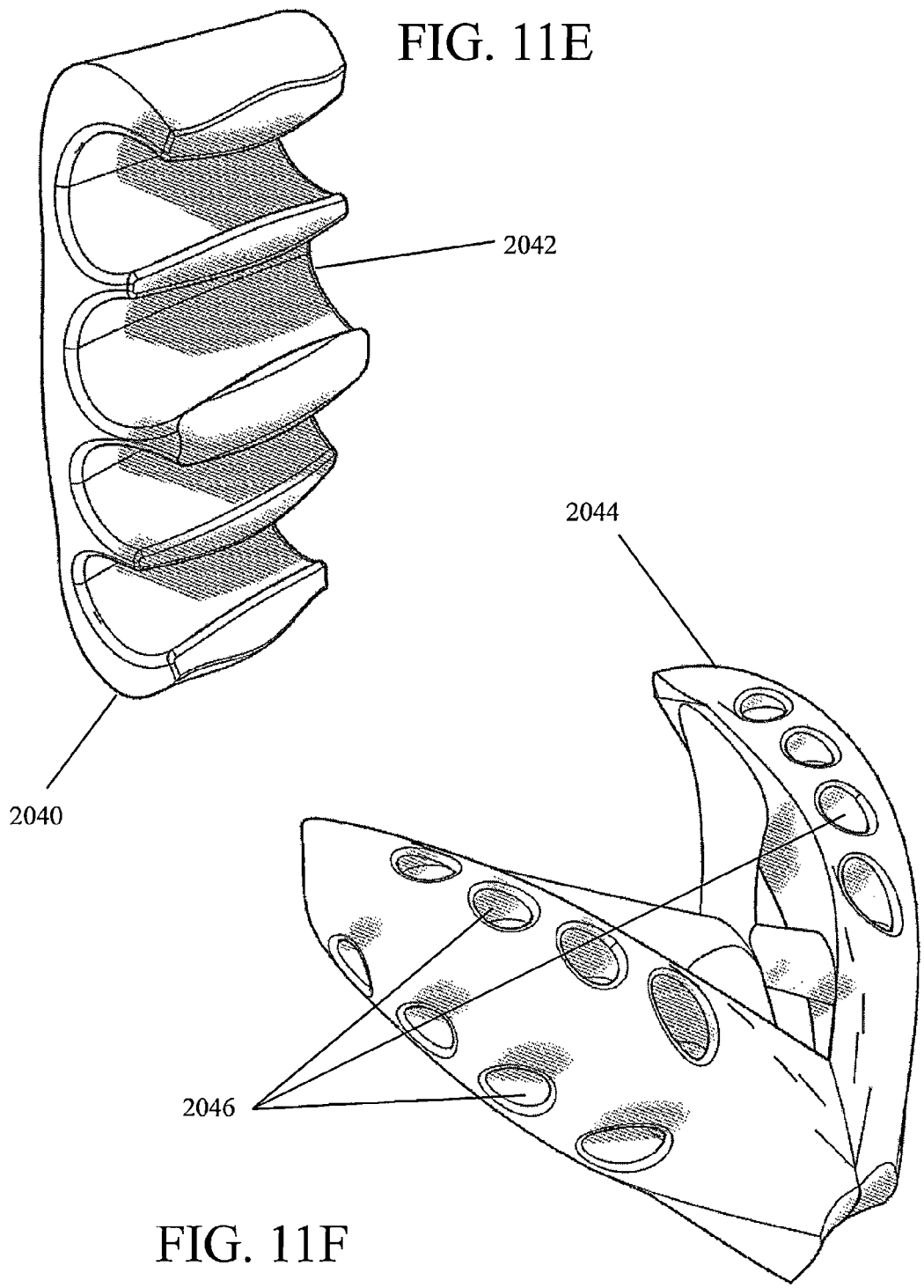

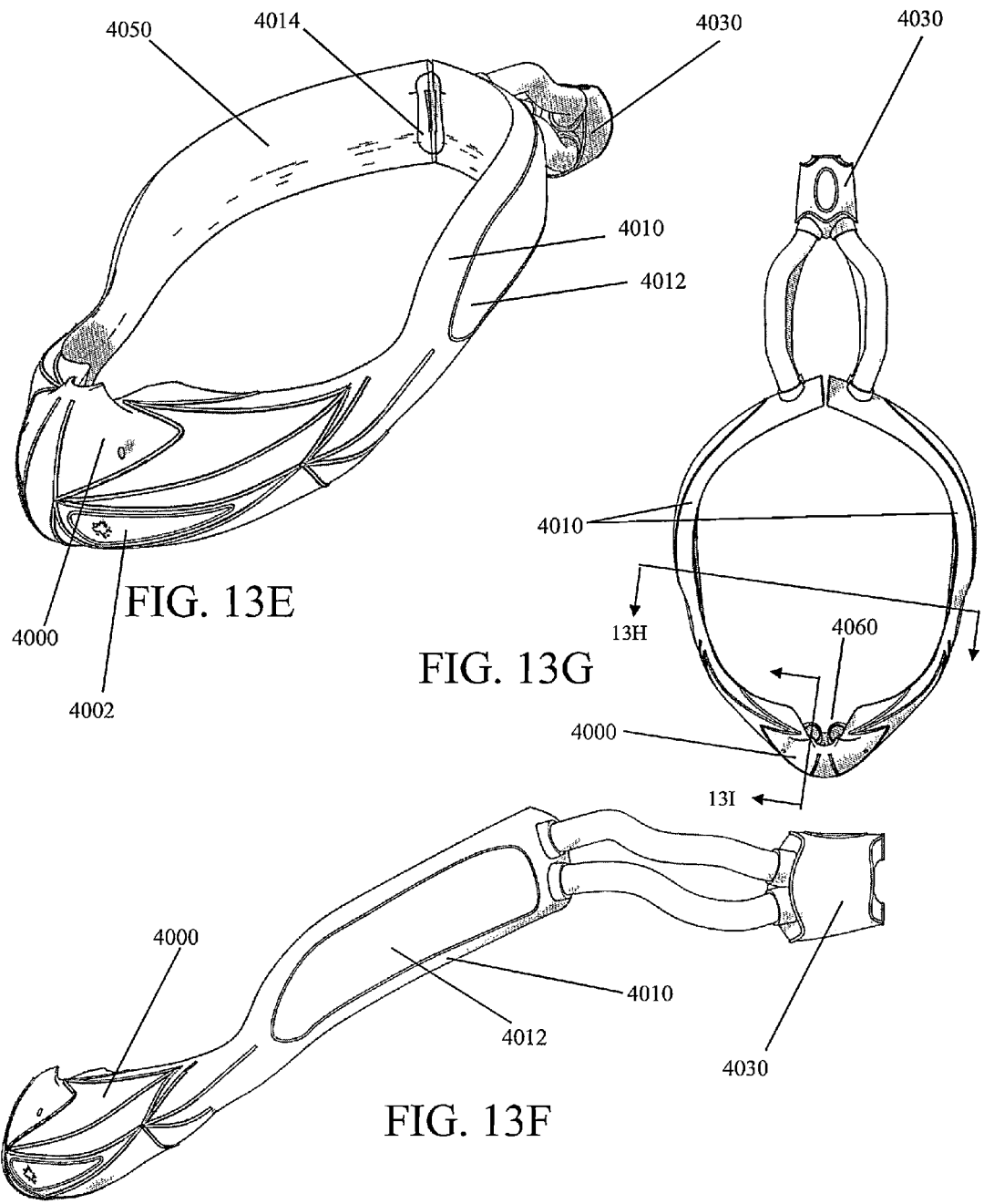

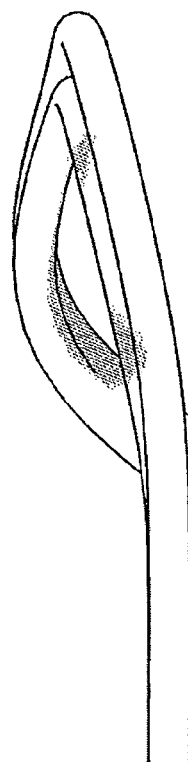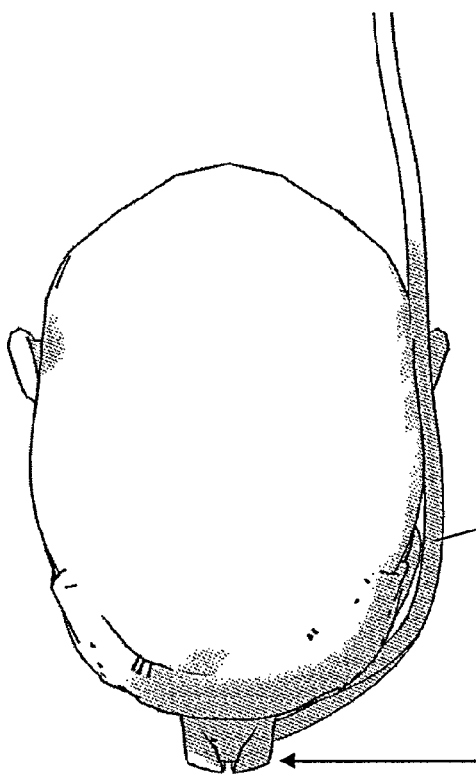
FIG. 15C
FIG. 15D
FIG. 15E

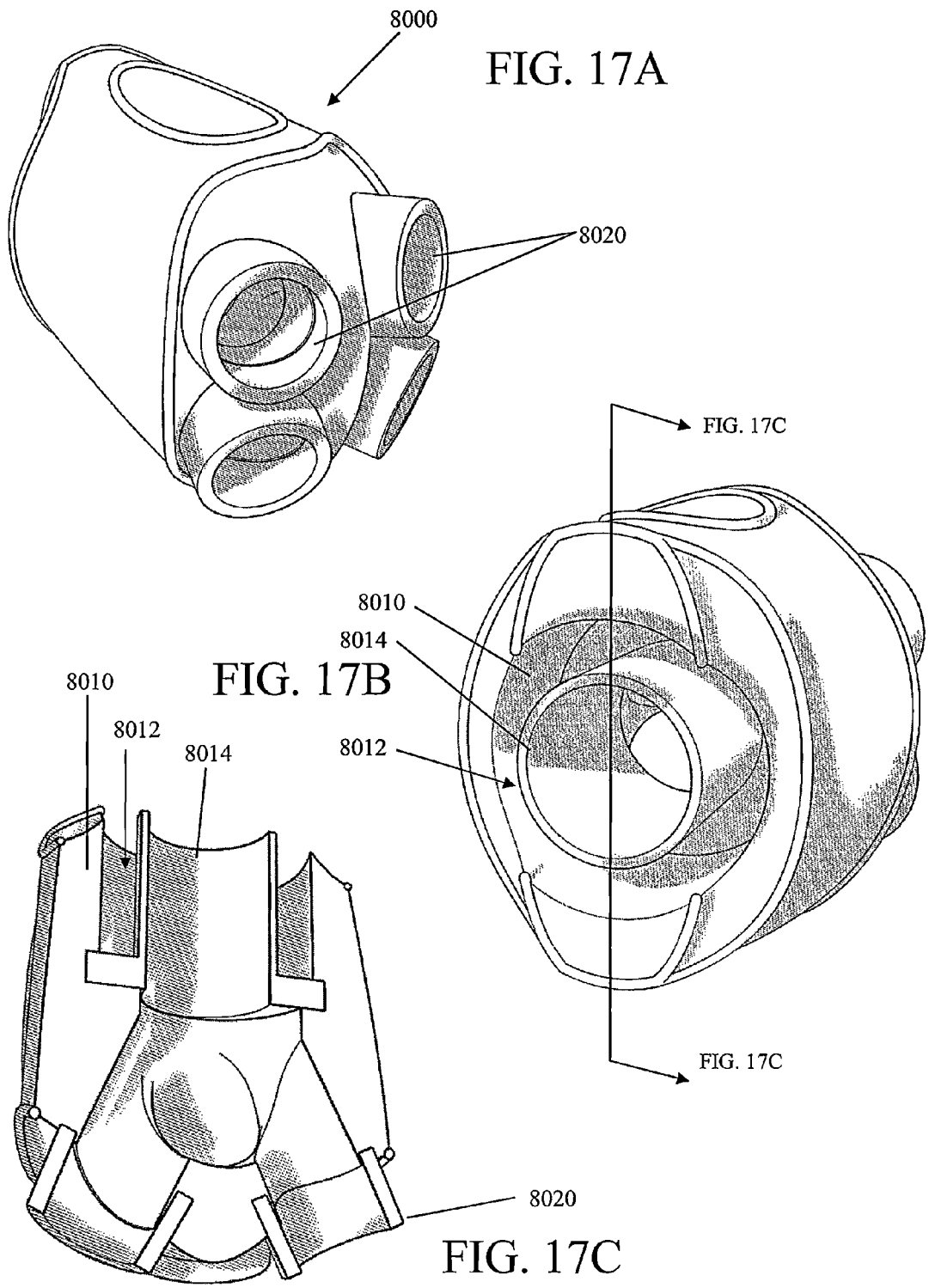

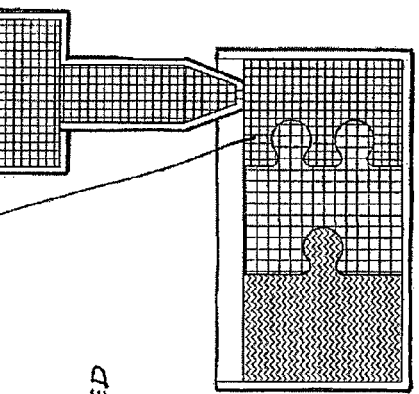
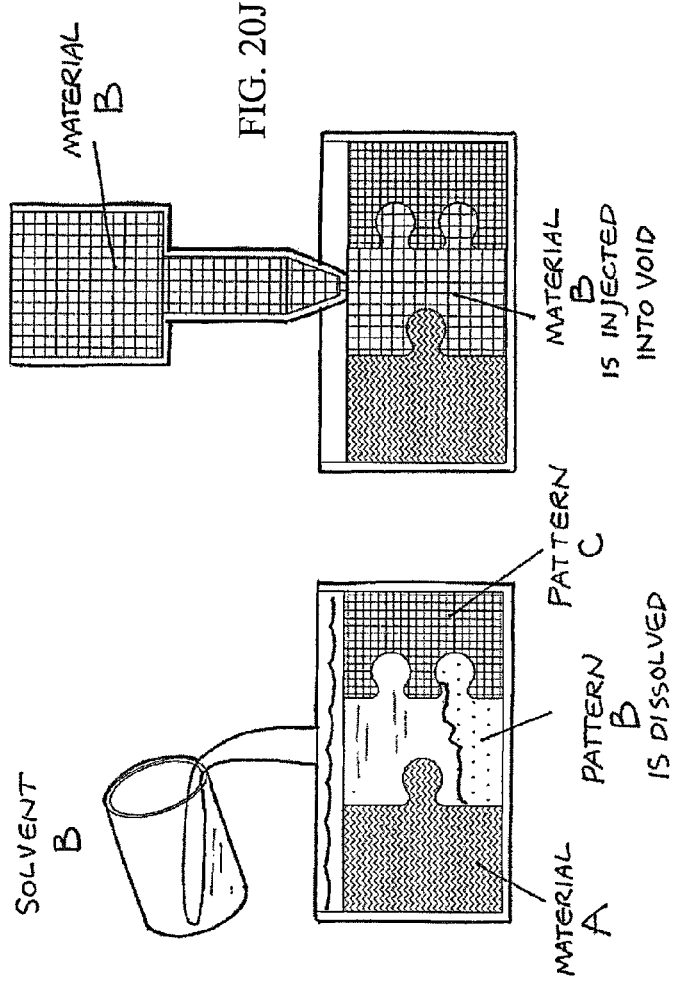
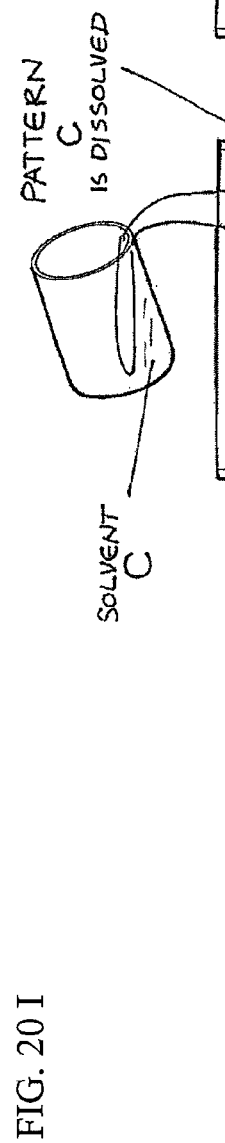
FIG. 20L
FIG. 20J
FIG. 20K
FIG. 20 I

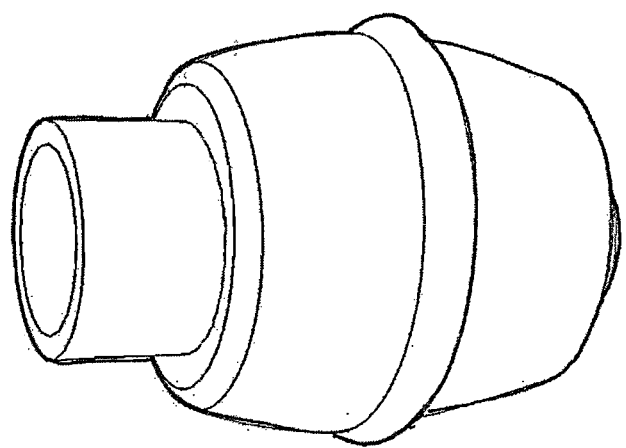
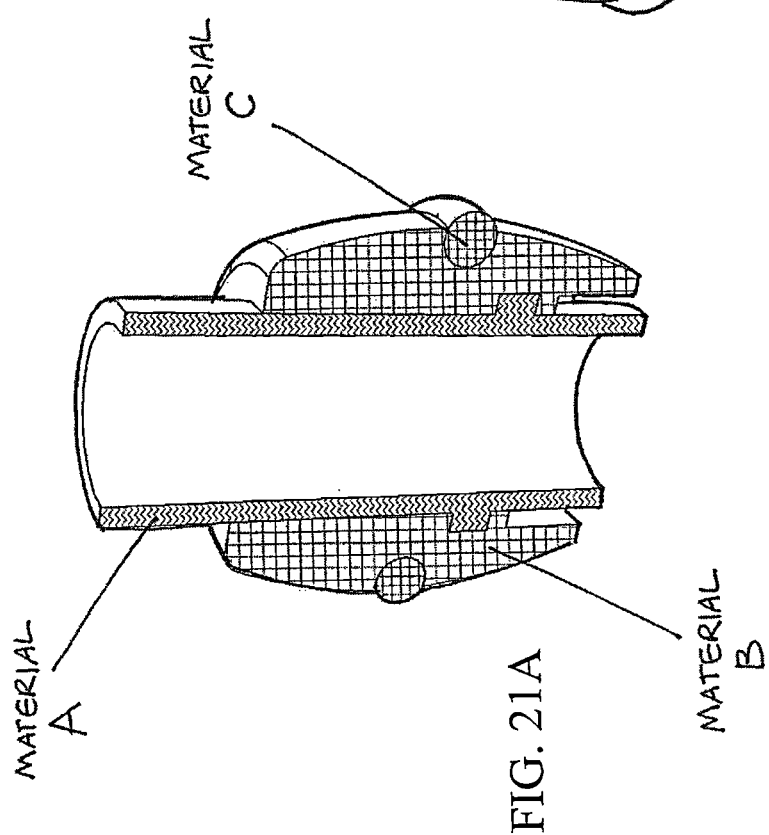
FIG. 21B
FIG. 21A

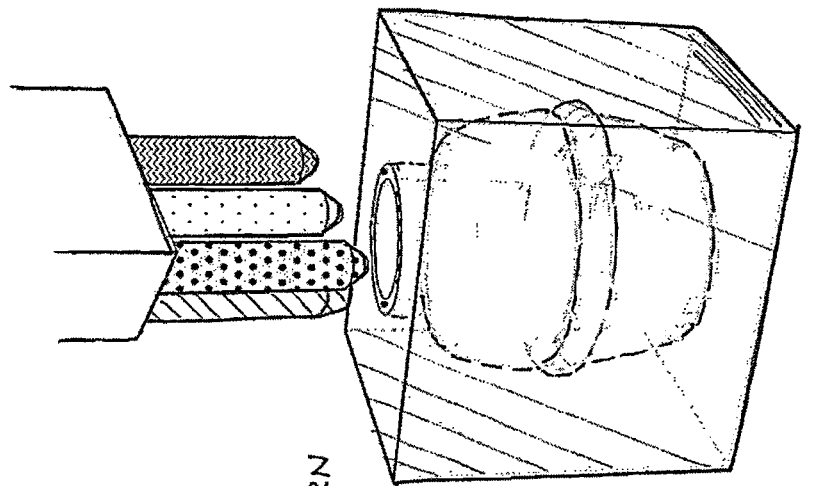
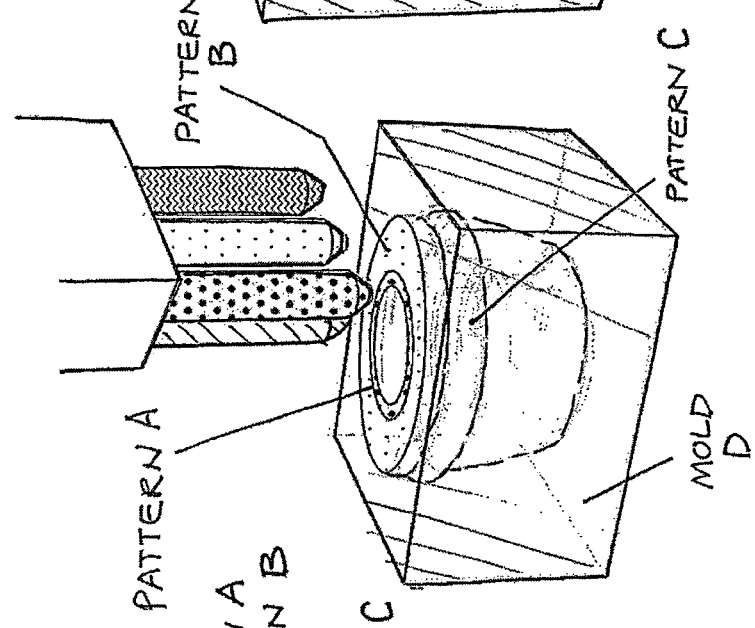
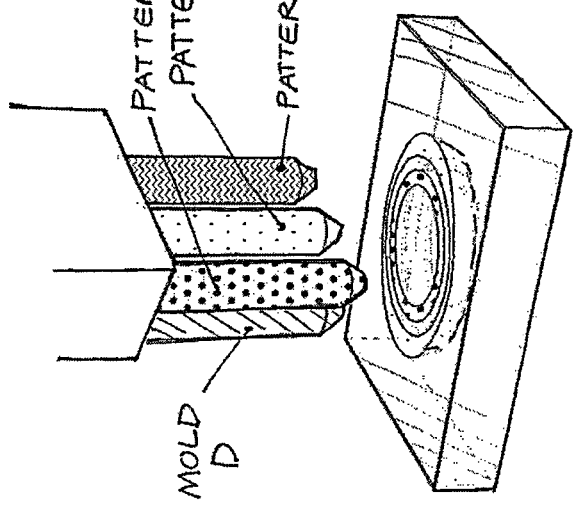
FIG. 21C
FIG. 21D
FIG. 21E

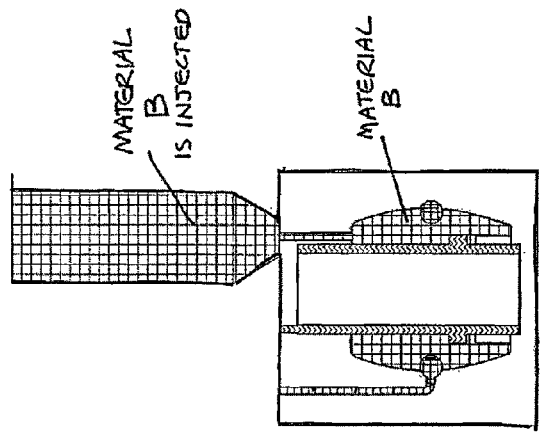
FIG. 21K
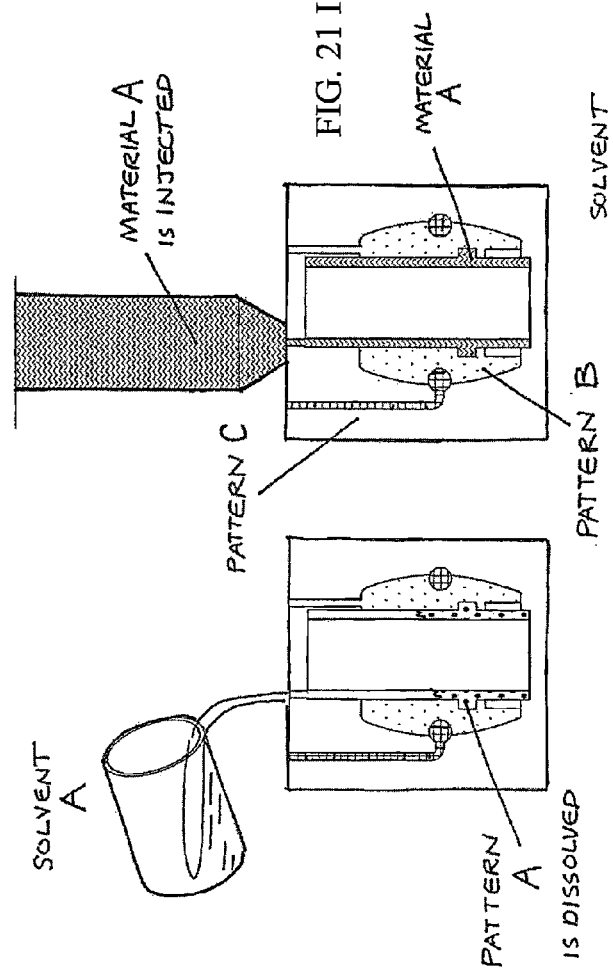
FIG. 21I
FIG. 21J
FIG. 21H

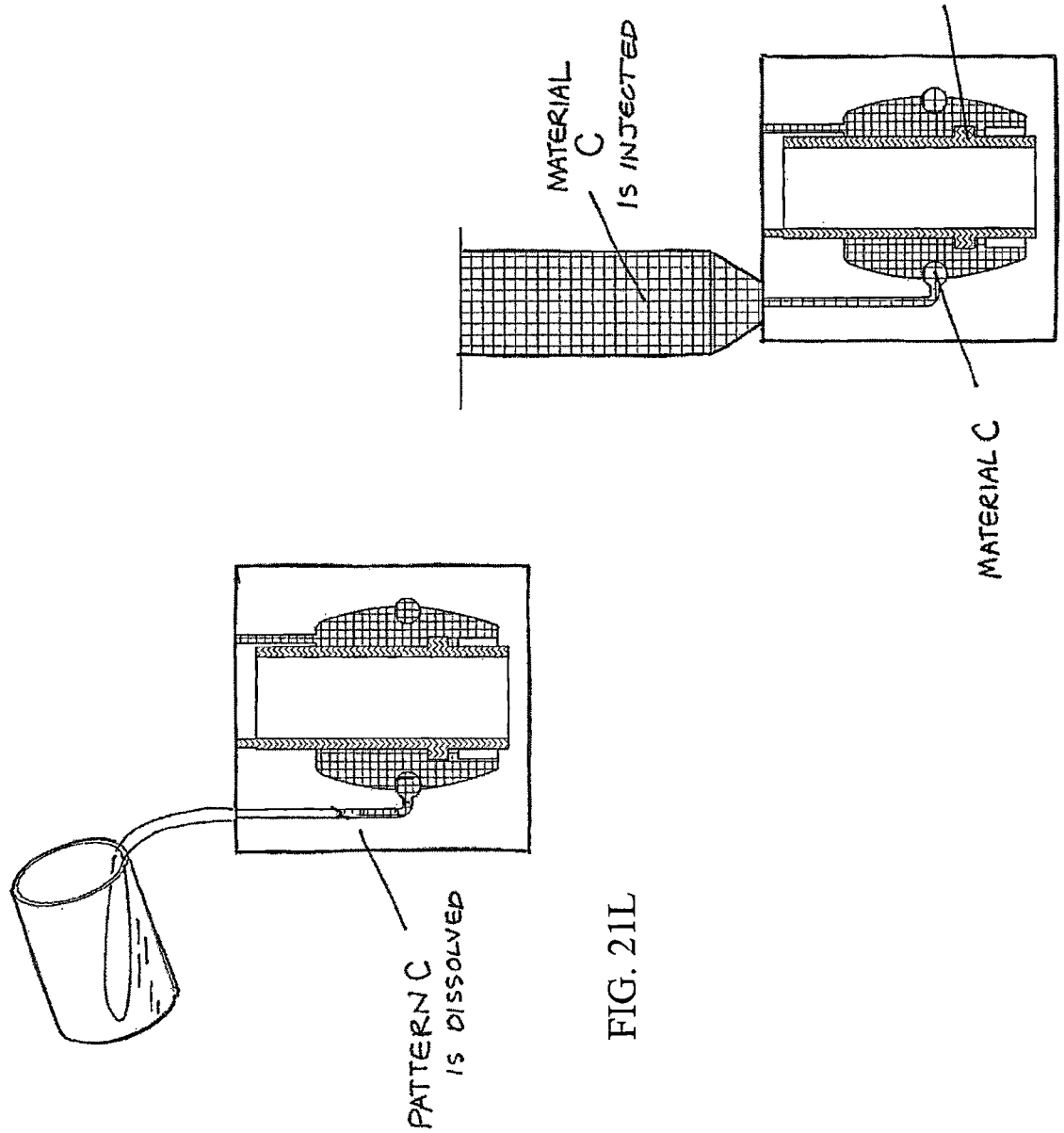

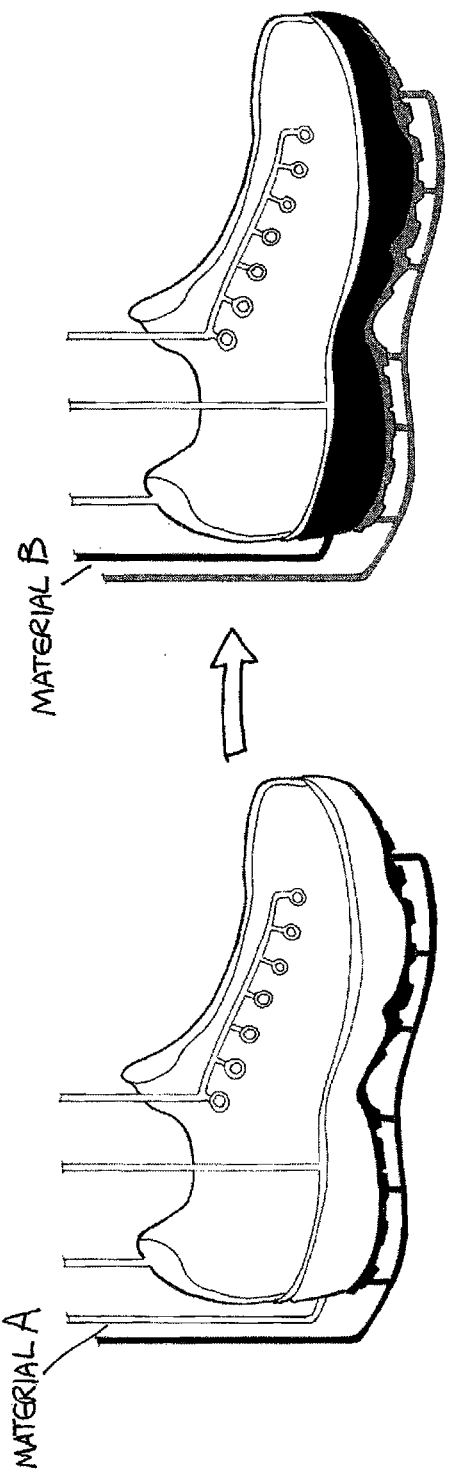

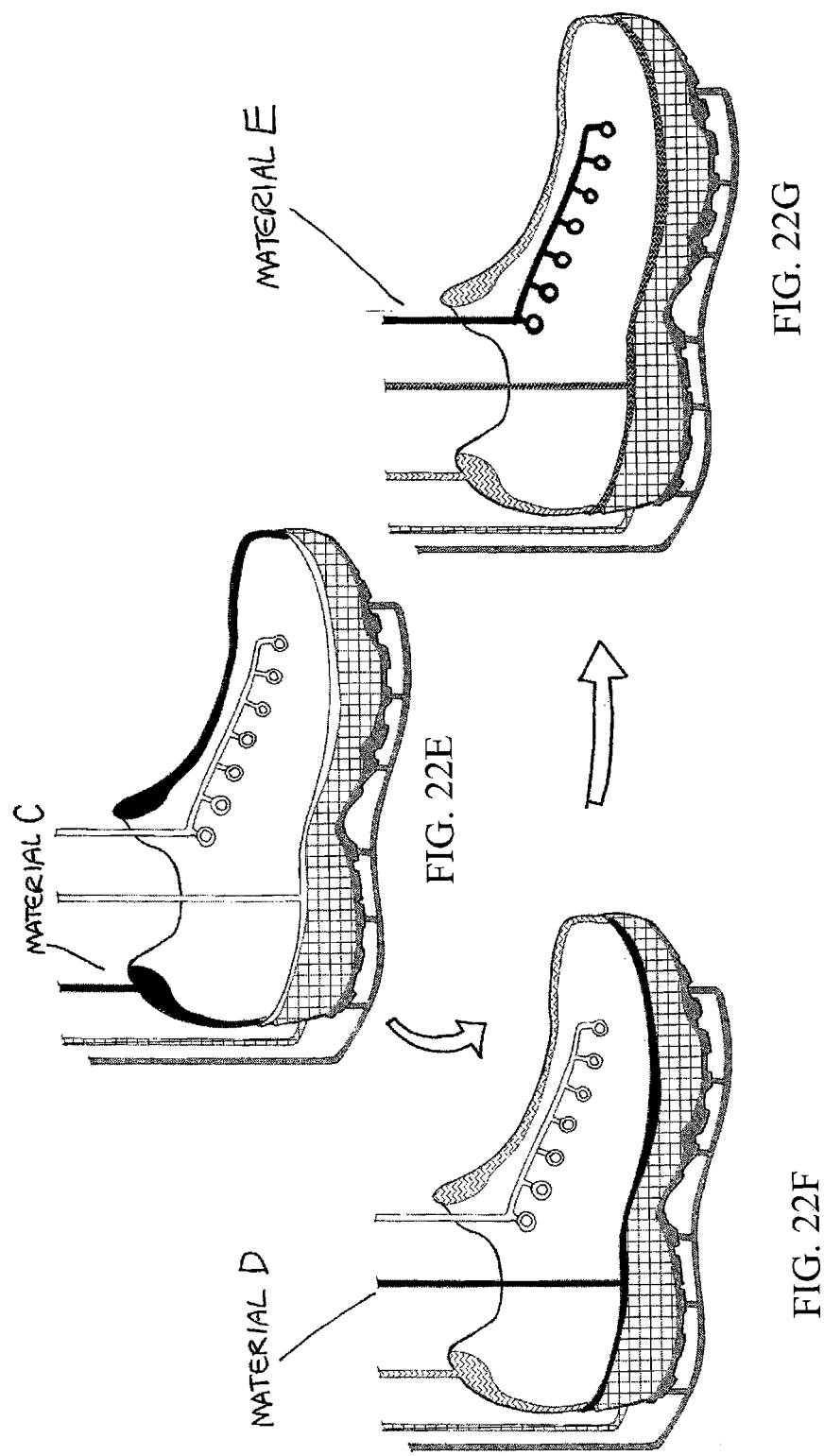

CUSTOMIZED MEDICAL DEVICES AND APPAREL

CROSS-REFERENCE TO RELATED APPLICATION(S)

This application claims the benefit of U.S. Provisional Patent Application Ser. No. 61/828,618 filed May 29, 2013, titled "SYSTEM AND METHOD FOR THE CREATION OF CUSTOMIZED PFD FOR DELIVERY OF RESPIRATORY TREATMENTS"; and claims the benefit of U.S. Provisional Patent Application Ser. No. 61/861,376 filed Aug. 1, 2013, titled "CUSTOMIZED MEDICAL DEVICES AND APPAREL," which is hereby incorporated by reference herein for all purposes.

TECHNICAL FIELD

The invention relates to the production of medical devices and apparel that are custom fit to users. In particular, the invention relates to medical devices and apparel, as well as the systems and method for making them using three dimensional scan data of the users.

BACKGROUND

Millions of people are affected by a disorder called sleep apnea, which occurs when a person's pattern of breathing is interrupted while sleeping. People afflicted with this condition often fail to get enough rest during the night, which leaves them lethargic during the day. A common treatment for some forms of sleep apnea include air delivered using a "continuous positive airway pressure" machine, which delivers air to the patient using a face mask fitted around the patient's nose or nose and mouth. To be effective, the mask must be worn while the patient is sleeping. The mask generally includes plastic and/or rubber components that are held against the patient's face in order to maintain a pressure seal. Current sleep apnea masks are designed to accommodate a large number of patients with a variety of face sizes and dimensions. As a result, current sleep apnea masks may actually may fit poorly, provide a weak pressure seal, and be uncomfortable to wear. For these reasons, there is a need for a sleep apnea mask that is custom fit to the user in order to provide better functionality and wearability, both of which increase the probability that the patient will receive successful treatment over the long term.

SUMMARY

The invention in the preferred embodiment features a system and method for making a wearable article such as a custom sleep apnea mask configured to operate with a CPAP machine. The method preferably comprises the steps of scanning at least a portion of a user's face; generating a surface model of the user's face; and identifying a set of facial features from the surface model. The facial features generally include a first point corresponding to the user's nose, and a second point corresponding to the user's lips. A first contour is generated on the surface model based on the first point, a second contour is generated on the surface model based on the second point, and a third contour may be generated at a position interposed between the first and second contours and offset from the user's nose. The method further includes generating an outer surface of the mask comprising the first, second, and third contours; and generating an inner surface of the mask comprising the surface model between the first and second contours. The inner surface and outer surface may be combined to create a 3D volume of a sleep apnea mask configured to be printed using one of a plurality of 3D printing machines. In some embodiments, the surface model of the user's face is combined with a surface model of a generic head in order to provide a comprehensive data set from which a full head mask can be generated.

In another embodiment, the invention features a sleep apnea system configured to operate with a CPAP machine, wherein the sleep apnea system comprises a face mask, a headband integrally connected to the face mask, and at least one air duct configured to direct air from the CPAP machine to the nasal tubes. The face mask preferably comprises: an inner surface having the same shape as the user's face; an upper surface configured to sit at a first predetermined distance between the user's nose and eyes; and an outer surface configured to extend a second predetermined distance from the inner surface. A pliable coupling may be employed to detachably attach to the CPAP machine, and attach to the at least one air duct. The duct may take the form of an internal duct embedded in the headband, or an external duct including flexible tubes connected to the headband.

In some embodiments, the invention features a custom article prepared by a process comprising the steps of: providing user scan data corresponding to a user face, providing generic model data corresponding to a part of a head, for example, and providing model data corresponding to a sleep apnea mask or other article. The method further includes generating a model of the face and head by merging the user scan data with the generic model data. Thereafter, the model data of the sleep apnea mask is fitted to the model of the face and head based on the location of the user's nose and mouth or other anatomical features. A model of the mask tailored to the head is generated by conforming the model data of the mask to the model of the face and head such that the inside of the mask conforms or otherwise matches the user's face. The resulting mask model may then be transmitted to a 3D printer or other manufacturing process to produce the custom mask. The face and head are just two of a plurality of different body parts for which user scan data and generic model data may be acquired and combined to produce custom medical devices, apparel, or other wearable article.

BRIEF DESCRIPTION OF THE DRAWINGS

The present invention is illustrated by way of example and not limitation in the figures of the accompanying drawings, and in which:

FIGS. 6A-6C are diagrammatic illustrations of a mask model before volume subtraction, a patient head model, and a mask model after volume subtraction of the patient head model, respectively, in accordance with an embodiment of the present invention;

FIGS. 8A-8F are diagrammatic illustrations depicting the parametric fitting process for designing a mask, in accordance with an embodiment of the present invention;

FIGS. 9A-9B are diagrammatic illustrations depicting the press fit process for designing a mask, in accordance with an embodiment of the present invention;

FIGS. 9C-9D are top down views of a mask before and after a mask model is press fit to a face, respectively, in accordance with an embodiment of the present invention;

FIG. 10F is a cross sectional view of a sleep apnea mask, in accordance with a first embodiment of the present invention;

FIG. 10G is a cross sectional view of a sleep apnea mask, in accordance with a first embodiment of the present invention;

FIG. 10H is a front side view of a face mask, in accordance with a first embodiment of the present invention;

FIGS. 10L-10N are perspective views of a right-side manifold used in a sleep apnea mask, in accordance with a first embodiment of the present invention;

FIG. 11E is a perspective view of a retainer used in a sleep apnea mask, in accordance with a second embodiment of the present invention;

FIG. 11F is a perspective view of a retainer used in a sleep apnea mask, in accordance with a second embodiment of the present invention;

FIG. 13E is a perspective view of a sleep apnea mask, in accordance with a fourth embodiment of the present invention;

FIG. 13F is a side view of a sleep apnea mask, in accordance with a fourth embodiment of the present invention;

FIG. 13G is a top down view of a sleep apnea mask, in accordance with a fourth embodiment of the present invention;

FIG. 15C is a back side view showing the inner face of a sleep apnea mask, in accordance with a sixth embodiment of the present invention;

FIG. 15D is a cross sectional view of a sleep apnea mask, in accordance with a sixth embodiment of the present invention;

FIG. 15E is a top side view of a sleep apnea mask, in accordance with a sixth embodiment of the present invention;

FIG. 17A is a front side perspective view of a CPAP coupling, in accordance with an embodiment of the present invention;

FIG. 17B is a back side perspective view of a CPAP coupling, in accordance with an embodiment of the present invention;

FIG. 17C is a cross sectional view of a CPAP coupling, in accordance with an embodiment of the present invention;

FIGS. 20A-20L are diagrammatic illustrations of the 3D printing investment casting technique of the preferred embodiment;

FIGS. 21A-21M are diagrammatic illustrations showing the 3D printing investment casting technique used to make a CPAP coupling; and FIGS. 22A-22G are diagrammatic illustrations showing the 3D printing investment casting technique used to make a running shoe or other article of apparel.

DETAILED DESCRIPTION OF THE PREFERRED EMBODIMENT

Figure 1:
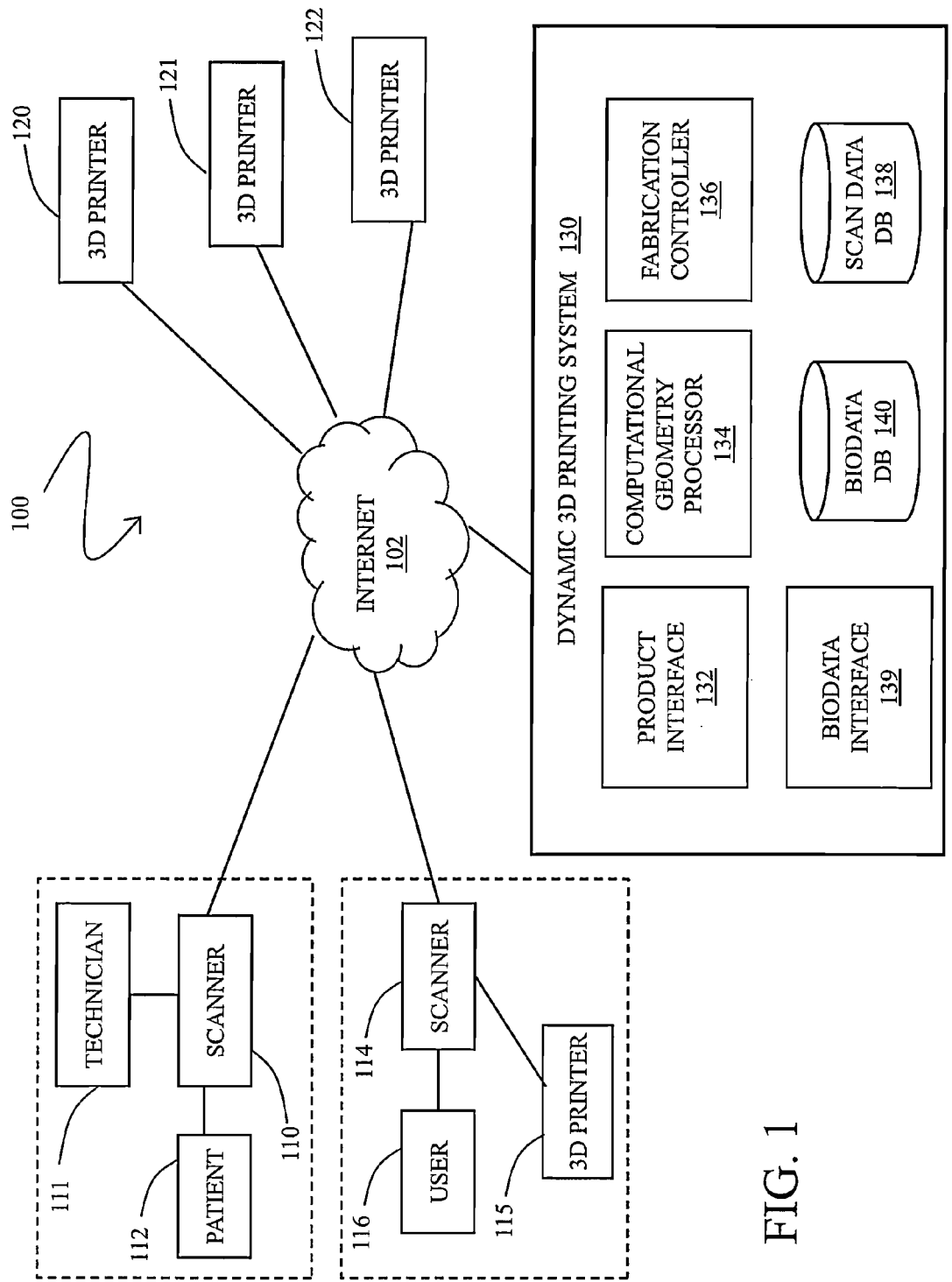
FIG. 1 is a network diagram for 3D printing medical devices and apparel, in accordance with an embodiment of the present invention.

Illustrated in FIG. 1 is a functional block diagram of a network for implementing one or more embodiments of the present invention. The network includes a Dynamic 3D Print Design System (DPDS) 130 configured to design medical devices and other body-fitted components customized for individual users. In the preferred embodiment, the medical device is a sleep apnea mask, although the DPDS is capable of producing numerous other medical and non-medical devices including eyewear, goggles, ski masks, scuba masks, footwear, and other apparel. Each mask is custom manufactured based on 3D scan data of the patient to ensure a superior fit and comfort, which, in turn, enhances the effectiveness of the mask and resulting treatment. The custom-fit masks are then produced using manufacturing techniques that may include one or more 3D printers 120-122 or other rapid prototyping and computer-aided manufacturing techniques that construct objects layer-by-layer, for example.

The patient scan data may be acquired using any of a number of different scanning systems known to those skilled in the art. Suitable scanning systems may include scanners (from 3D Systems, Inc. of Rock Hill, S.C., for example) capable of collecting data points in a three dimensional Euclidean space, for example. In some embodiments, the patient 112 scan data may be acquired by a technician 111 using a scanner 110 located in a hospital, clinic, pharmacy, or retail facility, for example. In other embodiments, the scan data is acquired by a user 116 himself or herself with a personal scanning device 114, for example. In the preferred embodiment, the scan data generally consists of 3D volume data characterizing the shape, size, and contours of the head and/or face of the patient in a three dimensional coordinate system such as a Cartesian, polar, or spherical coordinate system. The scan data may be represented as raw point cloud data or converted to a surface model in one of the following forms: non-uniform rational B-spline (NURB) data, sub-divisional NURBS (aka, sub-dNURBS), polygonal mesh, and/or combination of parametric definitions. Common file types for representing scan data include mesh file types: .mud/.mb/.anim/.iff/.cpp/.fxa/.spt/.c4d/.aec/.exr/.mc4d/.3ds/.max/.act/.bip/.cel/.exr/.ztl/.stl/.ply/.amf; NURBS file types: .lxo/.blend/.blend2/.obj/.off/.mdd/.exr/.sdl/.wire/.3dm/.3dx/.ws/.3dc; and parametric file types: .dgn/.dgr/.rdl/.svf/.dwg/.dxf/.adsk/.ies/.rvt/.skp/.easm/.dwf/.dwfx/.iam/.idw/.ipt/.drw/.dxf/.jt/.lay/.prt/.sec/.slp/.stl/.drw/.dxf/.jt/.lay/.prt/.sec/.slp/.3dmap/.3dxml/.c18/.catpart/.catshape/.model/.sldprt/.sldasm/.tso/.xli/.scdoc/.ad_prt.

The patient scan data is then provided to and processed by the DPDS 130 to generate a medical device for the patient. Depending on the application, the DPDS 130 may be co-located with the scanner, or remotely located at a separate facility accessible via the Internet 102. In the preferred embodiment, the DPDS 130 includes a product interface 132, computational geometry processor 134, fabrication controller 136, and scan data database 138. The product interface 132 is generally used to select and define one of a plurality of medical devices or components to be generated from the patient's scan data. The computational geometry processor (CGP) 134 is configured cleanse the scan data of artifacts, fit a generic model of the selected medical device to the scan data, and generate a unique model of the selected mask custom fit to the individual patient. The fabrication geometry processor (FGP) 136 then converts the data representing the custom mask into one or more ".STL" files and/or other manufacturing instructions tailored to the one or more 3D printers 120-122 selected/employed to manufacture the custom mask for the patient. In some embodiments, the DPDS 130 further includes a biodata interface 140 configured to utilize a patient's personal biological or physiological data 140 to alter the size, shape, or features of the patient's mask and/or the mask's functionality.

Figure 2:
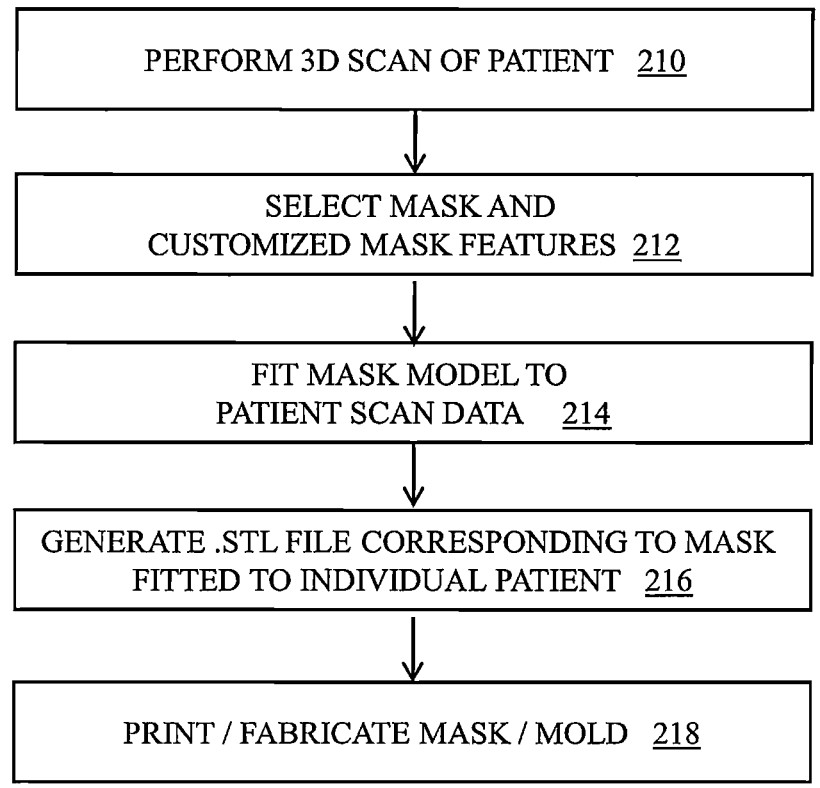
FIG. 2 is a flowchart of the method for 3D printing medical devices and apparel, in accordance with an embodiment of the present invention.

Illustrated in FIG. 2 is a flowchart of the process of generating a custom-fit sleep apnea mask or other medical device. After a 3D scan of the patient's face and/or head is acquired 210, one of a plurality of mask types is selected 212 along with any applicable design features or customization. The selected mask type is associated with and used to retrieve a digital model of a mask. The mask model is then fitted 214 to or intersected with the patient scan data in order to produce a new mask model that is compliant with the patient's facial features. The resulting mask will, therefore, provide a reliable pneumatic seal with maximal comfort.

Using the mask model modified for the patient, one or more data files and computer instructions are generated 216 and used to construct or otherwise fabricate 218 the custom-fit mask for the patient.

Figure 3:
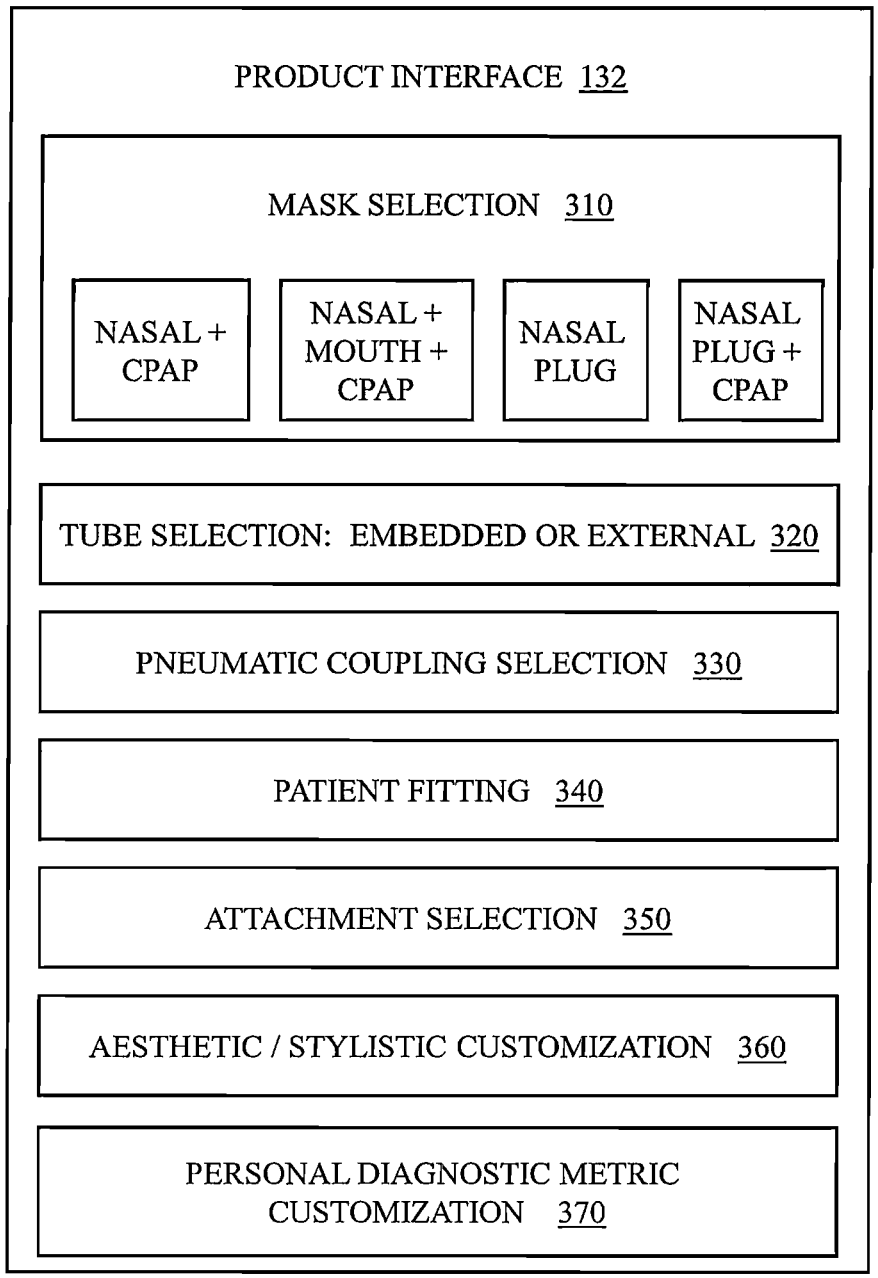
FIG. 3 is a functional block diagram of a user interface for designing and defining custom masks for patients and other users, in accordance with an embodiment of the present invention.

Illustrated in FIG. 3 is the product interface in accordance with the preferred embodiment of the DPDS 130 shown in FIG. 1. The product interface 132 includes a mask selection processor 310 that enables a technician or other operator to view and select a suitable sleep apnea mask from a plurality of mask options, including, for example, (1) a nasal mask configured to operationally attach to and receive air from a continuous positive airway pressure (CPAP) machine, (2) a mask fitted for the mouth and nose with a CPAP attachment, (3) a mask with nasal tubes and CPAP attachment, and (4) a mask with nasal tubes and valves. The masks with a CPAP attachment generally include a coupling and one or more integrated air ducts for connecting the sleep apnea device to the pressurized CPAP output. In some embodiments, these one or more air ducts include ducts either embedded into the mask or sets of elastic tubes routed external to a mask headband.

The tube selection processor 320 is then used to choose between the embedded or external ducting option if available. The pneumatic coupling selection 330 enables the technician to select from a plurality of attachment mechanisms used to directly connect the CPAP output tube and mask. The attachment mechanisms generally include different couplings corresponding to different sizes, shapes, and locations on the patient's head. The patient fitting processor 340 enables the technician to adjust the mask model in order to better fit it to the patient. Although this fitting process is done automatically in the preferred embodiment, the interface 132 may enable the technician to manually adjust the size of the mask and headband, for example, to reduce pressure on the patient's face or head, or adjust the mask and headband to account for the position in which the patient sleeps. The location of the headband may also be adjusted in order to avoid interfering with the patient's eyes or ears, for example. In the module for attachment selection 350, the technician can modify the mask model to include alternate mechanisms to affix the mask to the patient including, for example, one or more magnets or shape changing alloy may be inserted into the mask to generate a force that biases the mask against the patient's face. Using a customization processor 360, the model of the selected mask may be modified to include aesthetic and stylistic design features including colors, patterns, graphics, and embossing, for example.

In some embodiments, the product interface further includes a processor 370 for customizing the mask based on personal diagnostic metrics (PDM). PDMs may include the airflow capacity of the patient's esophagus and nasal cavity (determined with magnetic resonance imaging (MRI) scan data or x-ray scan data, e.g.), which may be used to determine the optimal size and shape of the air ducts in the sleep apnea mask. If a patient has difficulty breathing due to a blocked nasal passage, for example, the air passages in the sleep apnea mask may be enlarged to provide maximal air flow, thereby compensating for the patient's physical condition.

Figure 4:
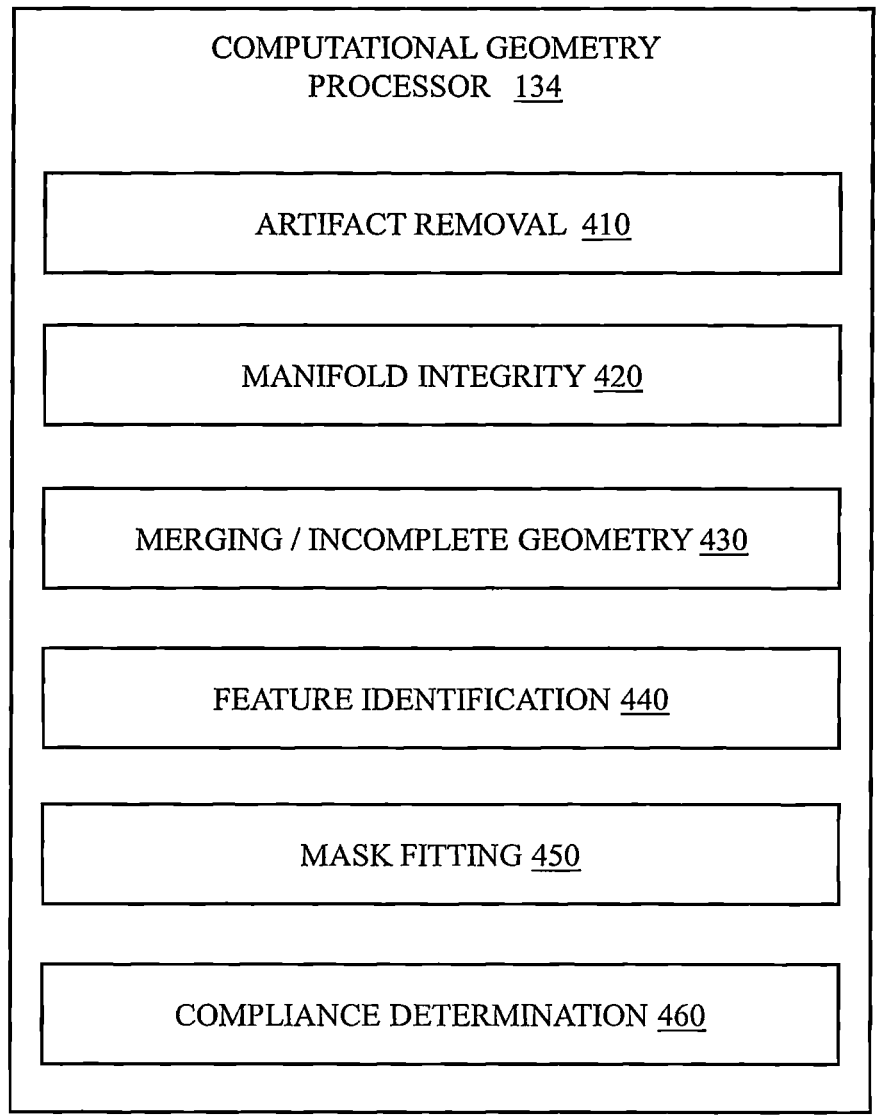
FIG. 4 is a functional block diagram of a computational geometry processor used in the Dynamic 3D Print Design System (DPDS), in accordance with an embodiment of the present invention.

Illustrated in FIG. 4 is the computational geometry processor (CGP) 134 in accordance with the preferred embodiment of the DPDS 130 shown in FIG. 1. The CGP 134 is configured to receive the mask model from the product interface 132 as well as the patient scan data. Prior to merging the mask model and the scan data, artifacts are identified and removed from the scan data using an artifact removal module 410. A significant source of artifacts is a patient's hair which does not scan well, resulting in gaps and erroneous scan points in the data set. The CGP 134 further includes a manifold integrity processor 420 which is configured to convert the patient scan data to a manifold surface, if not already, and then remove any holes or apertures in the manifold that might prevent or interfere with the production of the mask model or 3D print operation.

Figure 5C:
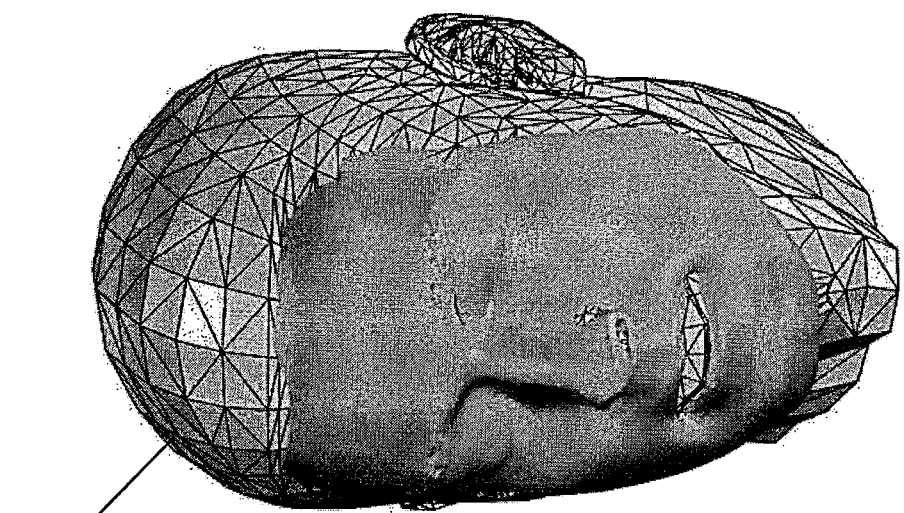
FIGS. 5A-5C are diagrammatic illustrations of patient scan data, a generic head model, and a model including a combination of the patient scan data and the generic head model, respectively, in accordance with an embodiment of the present invention.
Figure 5B:
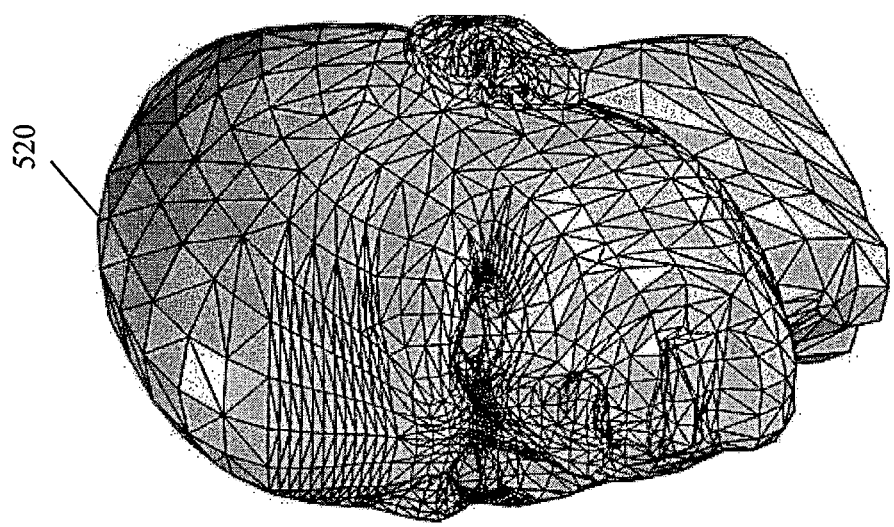
Figure 5A:
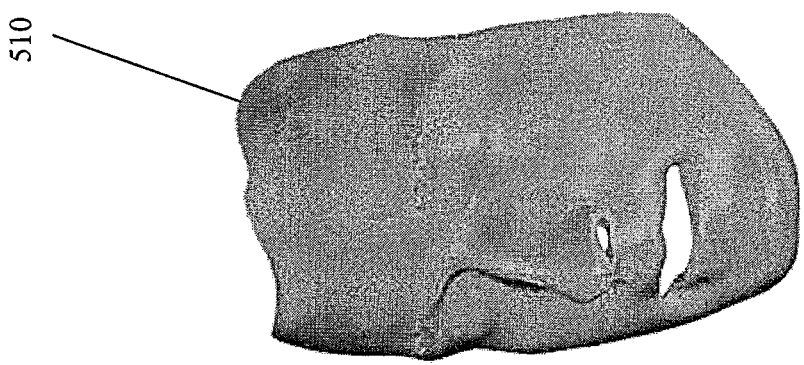

In some embodiments, the patient scan data consists of a manifold representing the face, which generally includes the region from the forehead to the chin and from ear to ear. Depending on the embodiment, scan data representing the face alone may be insufficient to make a sleep apnea mask with compliant head strap or headband. To address this incomplete data set, the CGP 134 includes a processor 430 configured to merge the face data together with a generic model of a head to produce a model of the complete patient head. The process of merging or otherwise combining face data and head data is shown schematically in FIGS. 5A-5C. In the preferred embodiment, the face data is represented as a 2D surface shown in FIG. 5A, and a generic model of a head shown in FIG. 5B. The head data and/or face scan data are then scaled, rotated, stretched, smoothed, or otherwise morphed to merge the head data with the face data. The transitions between the face data and head model should be proportionate and smooth and continuous at the boundaries. Any gaps between the face manifold and head manifold may be filled using one of multiple surfacing techniques known to those skilled in the art including lofting, for example. The result is a single manifold surface including face and head representing the individual patient's complete head, as shown in FIG. 5C. Although the preferred embodiment employs morphing and lofting techniques, one skilled in the art will appreciate that there are other techniques for generating a model of a complete head using scan data representing the face alone.

In some embodiments, the head data to be merged with the face data is selected from a plurality of different generic head models. A database with a plurality of generic head models may be compiled in order to provide a selection of models with which to represent people of different body shapes and proportions. Models of heads may be selected for patients based on each patient's ancestry, gender, age, weight, and face dimensions/aspect ratio, for example. Candidate head models may be tested and the optimum model identified and merged with the face data. In the preferred embodiment, the optimum head model yields the least geometric error, that is, the head model that provides maximal tangency between the head data and face data. Maximal tangency corresponds to a minimum rate of change in curvature at the boundary between the surface of the head data and face data, averaged over the entire boundary.

Thereafter, a feature identification processor 440 locates one or more anatomical features—e.g., eyes, nose, mouth, and ears—in the model of the patient head. The identified features serve as control points for purposes of automatically aligning, registering, fitting, shaping, and/or designing the customized mask model without the aid of an operator. After the mask model is designed, however, the control point fitting processor 450 is configured to enable an operator to subsequently adjust the size, position, and/or orientation of the mask to fit over the mouth and/or nose, or adjust the position of straps or external air ducts (if present) around the patient's cheeks and above the patient's ears, for example.

In one preferred embodiment, the model of the mask is designed using a technique referred to as "Boolean volume subtraction," which is illustrated in FIGS. 6A-6C. In the volume subtraction technique, a 3D model of a mask and 3D volume of the patient's head are superimposed and a portion of the mask subtracted away from the mask model. In particular the 3D mask model 510 in FIG. 6A is made to extend or protrude into the interior space of the model 520 of the head in FIG. 6B so that the two models are overlapping in the region of the face and straps. Once the mask and patient scan data are aligned, a compliance determination processor 460 subtracts the portion of the mask model that intrudes into the interior of the model of the head. The remaining portion of the mask 530 is thus a custom mask having an inner surface that exactly matches and conforms to the patient's face. Because each patient is unique, each mask model is therefore also unique. Other techniques for designing the custom-fit mask are discussed in context of FIGS. 8A-8F as well as 9A-9D.

Figure 7:
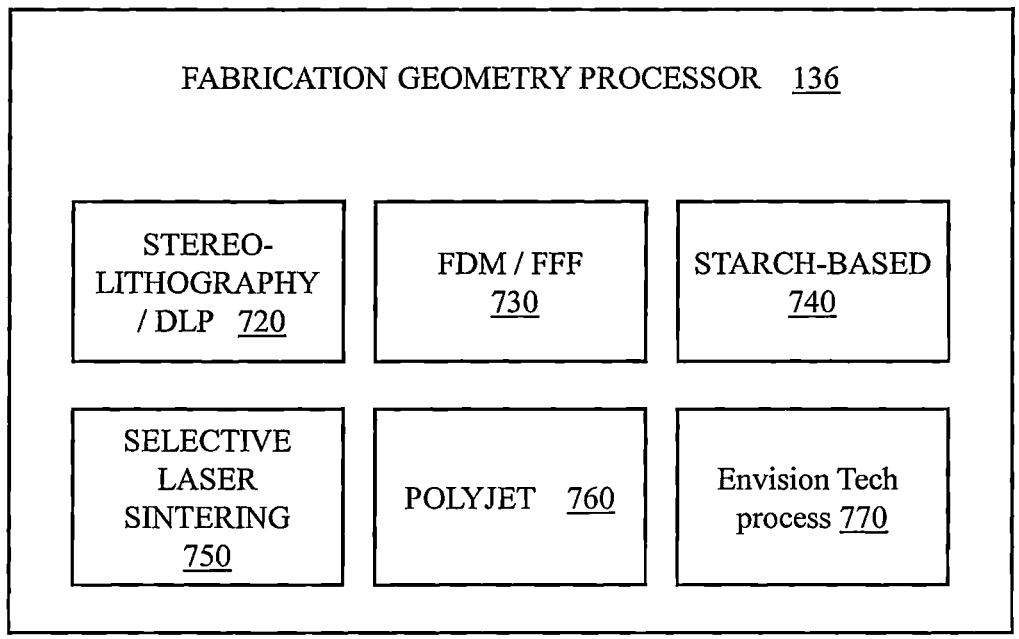
FIG. 7 is a functional block diagram of a fabrication geometry processor used in the DPDS, in accordance with an embodiment of the present invention.

Illustrated in FIG. 7 is the fabrication geometry processor (FGP) 136 in accordance with the preferred embodiment of the DPDS 130 shown in FIG. 1. Using the FGP 136, a technician selects a manufacturing system or technique for one or more components of the sleep apnea mask. The technique may involve direct 3D printing of one or more mask components, and/or 3D printing of a mold from which one or more mask components are cast. As shown, the user can choose to construct the portion of the mask or mold using, for example, stereolithography (SLA) 720, fused deposition modeling (FDM) 730, fused filament fabrication (FFF), starch-based printing system 740, selective laser sintering (SLS) 750, additive manufacturing techniques like POLYJET™ printing 760, and/ENVISION TEC™ 3D printing. Once the manufacturing methodologies are selected, the FGP 136 converts the custom mask model into one or more print files, manufacturing instructions, and/or assembly instructions specific to the selected 3D printer or printers. This generally involves generating one or more ".STL" files from the parametric solids, mesh, or non-uniform rational B-spines (NURBS) data models.

In addition to the "Boolean volume subtraction" technique discussed above, the custom-fit mask may be designed using various other techniques including (a) a "NURBS subtraction" technique, (b) a "parametric fitting" design technique illustrated in FIGS. 8A-8F, and (c) a "press fit" design technique illustrated in FIGS. 9A-9D. In the "NURBS subtraction" technique, the compliance determination processor 460 converts the patient model (including the combination of face data and head data) from a mesh model to a non-uniform rational basis spline (NURBS) model. The model of the mask, which is also represented as a NURBS, is super-imposed with the NURBS patient model. As discussed above, the size, position, and proportions of the mask may be adjusted, as needed, to account for anatomical features located by the feature identification processor 440. After the head and mask models are aligned, a compliant version of the mask model is generated based on the intersection of the mask NURBS and the patient NURBS. In particular, the portion of the NURBS of the patient model bounded by the mask model is identified, and the portion of the NURBS of the mask model lying outside the patient model is identified. The NURBS of the patient model is the section of the patient model between the upper edge and lower edges of the mask where the mask and patient models intersect. The NURBS of the mask model is the section of the mask model extending outward from the patient model. Each of the two portions represent NURBS surfaces which, when combined, form a NURBS volume representing a compliant mask. The NURBS volume is then processed by the fabrication geometry processor in the manner described below.

In the "parametric fitting" design technique illustrated in FIGS. 8A-8F, the outer surface of the mask as well as the interior volume are custom designed for each patient. The current technique differs from other techniques where only the inner face of the mask is custom designed for an individual patient. In the present embodiment, the (a) the inner surface of the mask, (b) the interior structure of the mask, and (c) the outer surface of the mask are all custom designed for each patient in order to optimize the fit, optimize the air flow, and/or minimize the size/material need to construct the mask, for example. In this parametric fitting process, points or other features on the users face are located or otherwise measured in three dimensions and the mask shape determined relative to those points and/or measurements. The parametric fitting process insures that the mask conforms to each patient regardless of the height, width, and overall size the patient's face, nose, and cheeks, all of which vary widely based on age, gender, ethnicity, etc.

In the preferred embodiment, the parametric fitting process of designing the mask begins with the acquisition of the patient's 3D head model and feature recognition, as described above. Once the location of the eyes, nose, and mouth are determined, the mask design system locates the following specific anatomical points in the patient scan data: (a) tip of the nose 810, (b) bridge of the nose 812 between the eyes 814, (c) the upper-most point of the lips 816 closest to the nose, (d) the underside of the nose 818 closest to the upper lip, (e) the width of the face 822, 824, and (f) the center points of the nostrils 820. In general, these points vary in location from patient to patient. Using the anatomical points acquired from the scan data, the mask design system determines the optimal location of the (a) upper edge of the mask, (b) the shape of the upper edge of the mask, (c) the bottom edge of the mask, (d) the shape of the bottom edge of the mask, (e) the height of the mask off the face across the entire face.

First, the mask fitting module 450 locates a point about half way between the tip of the nose and bridge of the nose, referred to herein as the mid-nose point 830. In the preferred embodiment, this point is 60% of the distance between the tip and bridge of the nose as measured from the tip. The mid-nose point then anchors the upper edge of the mask. Second, a predetermined curve 832 defining the desired shape of the mask is then fitted between the mid-nose point and the left side 822 of the face, and between the mid-nose point and right side of the face as defined by the facial width measurement. The curves spanning the left and right sides of the face, which are represented in a single plane, are then projected directly onto the patient's face scan data. The intersection of the projection of the curves and the scan data is represented by a contour in 3D space. This first contour 840 locates the upper edge of the mask.

Third, the mask system locates a point about half way between the lips and nose, referred to herein as the philtral dimple point or just dimple point 834. In the preferred embodiment, this point is 40% of the distance between the upper tip 816 of the upper lip to the lower side of the nose as measured from the upper lip. This dimple point 834 then anchors the lower edge of the mask. Instead of the dimple point 834, a point below the lips may be selected to construct a mask that covers both the nose and mouth. Fourth, a second predetermined curve 836 defining the desired shape of the mask is then fitted between the dimple nose point and the left side 824 of the face, and between the dimple point and right side of the face as defined by the facial width measurement. The curves spanning the left and right sides of the face, which are represented in a single plane, are then projected directly onto the patient's face scan data. The intersection of the projection of the curves and the scan data is represented by a contour in 3D space. This second contour 842 locates the lower edge of the mask. The portion of 3D patient head data between the first contour 840 and the second contour 842 is illustrated with hashing 841 in FIG. 8C.

Figure 8F:
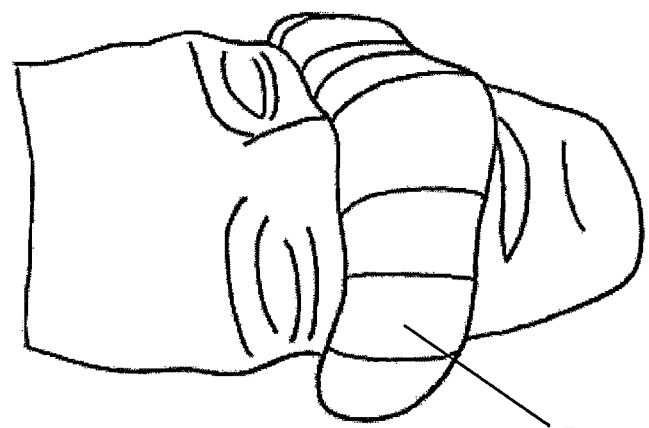
Figure 8E:
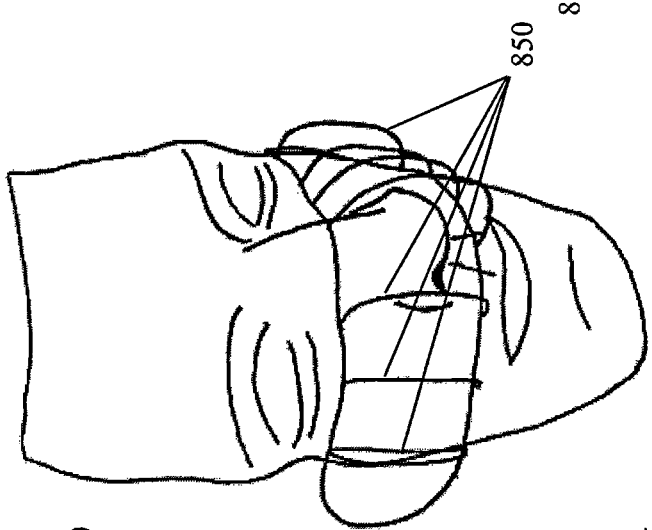
Figure 8D:
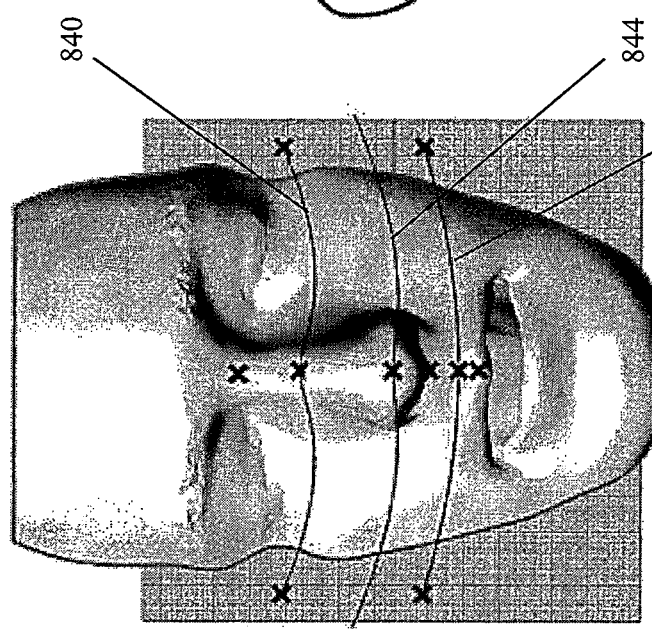

Fifth, a mask offset defining the forward-most edge of the mask is determined with the aid of a "tween contour" 844 shown in FIG. 8D. The tween contour is computed by (1) generating a 2D tween curve by averaging the vertical height of the upper and lower contours 840,842 described above; (2) generating a 3D tween curve by projecting the 2D tween curve onto the patient head data to determine the intersection between the two; (3) generating an offset tween curve by taking the 3D tween curve coinciding with the scan data and adding a fixed lateral offset distance in the direction in front of the face; and (4) generating the final tween contour 844 by smoothing or otherwise low-pass filtering the offset tween curve from the middle of the curve to the edges of the curve. The offset distance can be set to a specific wall thickness, set to a specific distance beyond the tip of the nose, or varying the offset in relation to the height of the mask.

The upper and lower contours 840, 842 along with the final tween contour 844 are the foundations for a plurality of cross section curves that are then used to make the outer surface of the mask. The cross section curves 850 shown in FIG. 8E define the general cross section at various points along the width of the mask. At each point along the width, a cross section curve is a line generated such that it lies in a common plane and intersects the upper and lower contours 840, 842 as well as the final tween contour 844. This plane generally projects at substantially a right angle from the face scan data at the point it intersects the upper contour. The outer surface 860 of the mask is then produced by generating a surface that includes each of the cross section curves.

In addition to the outer surface 860 of the mask, the upper and lower contours are also used to determine the inner surface of the mask. In particular, the upper and lower contours are used to identify and segment the relevant section of the patient's face scan data or head data 841 shown with hash marks in FIG. 8C. This segment of the scan data 841 is then combined with the outer surface of the mask 850 to generate a closed 3D volume from which the mask may be printed.

In some embodiments, the initial shape define by the inner and outer surfaces then act as a template to which other mask features are integrated including nasal tubes, hose connections, clips, and/or ducting, for example. In the preferred embodiment, nasal tubes are also designed based on anatomical points including (a) the center points of the nostrils 820, (b) tip of the nose 810, and (c) bridge of the nose 812. In particular, the nasal tubes are concentric about the center points of the nostrils, and the orientation of the nasal tubes is parallel to the line segment joining the tip of the nose 810 and bridge of the nose 812.

In another embodiment, the mask is designed using the "press fit" design technique illustrated in FIGS. 9A-9D. In this process, the mask is designed by morphing or otherwise conforming a generic mask onto the patient scan data. Using a generic 3D model of a mask, the mask is first scaled, rotated, and vertically aligned at a position in front of the face scan data using the anatomical features and various points including the mid-nose point 830 and dimple point 834. That is, the mask model is positioned adjacent to the scan data by adjusting the upper and lower edges of the mask to coincide, vertically, with the mid-nose point as well as the dimple point. The mask model 910 is adjacent to the scan data 930 in the perspective view of FIG. 9B and in cross section in FIG. 9C. Second, the mask model 910, which is in front of the scan data 930, is mathematically pressed onto or stretched on the face such that the inner surface 920 of the mask takes on and/or conforms to the shape of the scan data 930. The generic mask before pressing is shown in FIG. 9C and the custom mask 912 after pressing is shown in FIG. 9D. The stretching operation is complete when the inner surface 920 of the mask is substantially similar to the patient's face scan data. The final mask model may then be transmitted to the printer for manufacturing.

Figure 10A:
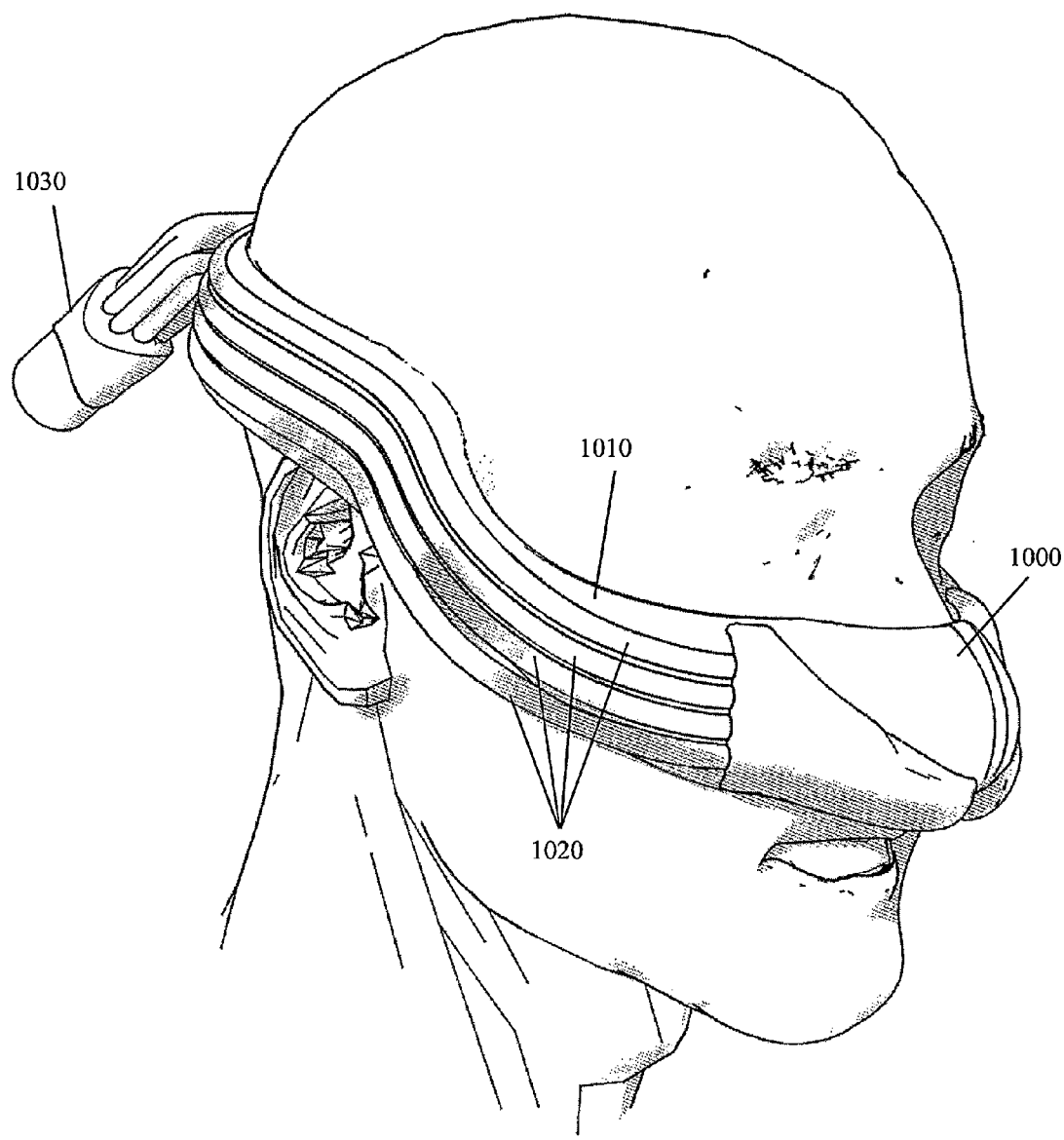
FIG. 10A is a perspective view of the front side of a sleep apnea mask, in accordance with a first embodiment of the present invention.
Figure 10B:
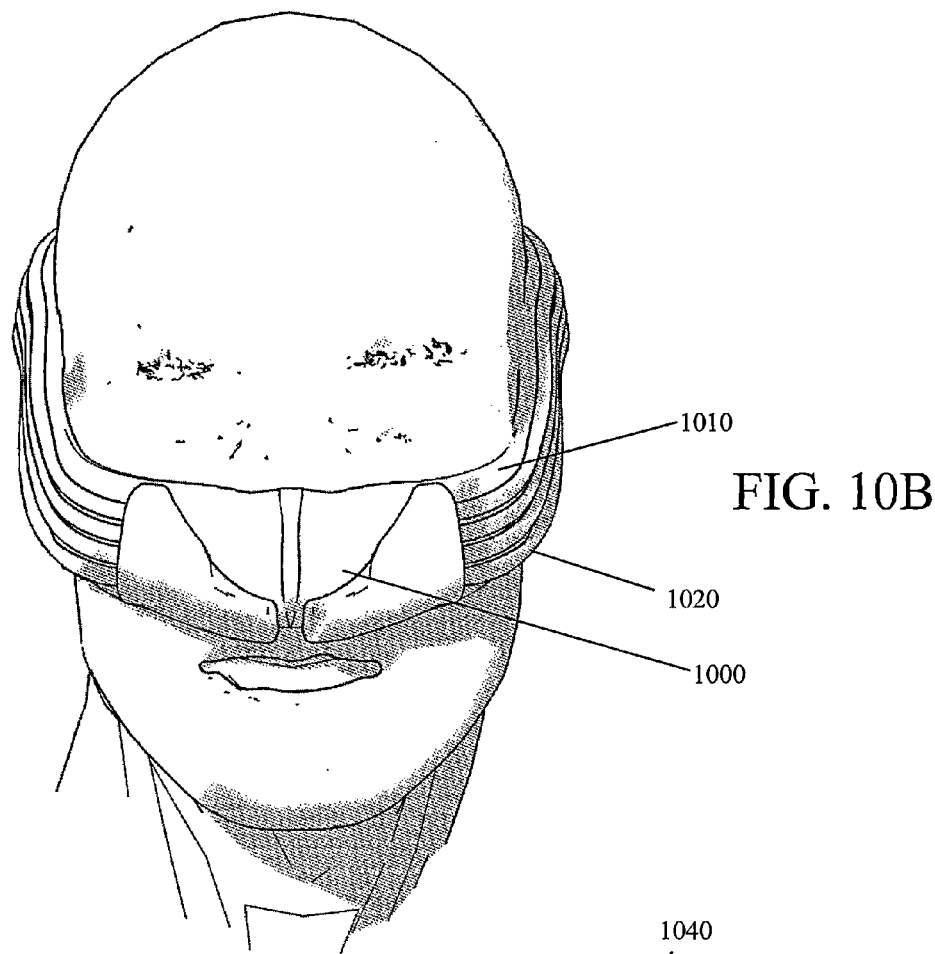
FIG. 10B is a front view of a sleep apnea mask, in accordance with a first embodiment of the present invention.
Figure 10C:
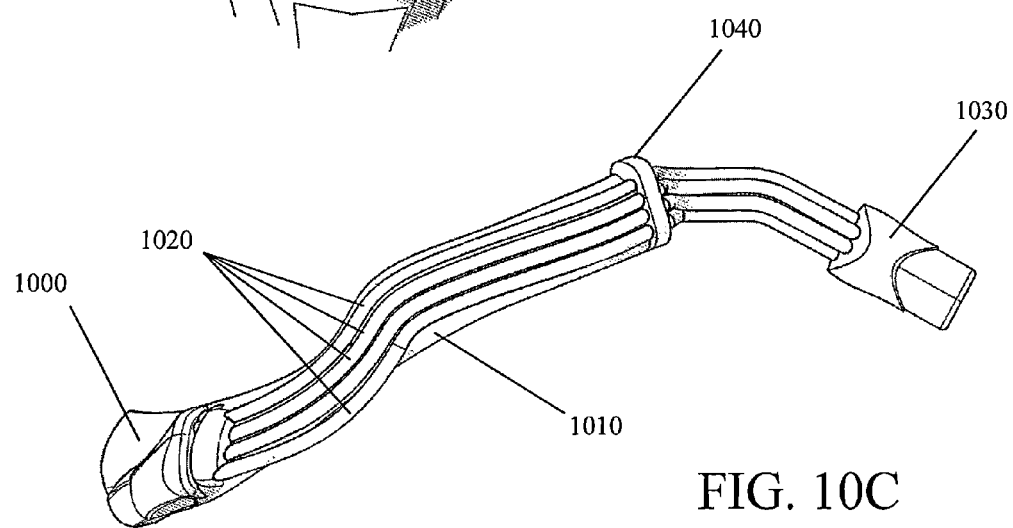
FIG. 10C is a side view of a sleep apnea mask, in accordance with a first embodiment of the present invention.

Illustrated in FIGS. 10A-10N is a first embodiment of a sleep apnea device including a face mask 1000 coinciding with the patient's nose, a headband 1010 for securing the mask to the face, and air ducts 1020 for channeling pressurized air from the CPAP machine to the mask. The face mask may further include a pair of nasal tubes that channel air directly to nose, as well as one or more manifolds 1002 or connectors to couple the air ducts to the nasal tubes. The air ducts 1020 in the preferred embodiment are vinyl or polycarbonate tubes that run from the back of the head, along one or both sides of the face, and to face mask. The polycarbonate tubes may diverge from the back of the head where they operably connect to a single coupling configured to detachably attach to the output tube of the CPAP machine. The multi-tube coupling 1030 may be referred to herein as a "spider coupling" shown in more detail in FIGS. 17A-17D. In the preferred embodiment, the air ducts are affixed to the outer face of the headband using retainers 1040 such as tines, clips, or channels into which the silicon tubes are seated or otherwise affixed. The headband 1010 is generally made of flexible material like silicone where it contacts the patient's skin. Left and rights sides of the headband may be configured to clip or otherwise attach at the back of the patient's head using a fastener including a clasp, clip, button, strap, or magnet, for example.

In accordance with the present invention, the inner face 1060 of the face mask and inner face of the headband are designed to conform to the patient's face, i.e, the mask and headband are made compliant with the patient. In addition, the size and spacing of the pair of nasal tubes is tailored specifically to the patient for whom the mask is intended. Since the mask is designed based on the patient's scan data, the mask and headband are custom tailored for the patient. In general, no two masks can be the same.

The portion of the mask that coincides with the patient's face preferably includes a rigid portion and flexible portion that makes contact with the patient's face. The flexible portion in contact with the patient's face may consist of a bio-safe elastomeric such as silicone or rubber, for example. The rigid portion of the mask may comprise or consist of a plastic capable of being built up in a layer-wise fashion using one or more rapid prototyping systems or computer-aided manufacturing systems including, for example, those techniques discussed herein. In the exploded views shown in FIGS. 10J and 10K, the facial portion of the mask includes a base plate and left and right manifolds 1002 shown in FIGS. 10L through 10N. Each manifold is a substantially enclosed cavity or compartment including (1) a plurality of input holes 1004 configured to receive one end of each polycarbonate tube 1020, and (2) an output hole 1006 that channels air into one of the nasal tubes. Each manifold in configured to snap into and friction fit onto the base plate.

Like the mask, the inner face 1060 of the left and right portions of the headband 1010 may consist of a flexible material including silicone or other elastomeric material that is comfortable against the patient's skin.

Figure 10D:
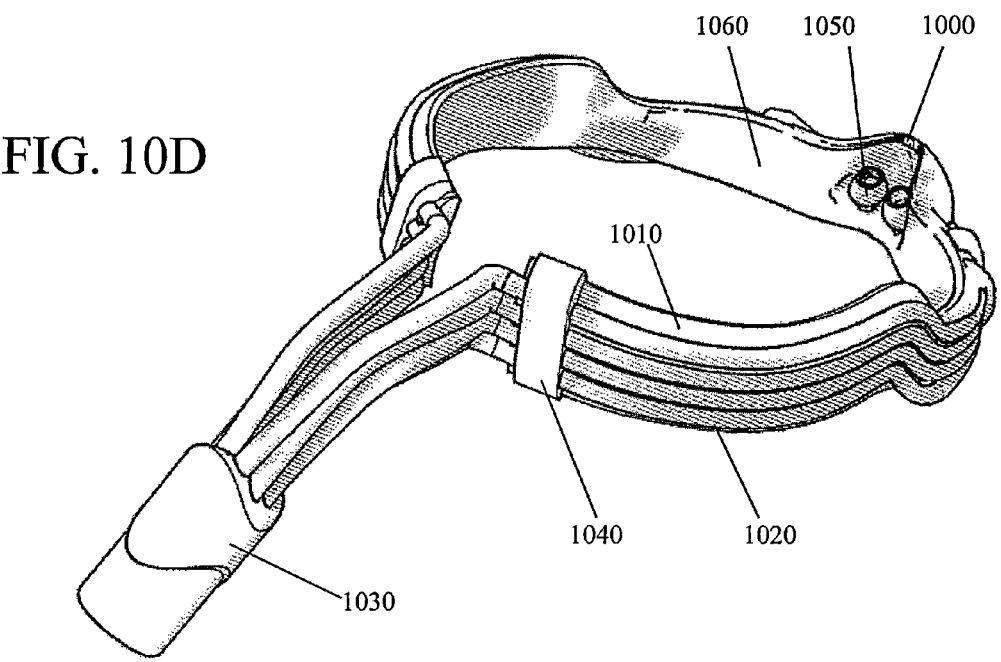
FIG. 10D is a perspective view of the back side of a sleep apnea mask, in accordance with a first embodiment of the present invention.
Figure 10E:
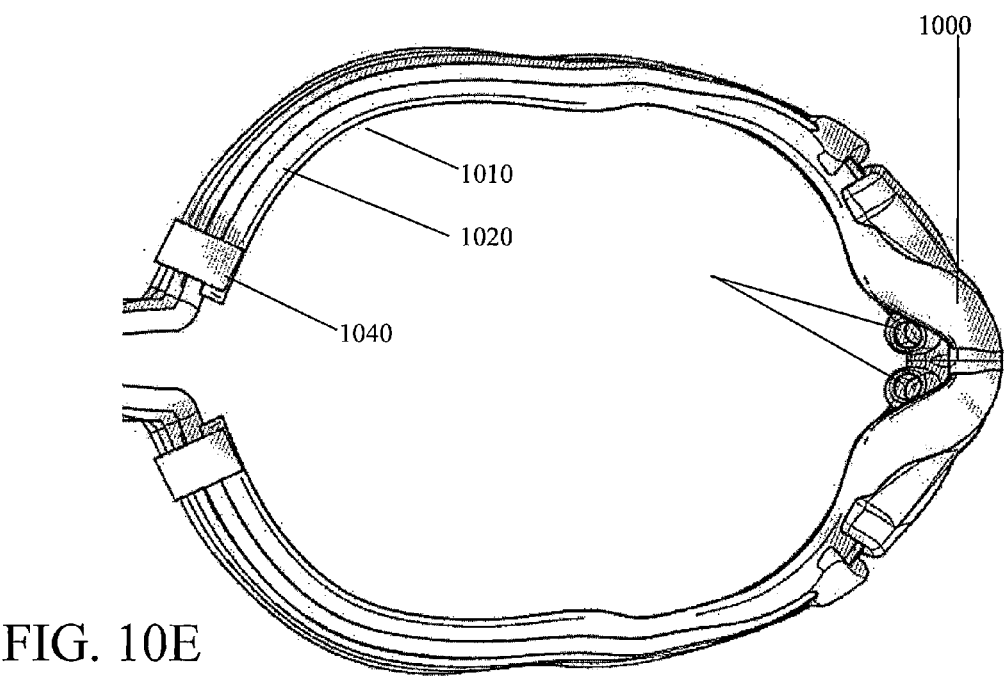
FIG. 10E is a top view of a sleep apnea mask, in accordance with a first embodiment of the present invention.
Figure 10J:
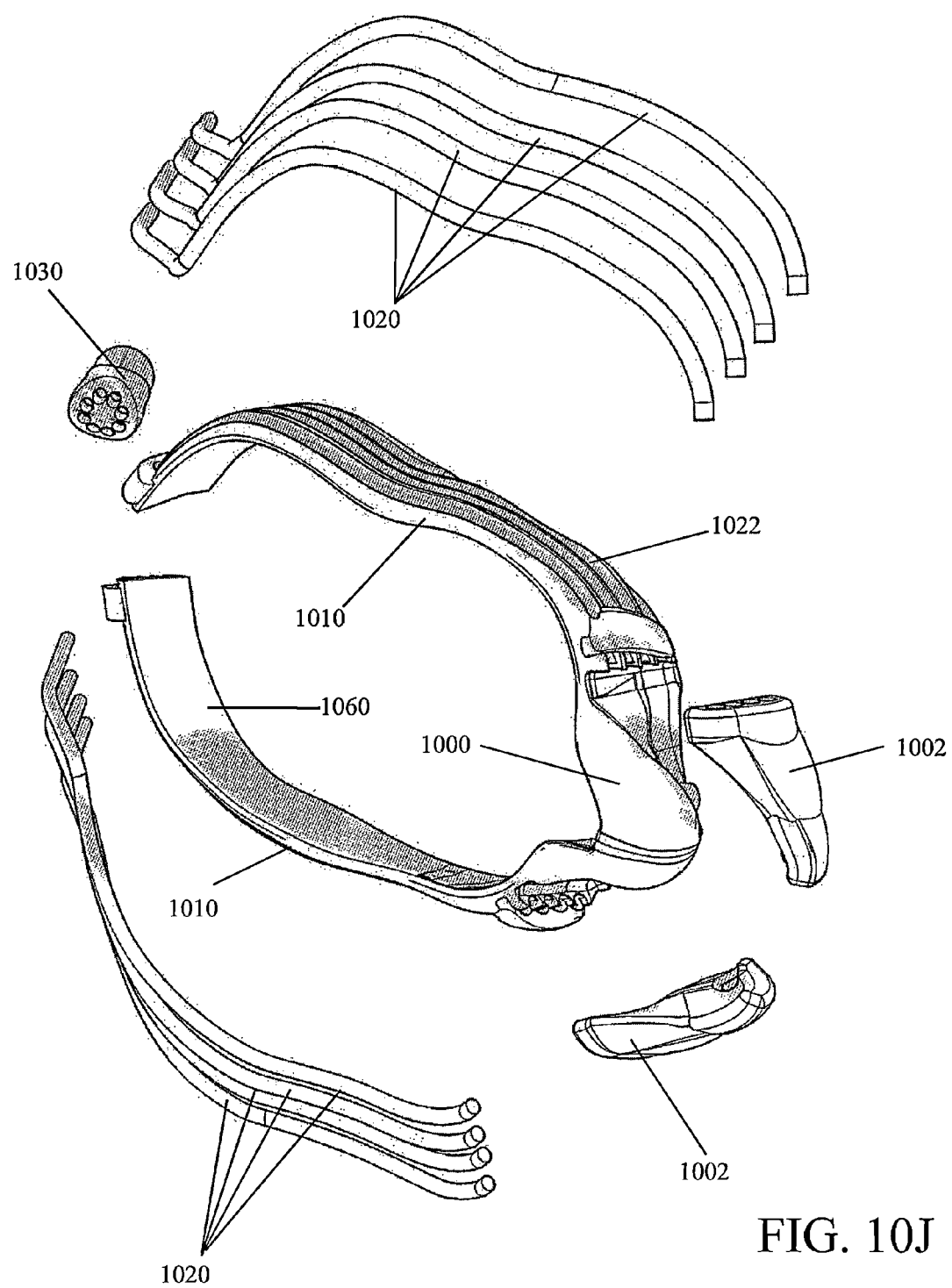
FIG. 10J is an exploded view of a sleep apnea mask, in accordance with a first embodiment of the present invention.
Figure 10K:
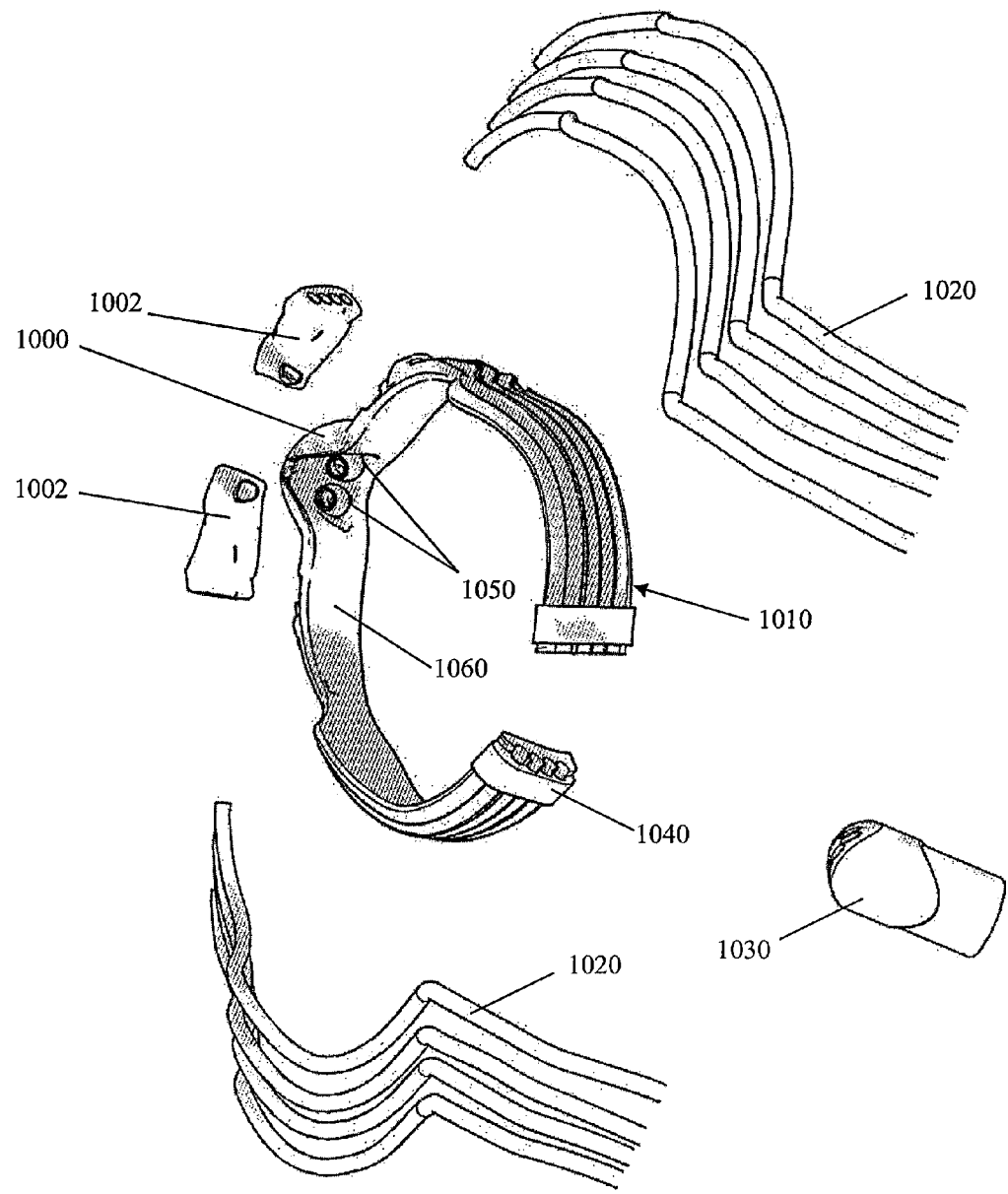
FIG. 10K is an exploded view of a sleep apnea mask, in accordance with a first embodiment of the present invention.
Figures 11A, 11B:
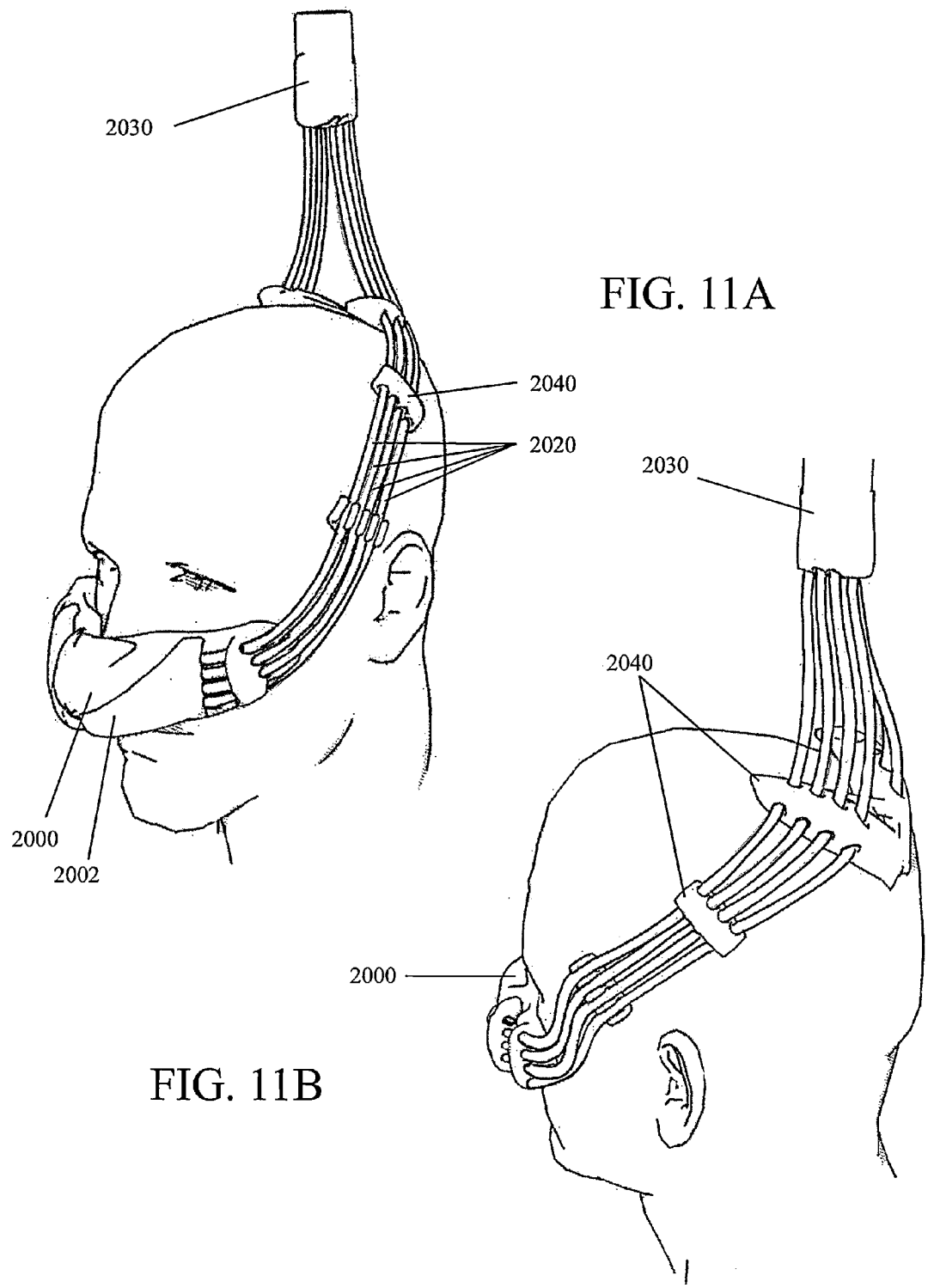
FIG. 11A is a perspective view of the front side of a sleep apnea mask, in accordance with a second embodiment of the present invention.
FIG. 11B is a perspective view of the back side of a sleep apnea mask, in accordance with a second embodiment of the present invention.
Figure 11C:
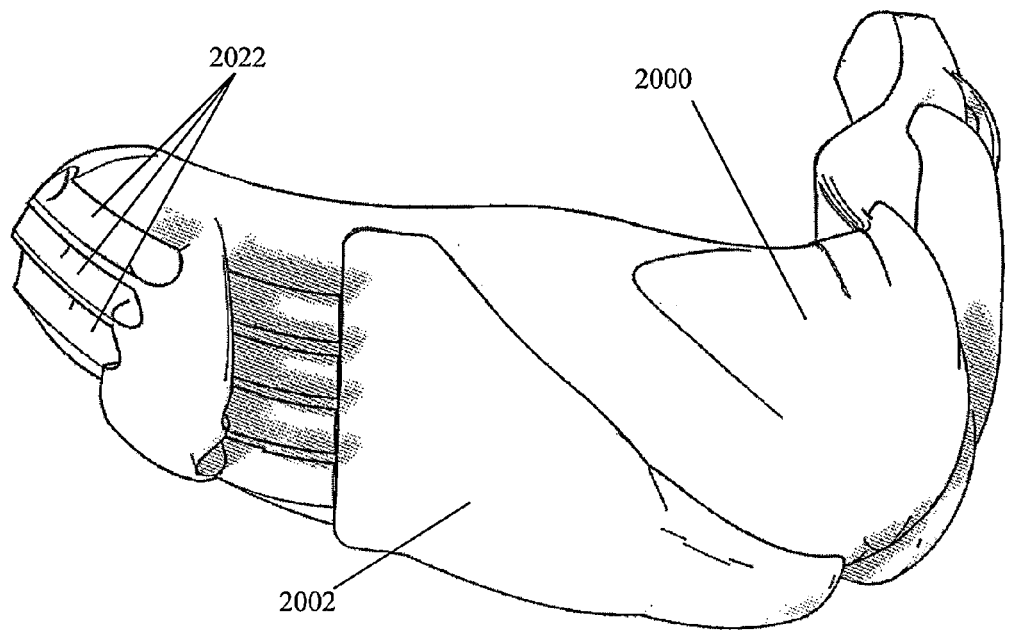
FIG. 11C is a perspective view of the front side of a sleep apnea mask, in accordance with a second embodiment of the present invention.
Figure 11D:
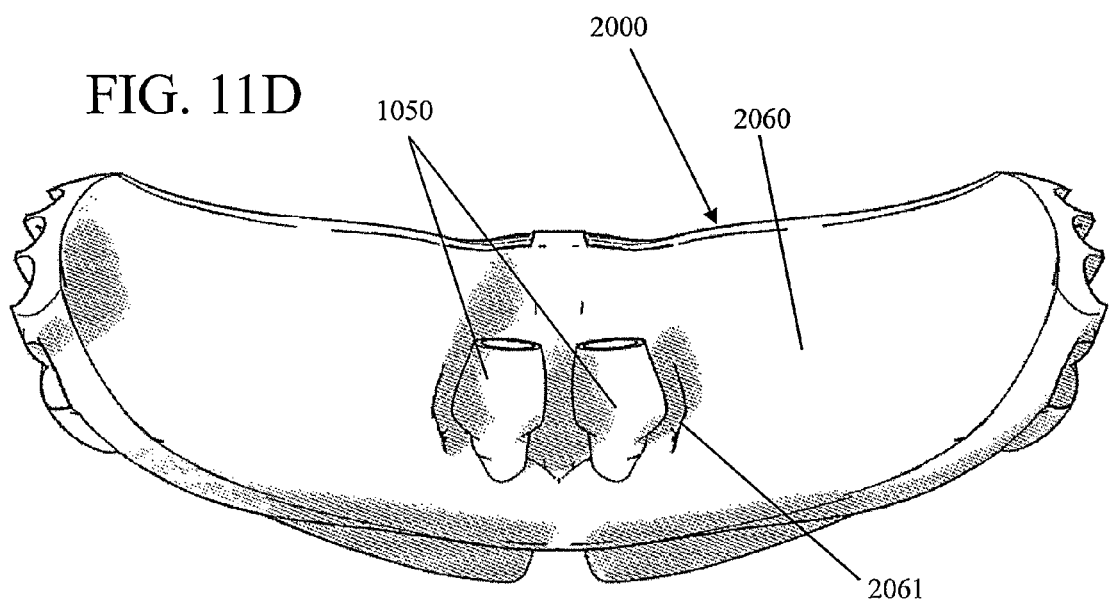
FIG. 11D is a view of the inner side of the face mask of a sleep apnea mask, in accordance with a second embodiment of the present invention.

Referring to FIG. 10D, the mask includes nasal tubes 1050 that are configured to extend a short distance into the patient's nose. The nasal tubes are shown in lateral cross section in FIG. 10F and in vertical cross section in FIG. 10G. In the preferred embodiment, the nasal tubes are formed from an elastomeric material. When positive air pressure is applied to the mask, the nasal tubes may expand slightly within the nose to better conform to the patient's nose and maintain the pressure induced by the CPAP machine.

Referring to FIG. 10G, the mask in some embodiments includes a plurality of magnets 1070 configured to apply a biasing force to hold the mask in place. As shown, magnets may be embedded in a location outside the nose as well as a location inside the nasal tube to generate a gentle pinching force that helps to secure the mask in place on the patient's face. In the preferred embodiment, the cavities configured to receive the magnets and/or ferrous material are included in the model of the mask and the magnets/ferrous material inserted after production of the mask.

In a second embodiment illustrated in FIGS. 11A through 11F, the sleep apnea mask uses the polycarbonate tubes 2020 to secure the face mask 2000 to the patient's head without an underlying band or strap. As discussed above, the face mask includes a base plate 2060 with a conformal inner surface, nasal tubes 1050, and manifolds 2002 coupled to the polycarbonate tubes. The inner surface of the base plate 2060 includes a recess configured to conform to the patient's nose. Unlike the previous embodiment, the tubes that make up the air duct attached to a plurality of retainers 2040 with channels into which the tubes seat. The first retainer 2044 in FIG. 11F receives a plurality of tubes from the CPAP coupling 2030 and bifurcates them to the left and right sides of the patient's face using guide holes 2046. A second and third set of retainers 2040 hold the tubes side-by-side in channels 2042 as the tubes traverse the patient cheek to the face mask. The face mask 2000 includes additional channels 2022 into which the tubes seat, thus serving as a fourth set of retainers. The location of the mask on the face depends on the length of the tubes between the face mask and the first retainer. To adjust the placement of the face mask, the patient need only retract the tubes from the first retainer or further insert the tubes into the first retainer.

Figure 12A:
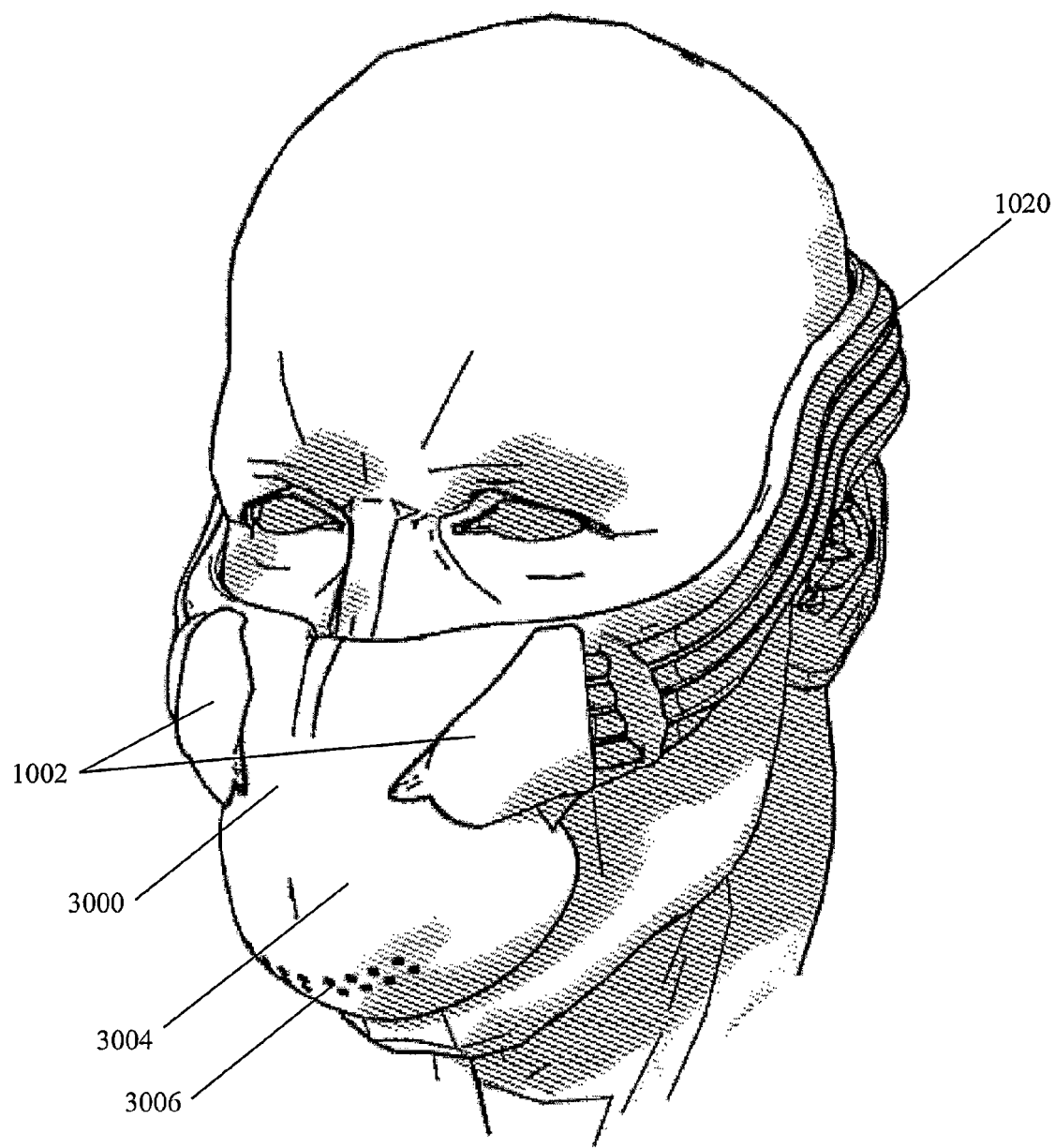
FIG. 12A is a perspective view of a sleep apnea mask, in accordance with a third embodiment of the present invention.
Figure 12B:
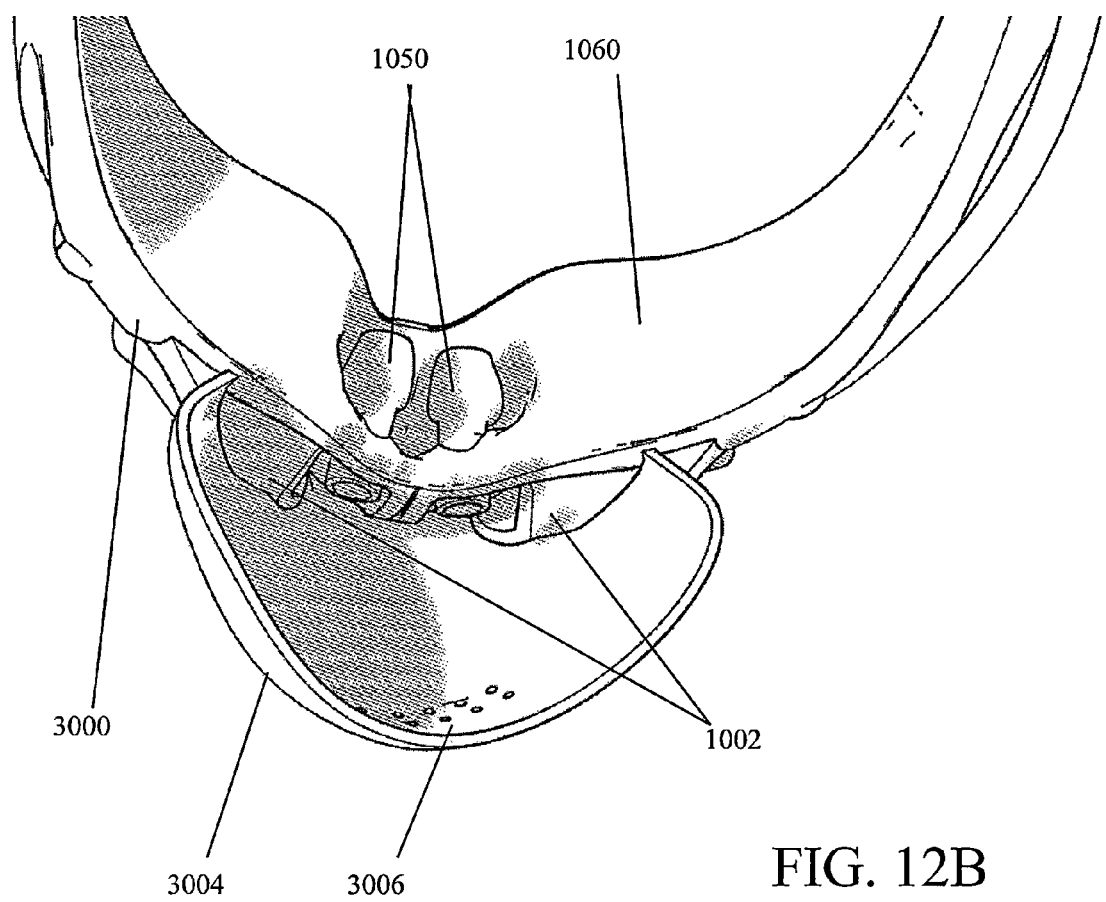
FIG. 12B is a perspective view of the inner side of the face mask of a sleep apnea mask, in accordance with a third embodiment of the present invention.

In a third embodiment illustrated in FIGS. 12A through 12B, the sleep apnea mask 3000 is substantially similar to the mask 1000 of the first embodiment with the inclusion of an enclosure 3004 that covers a portion of the nose and mouth. In this embodiment, the manifold (not shown) outputs air into both the nasal tubes 1050 as well as the inside of the enclosure 3004 covering the mouth, thereby better maintaining pressure in the patient's respiratory system. The enclosure, however, does include vent holes 3006 enable air to readily escape if the patient should sneeze. Like the first embodiment above, the third embodiment of the mask further includes a headband for securing the mask to the face and external air ducts for channeling pressurized air from the CPAP machine to the mask.

Figure 13A:
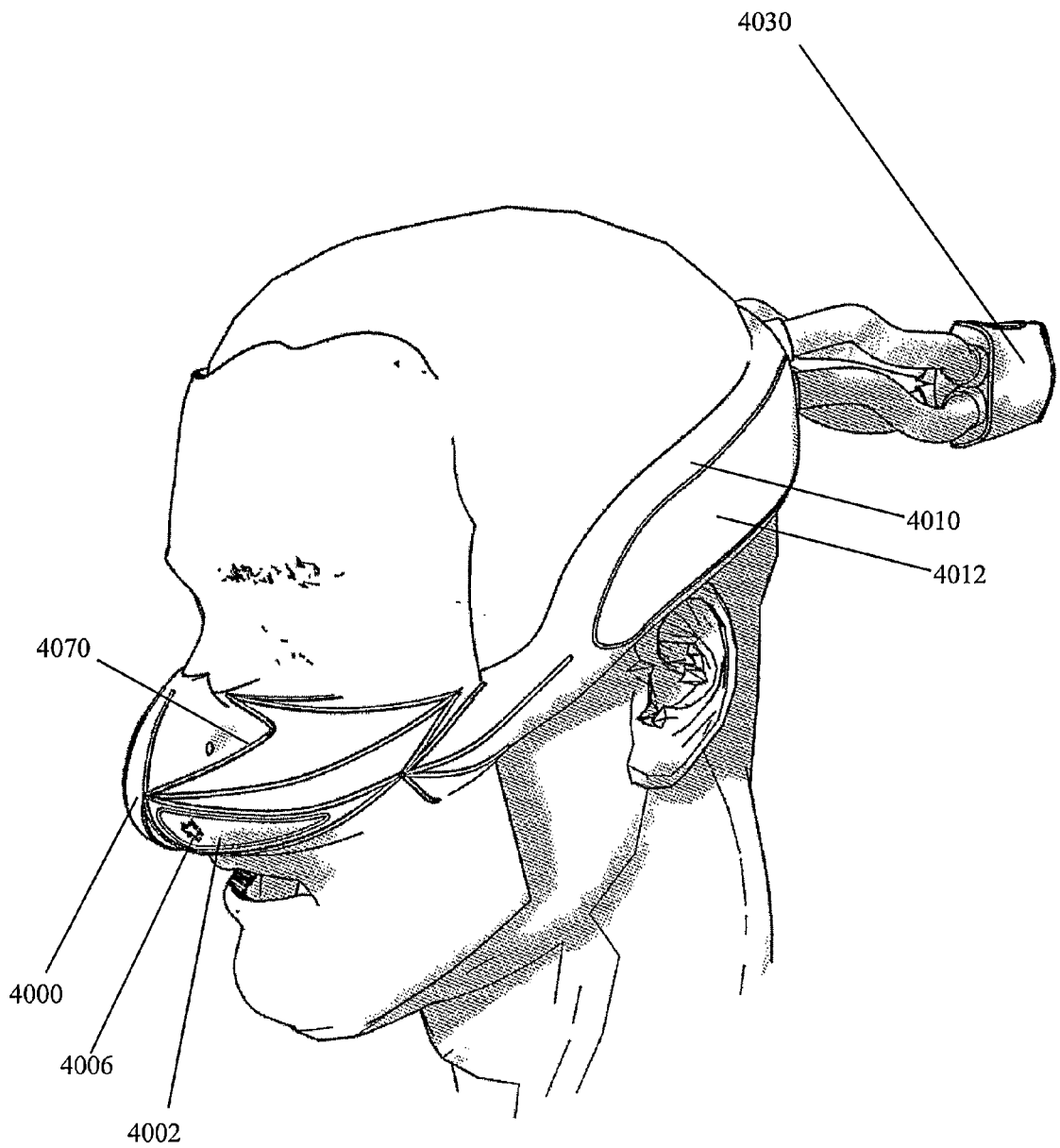
FIG. 13A is a perspective view of a sleep apnea mask, in accordance with a fourth embodiment of the present invention.
Figure 13B:
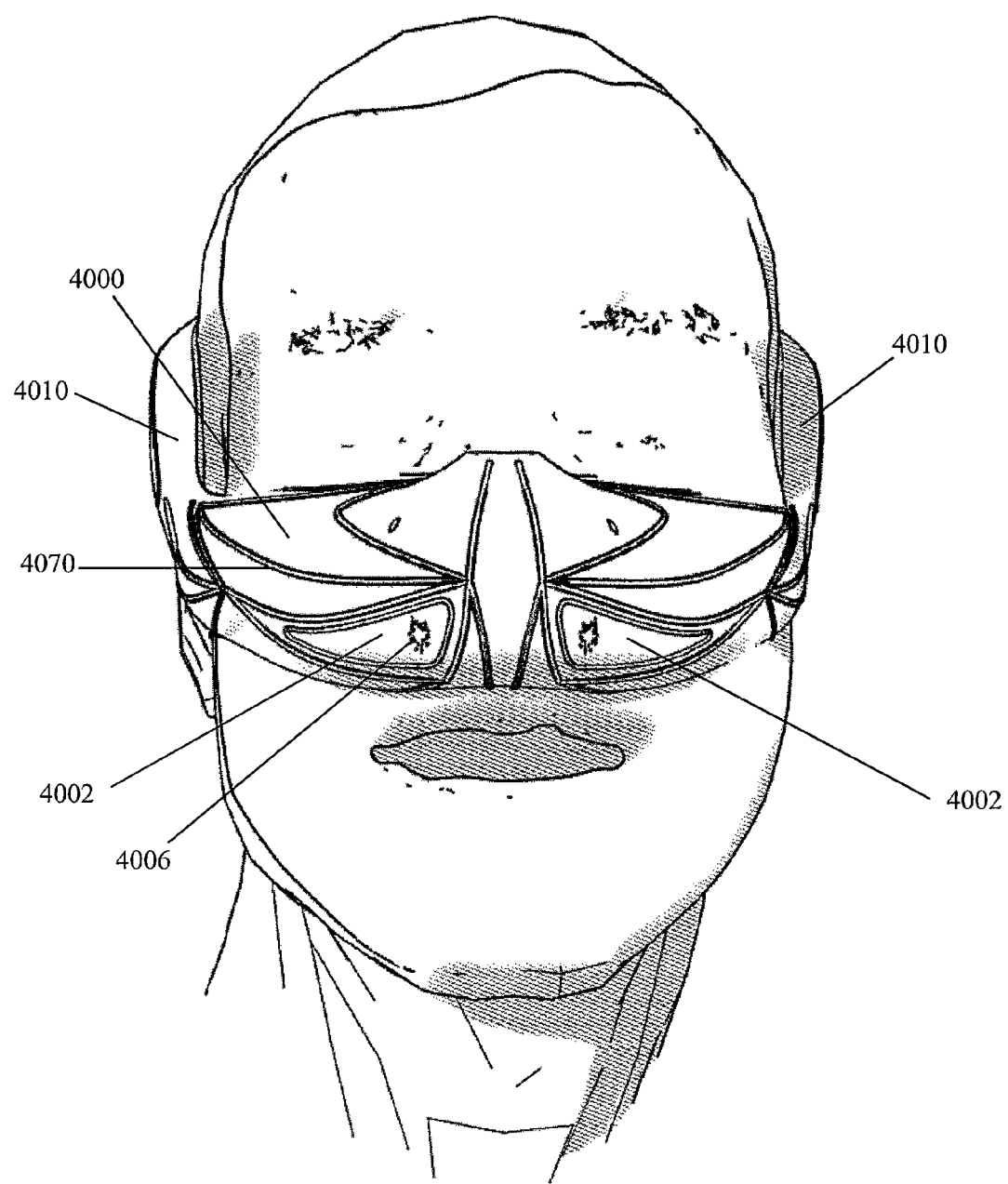
FIG. 13B is a front side view of a sleep apnea mask, in accordance with a fourth embodiment of the present invention.
Figure 13D:
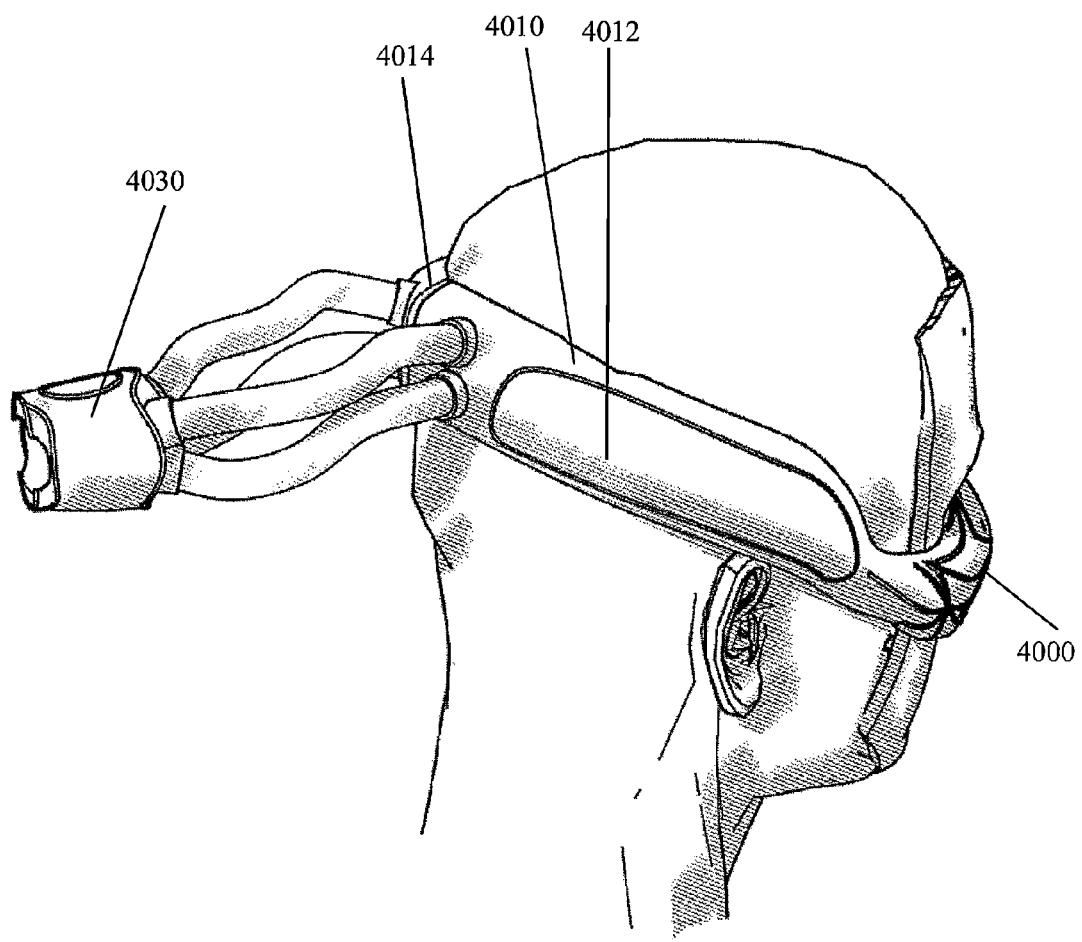
FIG. 13D is a back side view of a sleep apnea mask, in accordance with a fourth embodiment of the present invention.
Figure 13H:
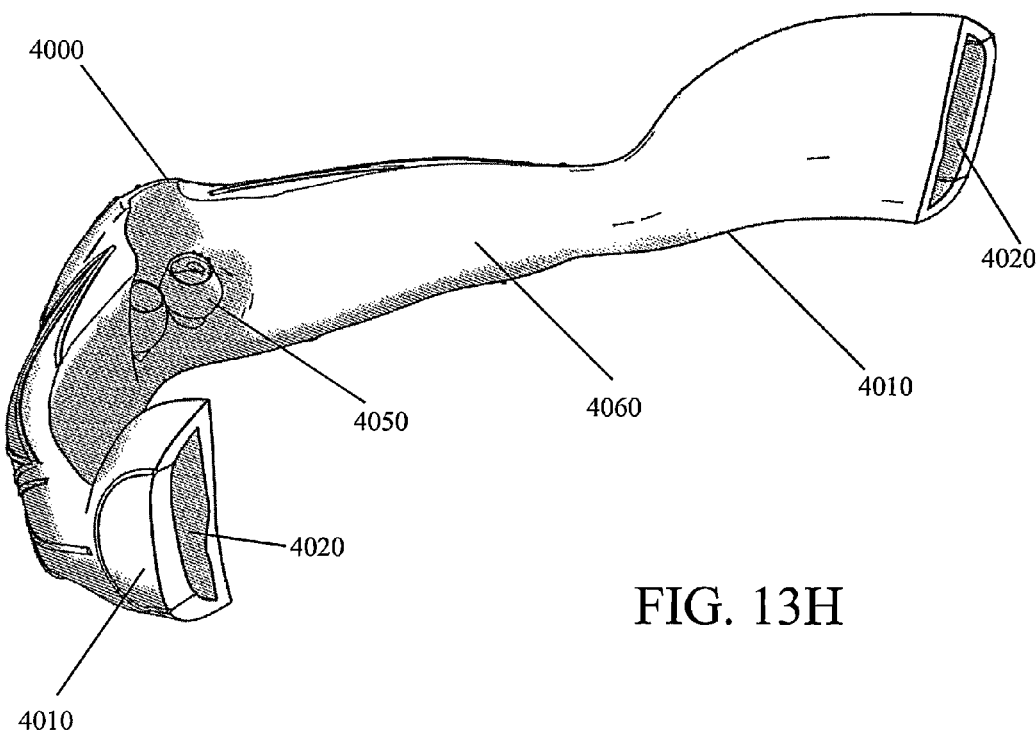
FIG. 13H is a cross sectional view of a sleep apnea mask, in accordance with a fourth embodiment of the present invention.
Figure 13I:
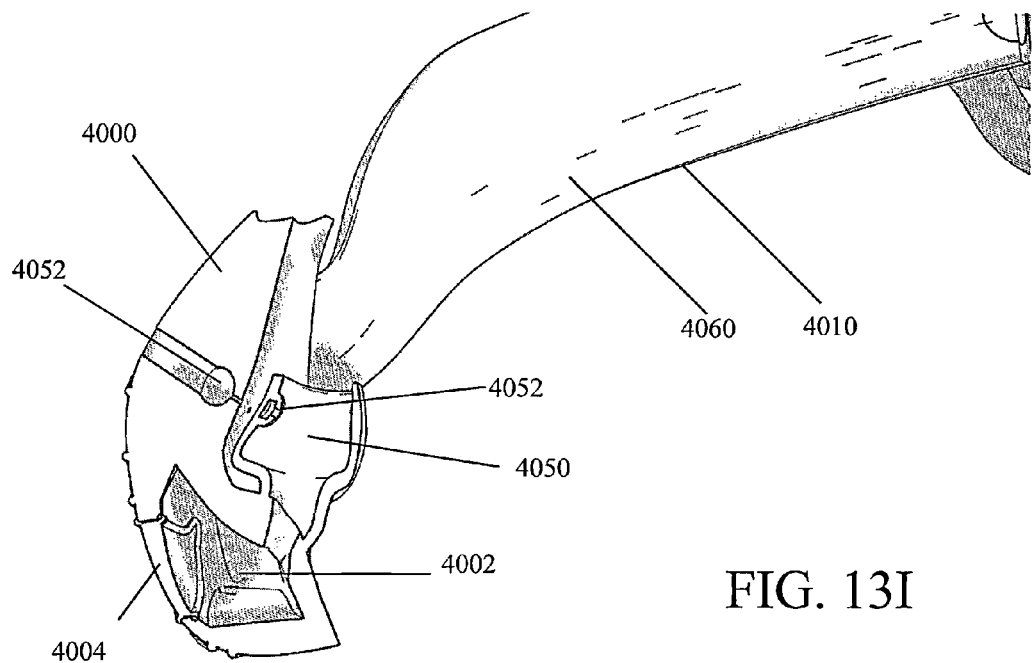
FIG. 13I is a cross sectional view of a sleep apnea mask, in accordance with a fourth embodiment of the present invention.
Figure 13J:
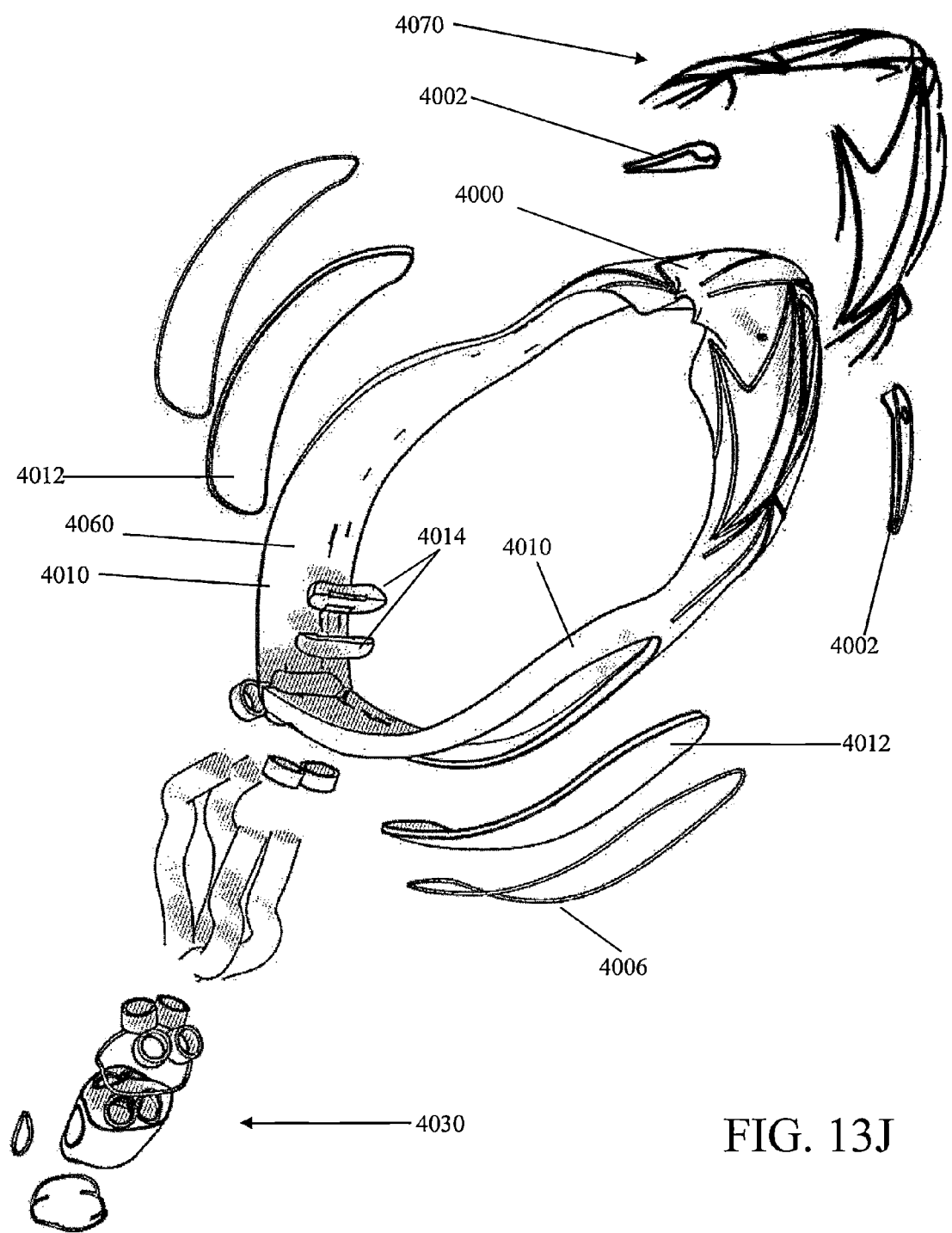
FIG. 13J is an exploded view of a sleep apnea mask, in accordance with a fourth embodiment of the present invention.
Figure 14A:
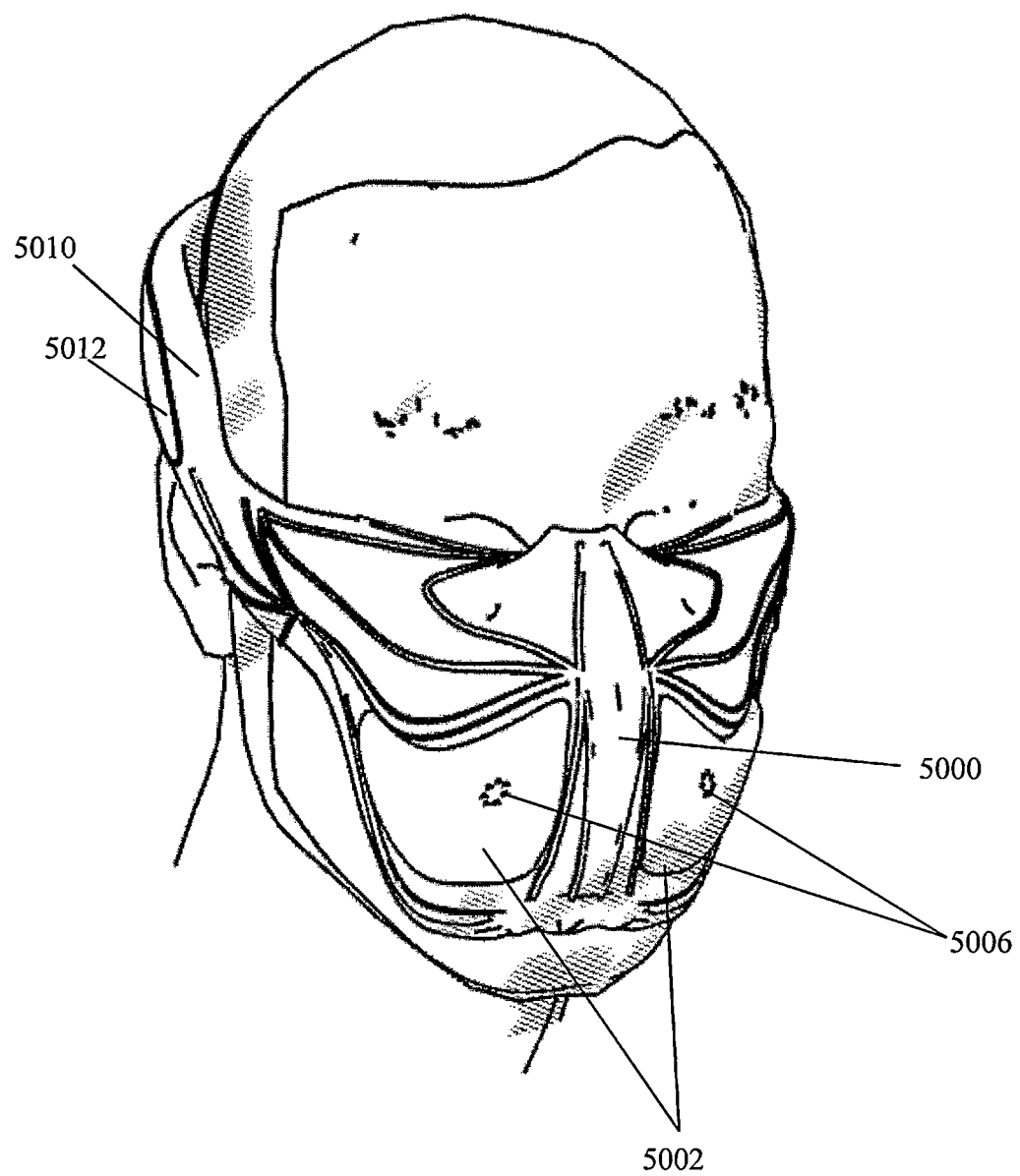
FIG. 14A is a perspective view of a sleep apnea mask, in accordance with a fifth embodiment of the present invention.
Figure 14B:
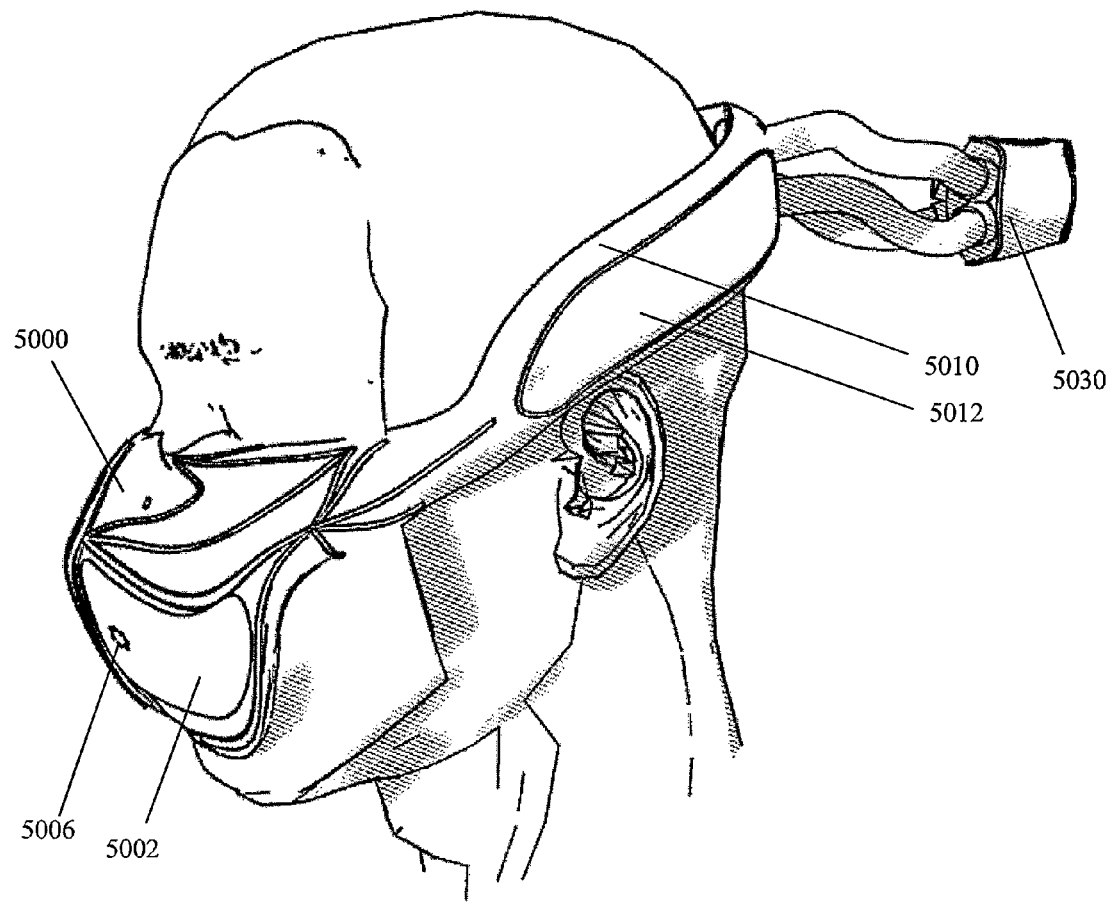
FIG. 14B is a side view of a sleep apnea mask, in accordance with a fifth embodiment of the present invention.
Figure 14C:
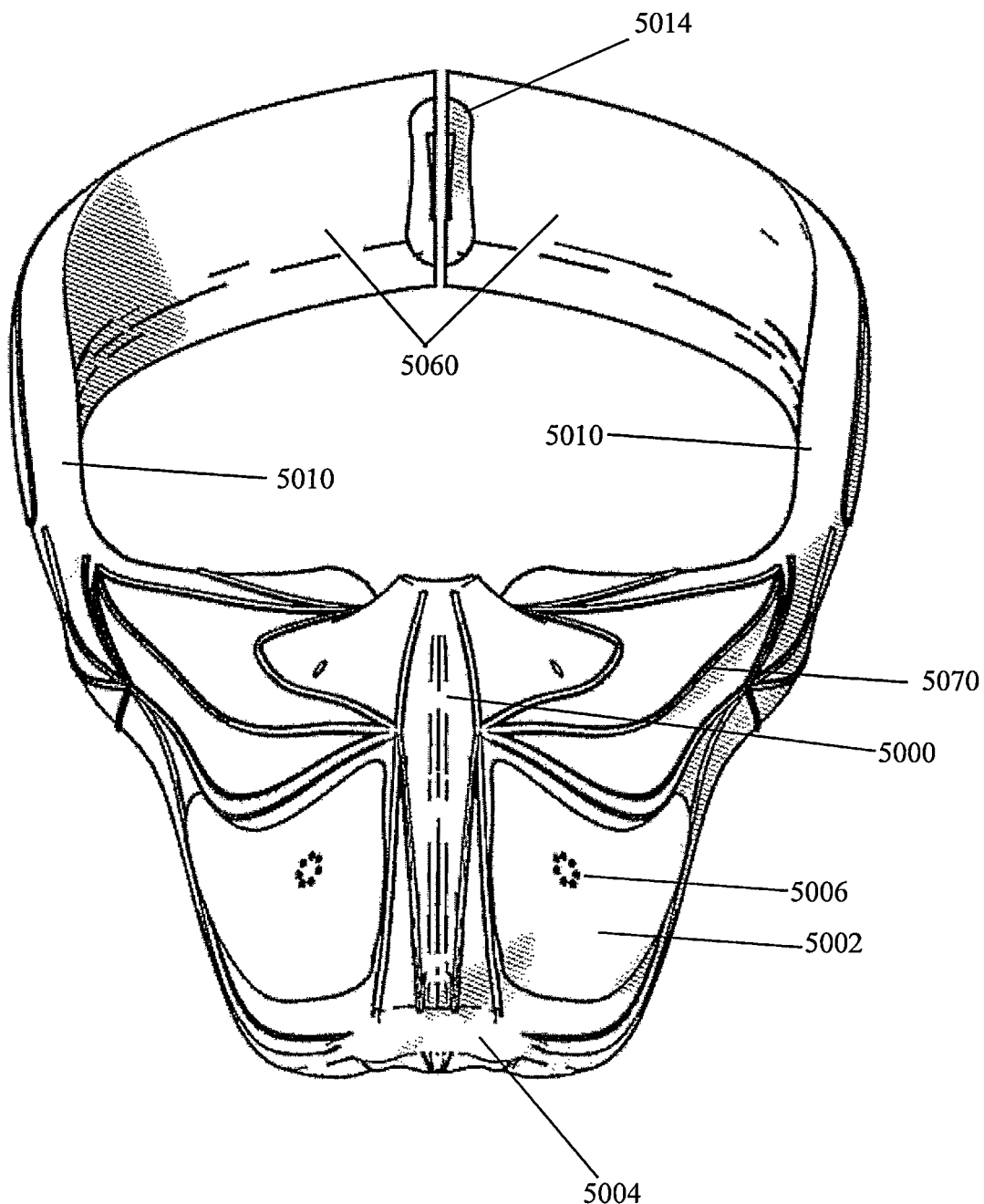
FIG. 14C is a front side view of a sleep apnea mask, in accordance with a fifth embodiment of the present invention.
Figure 14D:
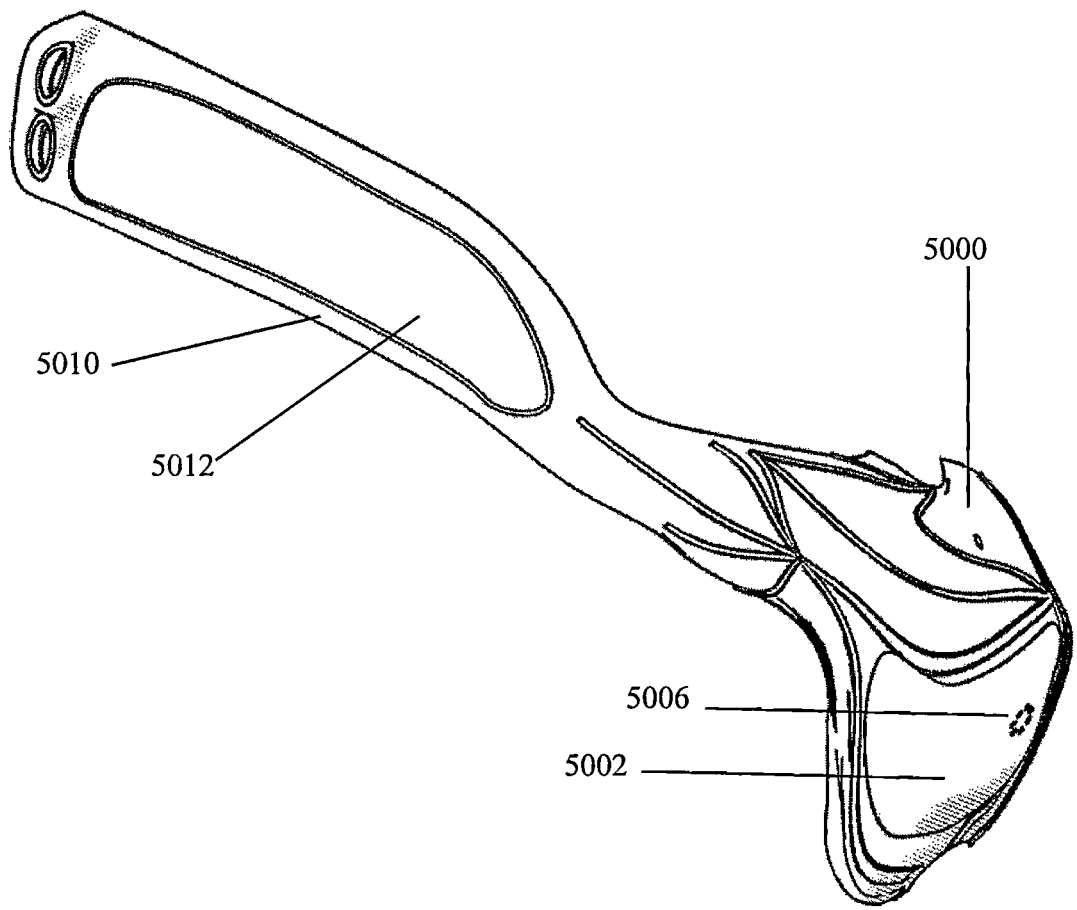
FIG. 14D is a side view of a sleep apnea mask, in accordance with a fifth embodiment of the present invention.
Figure 14E:
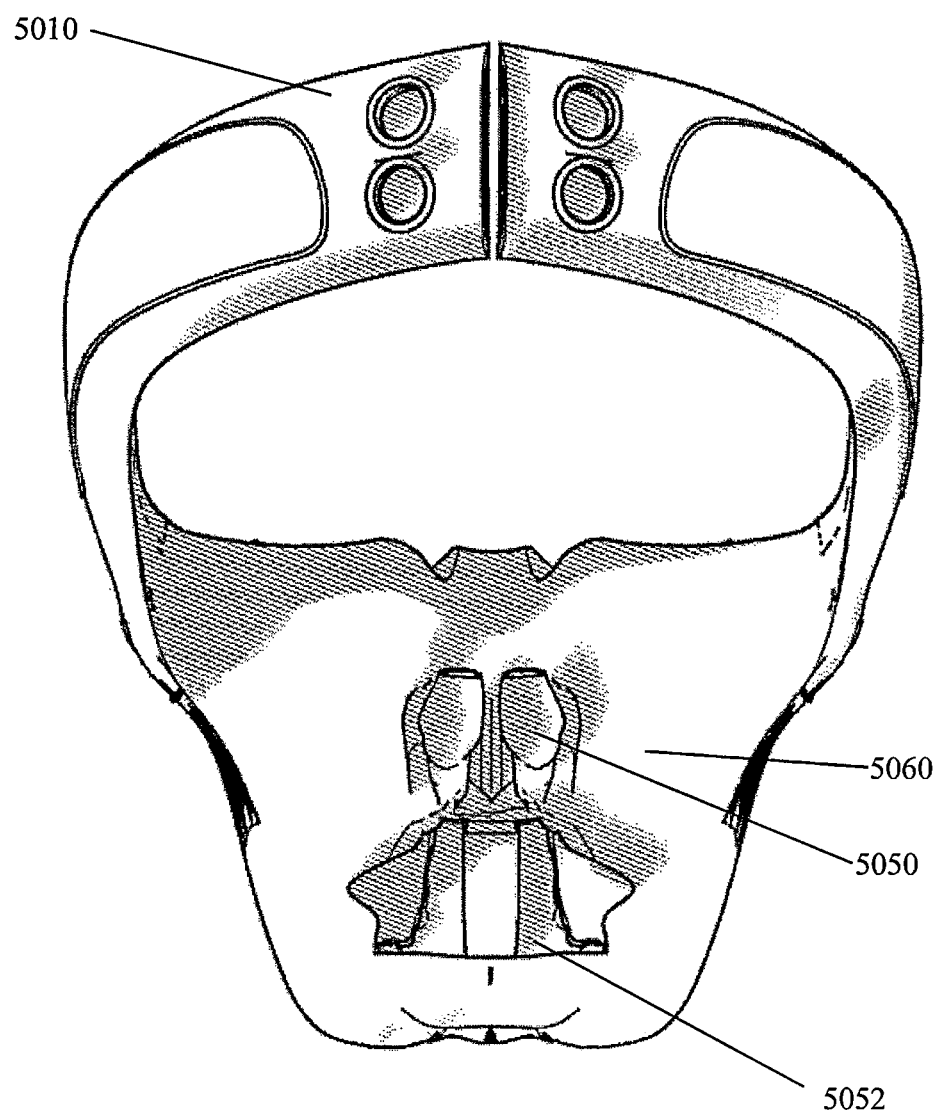
FIG. 14E is a back side view of a sleep apnea mask, in accordance with a fifth embodiment of the present invention.
Figure 14F:
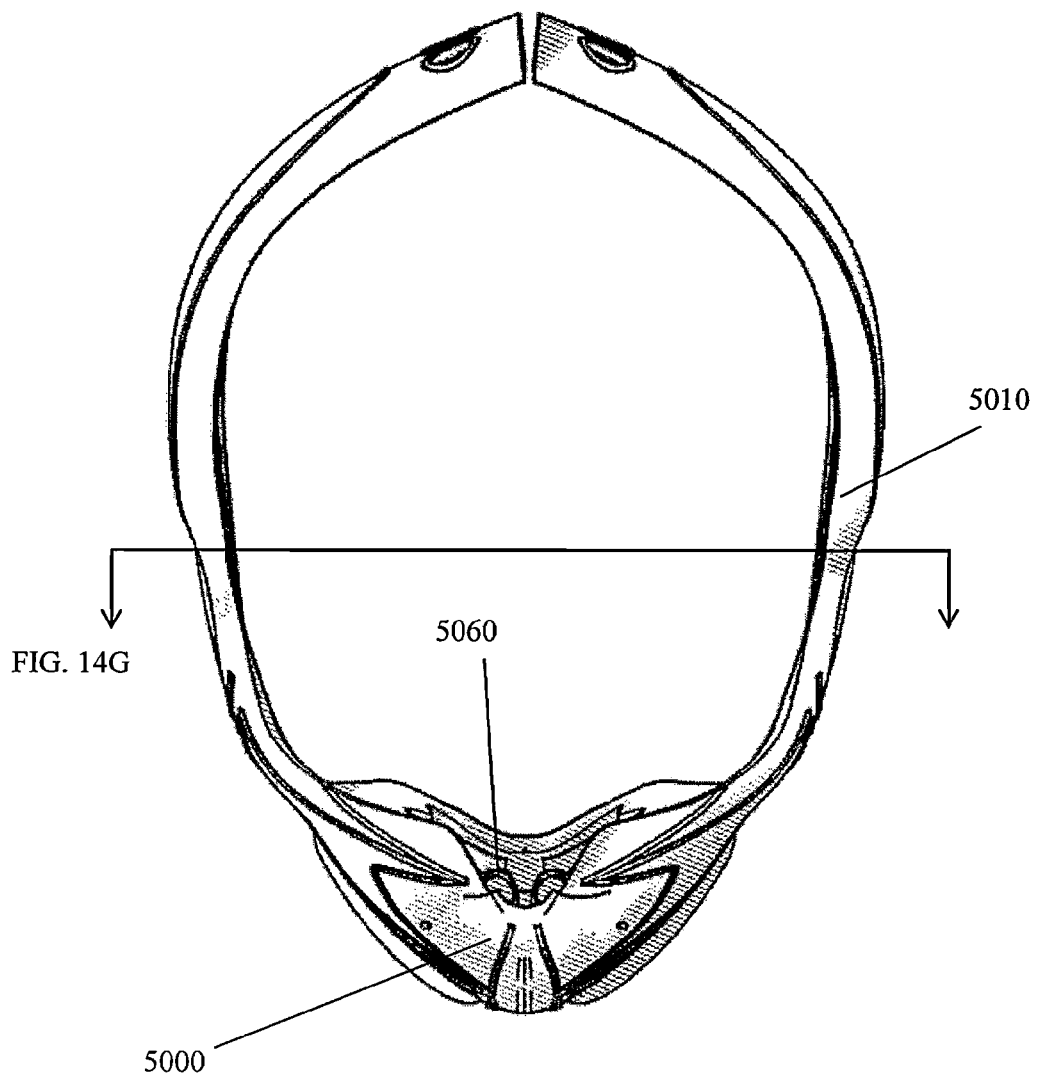
FIG. 14F is a top side view of a sleep apnea mask, in accordance with a fifth embodiment of the present invention.
Figure 14G:
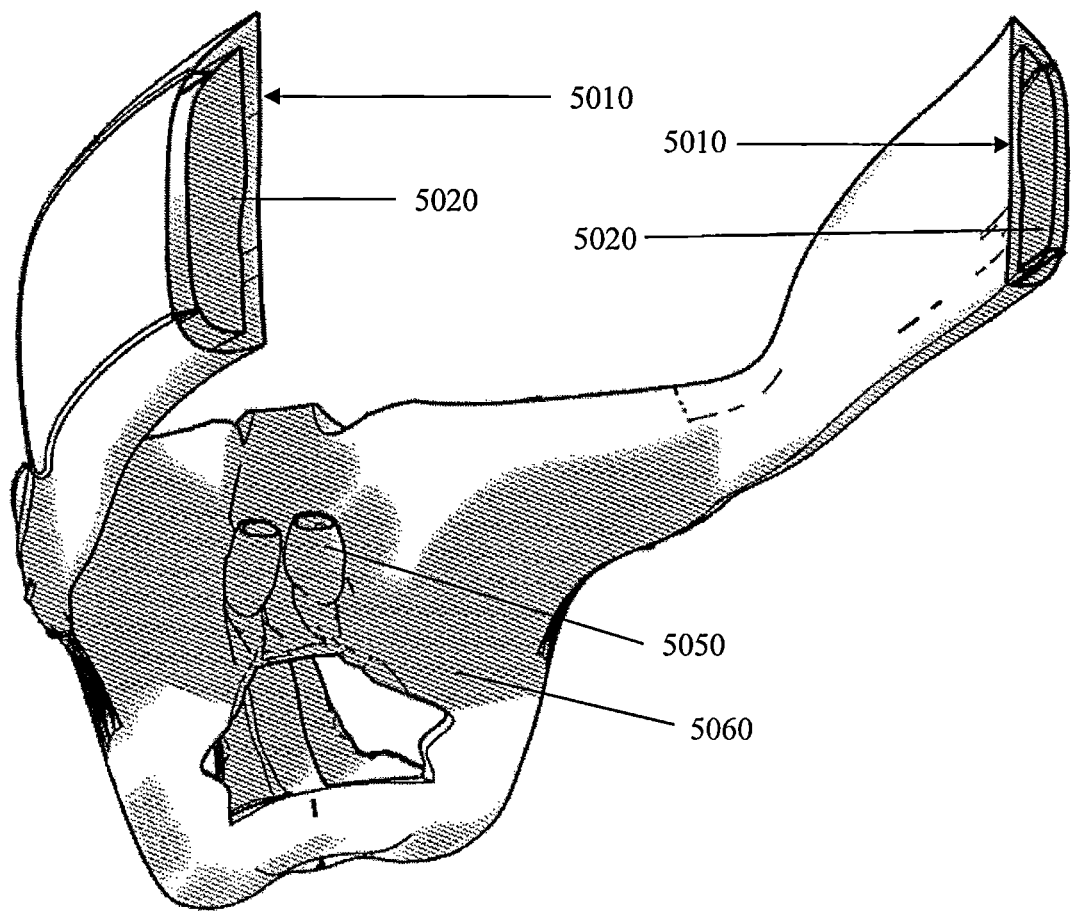
FIG. 14G is a cross sectional view of a sleep apnea mask, in accordance with a fifth embodiment of the present invention.
Figure 14H:
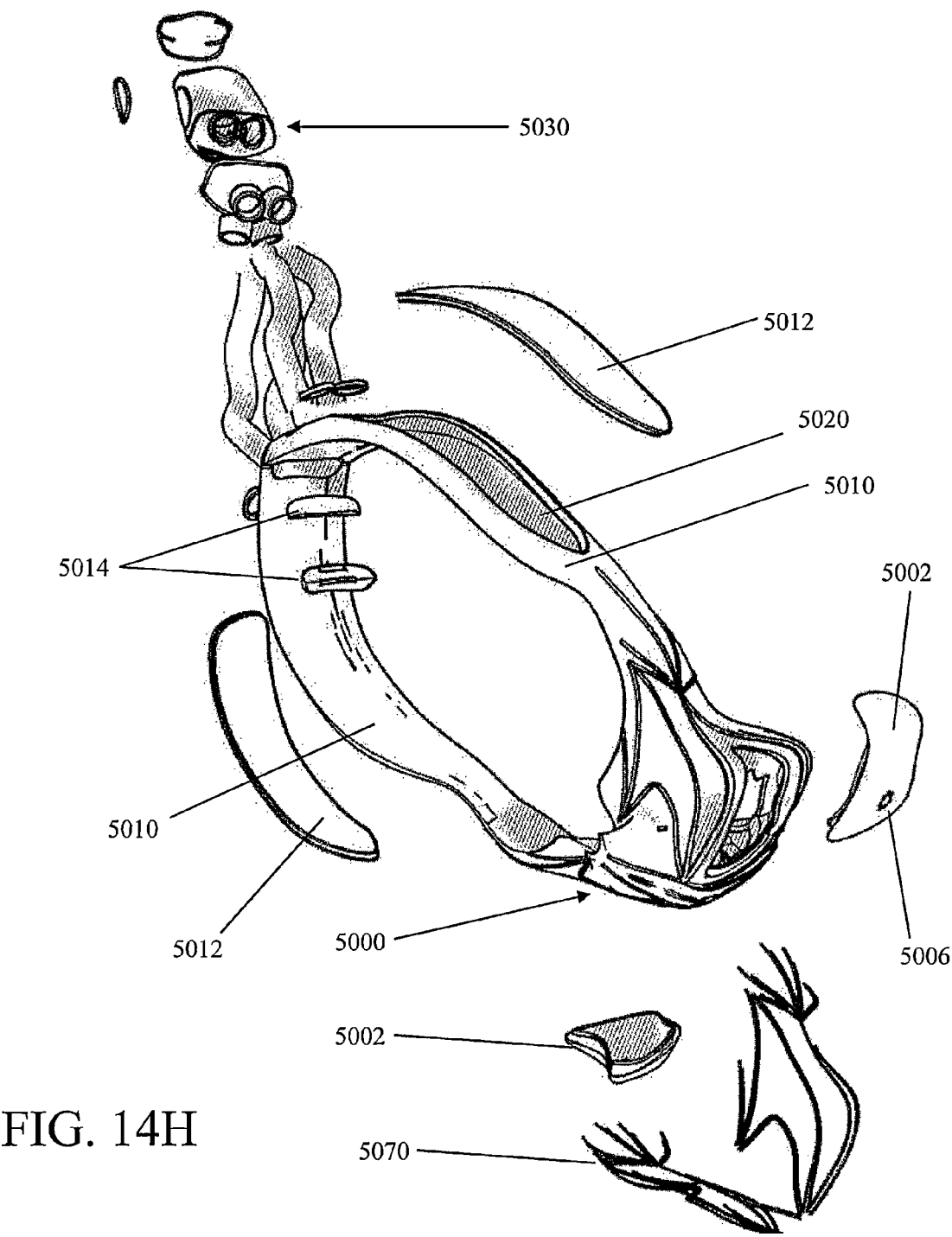
FIG. 14H is an exploded view of a sleep apnea mask, in accordance with a fifth embodiment of the present invention.
Figure 15A:
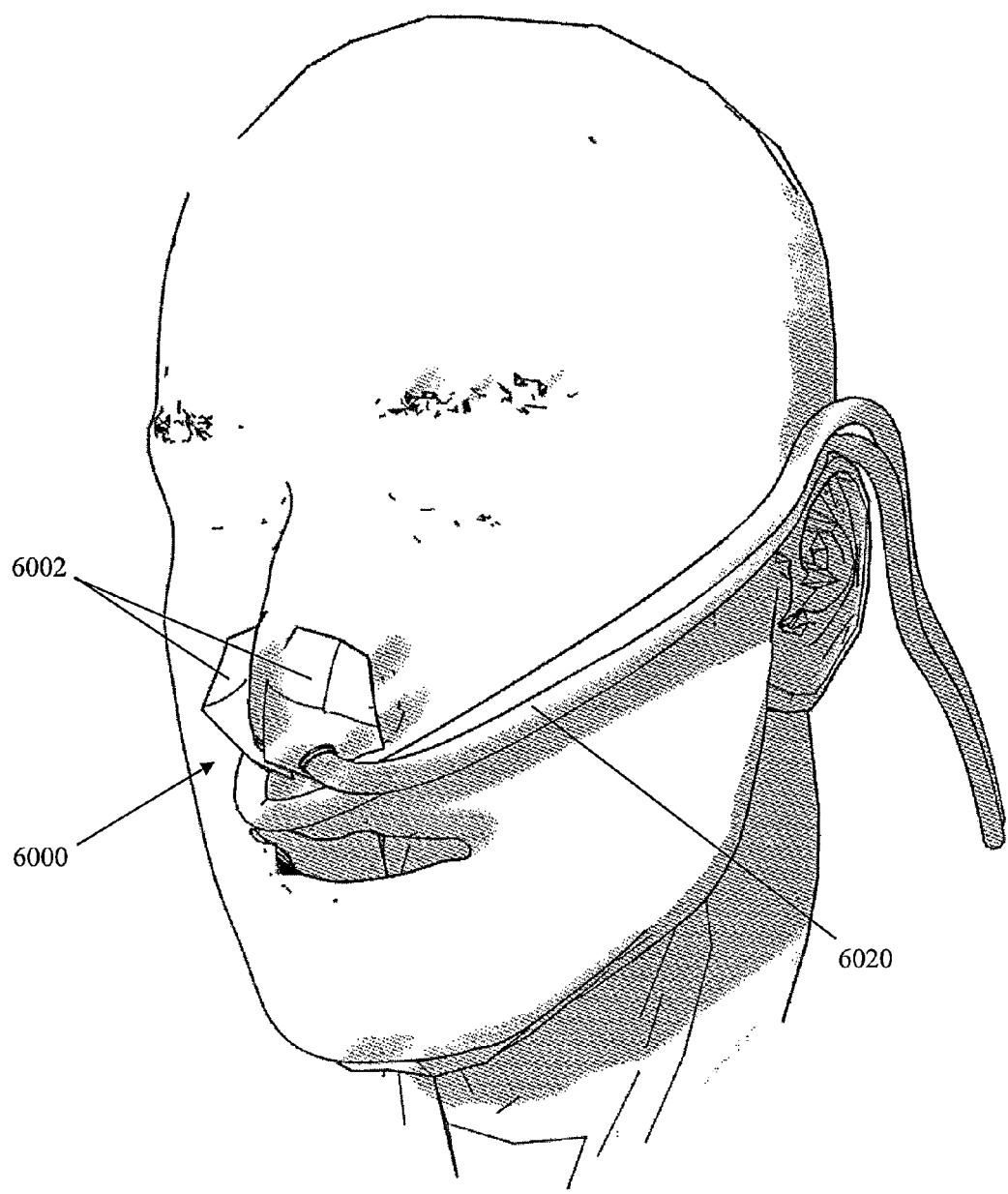
FIG. 15A is a perspective view of a sleep apnea mask, in accordance with a sixth embodiment of the present invention.
Figure 15B:
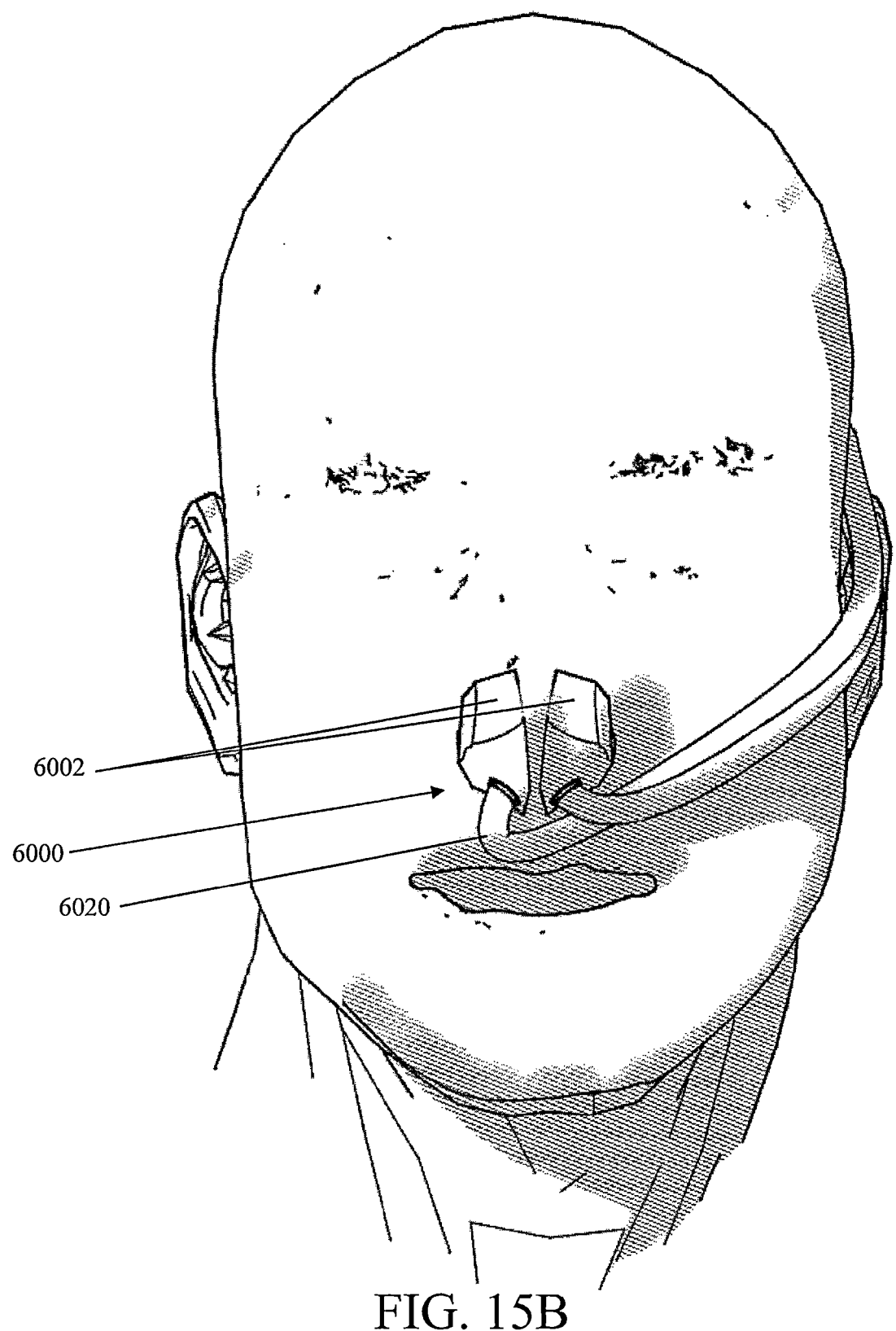
FIG. 15B is a front side view of a sleep apnea mask, in accordance with a sixth embodiment of the present invention.

Illustrated in FIGS. 13A through 13J is a fourth embodiment of a sleep apnea device including a face mask 4000 coinciding with the patient's nose, a headband 4010, and one or more air ducts 4020 for channeling pressurized air from the CPAP machine to the mask. A coupling 4030 with tubes conducts air from the CPAP machine to the air ducts of the headband. The coupling 4030 is shown in more detail in FIGS. 17A-17D. The air ducts 4020, which are embedded internally within the headband 4010, run from the back of the head, along one or both sides of the face, and to nasal tubes 4050 in the face mask. A cross section of the air ducts is shown in FIG. 13H, and a cross section of the face mask and cavity shown in FIG. 13I. The cavity is created in the space between an enclosure 4004 and the base plate 4060. The enclosure includes a plurality of panels 4002 that snap in and frictionally fit to the enclosure. Similarly, the left and right portions of the headband 4010 include caps or panels 4012 that snap in and frictionally fit to the headband. The caps or panels 4002 and 4012 provide access to the air ducts and cavity for purposes of removing support material that was deposited in the cavity during the manufacturing process.

The nasal tubes 4050 may include a cavity into which a magnet 4052 is inserted. A corresponding cavity and magnet 4052 are built into the enclosure in a position in proximity to the nasal tubes 4050.

The headband 4010 is generally made of flexible material where it contacts the patient's skin. Left and rights sides of the headband may be configured to fasten at the back of the patient's head using a fastener 4014, clip, strap, or magnet, for example.

In accordance with the present invention, the inner face 4060 of the face mask and inner face of the headband are designed to conform to the patient's face, i.e., the mask and headband are made compliant with the patient. Since the sleep apnea device is designed based on the patient's scan data, the mask and headband are custom tailored for the patient. The inner face of the mask and headband may consist of a flexible elastomeric material including silicone, for example. The outer portion of the mask and headband may consist of a plastic capable of being built up in a layer-wise fashion using one or more computer-aided manufacturing systems including, for example, those techniques discussed herein above.

In the preferred embodiment, the mask includes elastomeric webbing 4070 covering the front of the face mask and the perimeter of the openings that receive panels in the sides of the headband. The webbing provides additional structural integrity for the sleep apnea device, similar to the manner in which tendons or other structural members provide structural support in anatomical or architectural environments. The elastomeric webbing may be constructed in a layer-wise manner along with the rest of the mask. The webbing may be formed from any of a number of thermoset materials including hard and soft thermosets known to those skilled in the art.

In a fifth embodiment illustrated in FIG. 14A through 14H, the sleep apnea mask 5000 is substantially similar to the fourth embodiment with the inclusion of an enclosure that covers both the nose and mouth. In this embodiment, the internal chamber 5052 connects the air ducts 5020 with both nasal tubes 5050 as well as an opening to the mouth, thereby better distributing the pressure from the CPAP machine to the patient's respiratory system. Like the fourth embodiment, the mask and headband 5010 includes panels 5002, 5012 that detachably attach by means of a friction fit in order to remove support material that accumulates during the manufacturing process. The fastener 5014 at the back of the headband as well as the CPAP coupling 5030 are similar to those shown in the fourth embodiment discussed above. The inner face 5060 of the mask and headband are configured to conform to the face of the patients as determined by the patient's face scan data.

The face mask configured to cover the nose and mouth may further include a sneeze inhibition mechanism to prevent injury or discomfort should the patient sneeze while wearing the mask. In the preferred embodiment, the mechanism consists of a plurality of holes or vias 5006 configured to expel air from the front of the face mask. In other embodiments, the sneeze inhibition mechanism includes a pressure-sensitive valve that releases air from the mask when the pressure in the mask exceeds a predetermine threshold. The mask may further include elastomeric webbing 5070 covering the front of the face mask.

Illustrated in FIGS. 15A through 15E is a sixth embodiment of a sleep apnea device 6000 including a face mask and one or more air ducts 6020 for channeling pressurized air from the CPAP machine to the mask. The mask includes a left portion and a right portion 6002, each configured to attach to one side of the patient's nose. Both portions of the mask include nasal tubes 6050 with pairs of magnets configured to pull the nasal tube toward the outer portion of the mask. The mask further includes at least one air duct 6020 connected to a CPAP machine for distributing air to the left and right sides of the mask. Although the left and right portions are shown as separate components, these portions may be rigidly connected by means of one or more bridges (not shown) configured to traverse the patient's nose.

In accordance with the present invention, the inner face of the face mask is made compliant with the patient using the patient scan data, thereby yielding a mask custom tailored for the patient. The inner face of the mask may consist of a flexible material including silicone, for example. The outer portion of the mask may consist of a plastic capable of being built up in a layer-wise fashion using one or more computer-aided manufacturing systems including, for example, those techniques discussed herein.

In each of the six of the preferred embodiments above, the sleep apnea device connects to a CPAP machine using an elastic coupling. One version of an elastomeric CPAP coupling is shown in FIGS. 17A-17D. In the preferred embodiment, the coupling is a constructed from three elastomeric materials. The first elastomeric material, e.g., silicone, is configured to easily flex under pressure. The entire body of the coupling from the air ducts to the CPAP output tube is constructed from the first elastic material. The second elastomeric material is a structural material that prevents the first elastomeric material from ripping or tearing. The second elastomeric material is used to construct a webbing, shell, pattern that enables the coupling to flex while still holding pressure. The third elastomeric coupling forms a semi-rigid structure for contacting the inner surface of the CPAP output tube.

Illustrated in FIGS. 16A through 16G is a seventh embodiment of a sleep apnea device including a face mask 7000 with nasal tubes 7050 and one or more valves 7090 that regulate the flow of air out of the nasal tubes. The mask comprises left and right portions 7002 rigidly affixed to one another by means of a bridge 7080. In this embodiment, there is no CPAP or CPAP coupling. Instead, the values 7090 are configured to passively inhibit the flow of air in order to maintain positive pressure in the patient's lungs without any external CPAP input. In the preferred embodiment, the values comprise one-way values that readily admit air during inhalation while inhibiting the flow of air out of the nose when the patient exhales. In this manner, the sleep apnea device helps to maintain a higher volume of air in the patient's lungs than would be present without the sleep apnea device. The additional volume, in turn, helps to keep the patient's airways open and reduce the detrimental effects of sleep apnea.

In accordance with the present invention, the inside face 7060 of the mask is designed using the patient scan data so that it conforms to the patient's face, i.e, made compliant with the patient. The left and right mask portions may also be constructed from two or more materials including a silicone or other material that contacts the patient's face and a second more rigid material forming the body of the mask and nasal tubes.

The one-way valve 7090 in this embodiment includes a retainer 7096 and an insert 7092 residing in a cavity in a nasal tube. The insert 7092 is captured between the retainer 7096 and the inner wall of the nasal tube. The insert 7092 is permitted to move vertically a small distance within the confines of the cavity. The insert 7092 includes a plurality of apertures including a primary aperture 7093 and plurality of secondary apertures 7094. The primary aperture 7093 permits air to flow in and out of the valve with equal resistance in both directions. The secondary apertures 7094, in contrast, provide more resistance to the flow of air out of the nostril than the flow of air in the nostril. To accomplish this, the apertures are oriented at an angle such that the top of the aperture resides relatively close to the primary aperture while the bottom of the aperture resides relatively far from the primary aperture. When the patient inhales, the insert is forced by air pressure to the top of the cavity which allows air through both the primary and secondary apertures. When the patient exhales, the insert is forced by air pressure to the bottom of the cavity where the secondary apertures make contact with and get blocked by the retainer, thereby preventing the flow of air through the secondary apertures. Although air is still expelled through the primary aperture, the size and shape of the primary aperture is configured to provide resistance to maintain sufficient pressure in the patient's lungs between breaths.

Figures 16A, 16B:
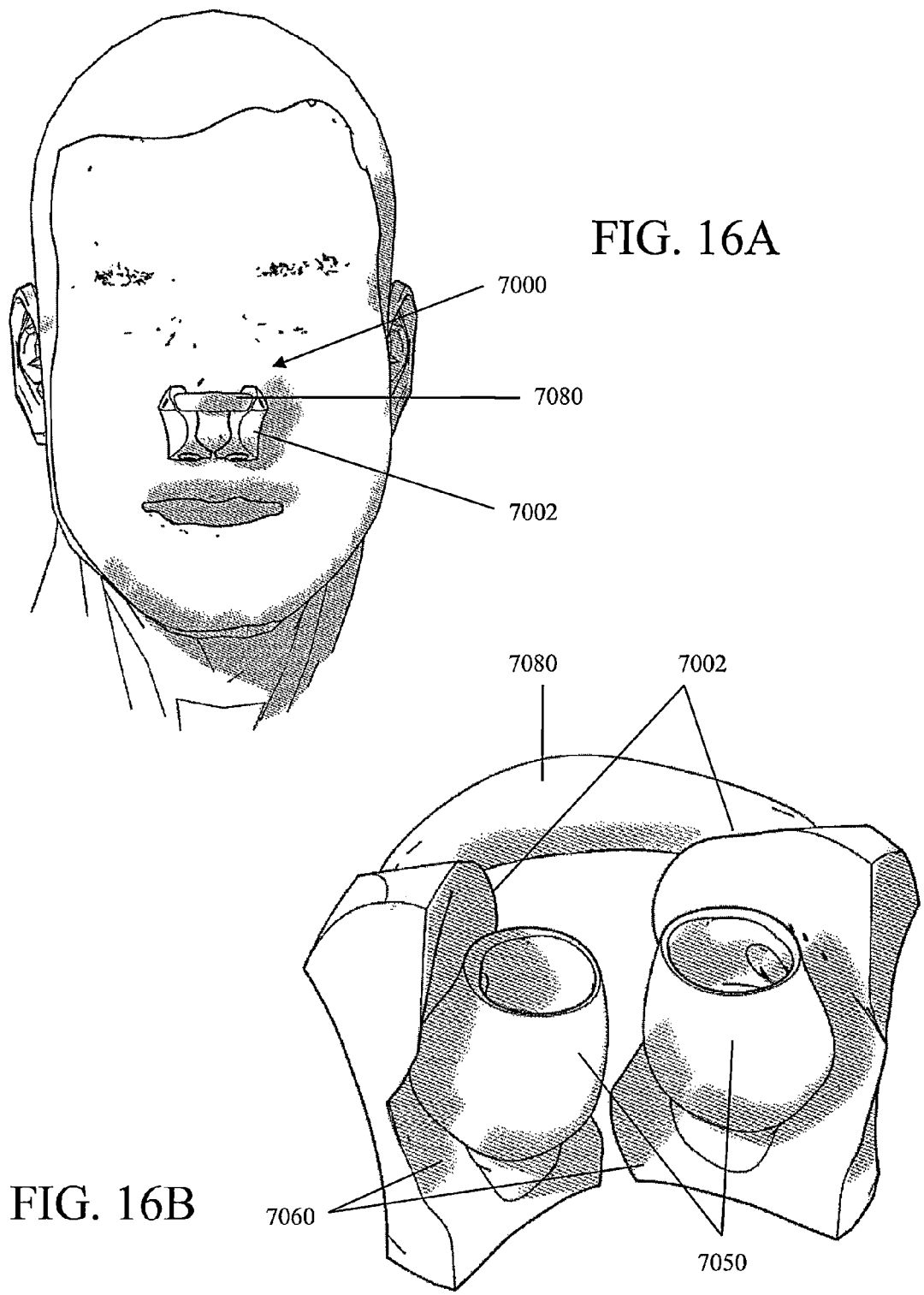
FIG. 16A is a front side view of a sleep apnea mask, in accordance with a seventh embodiment of the present invention.
FIG. 16B is a back side perspective view of a sleep apnea mask, in accordance with a seventh embodiment of the present invention.
Figure 16C:
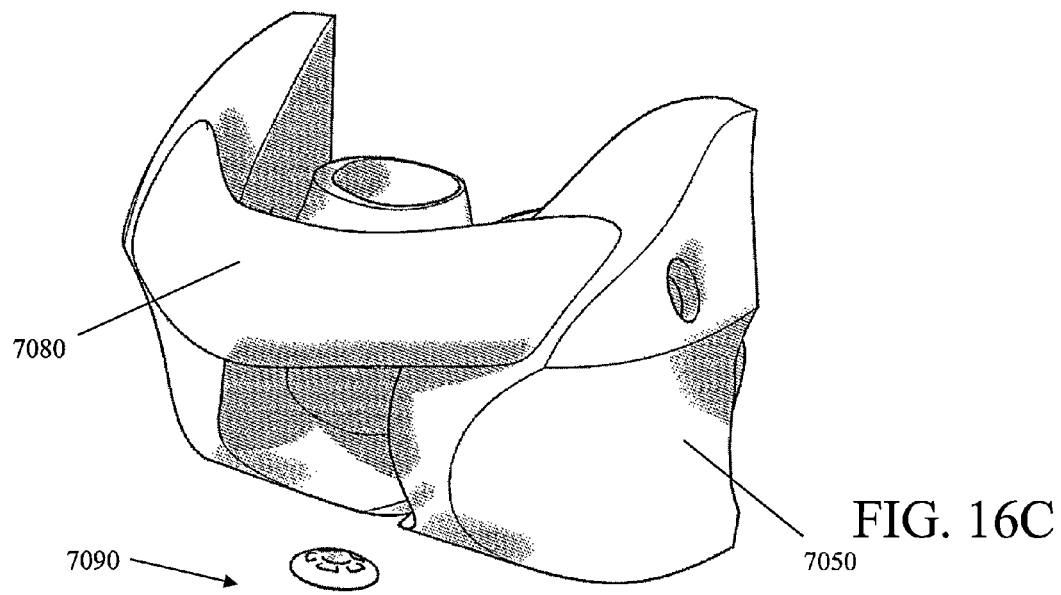
FIG. 16C is an exploded view of a sleep apnea mask, in accordance with a seventh embodiment of the present invention.
Figure 16D:
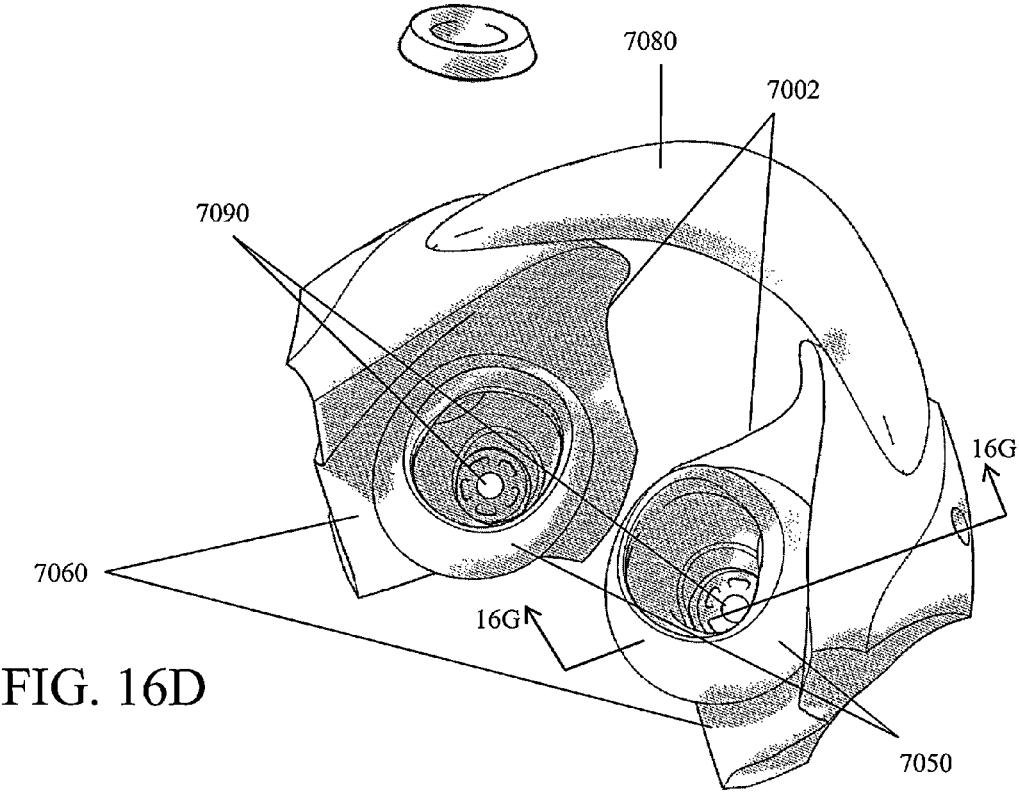
FIG. 16D is a top side perspective view of a sleep apnea mask, in accordance with a seventh embodiment of the present invention.
Figures 16E, 16F:
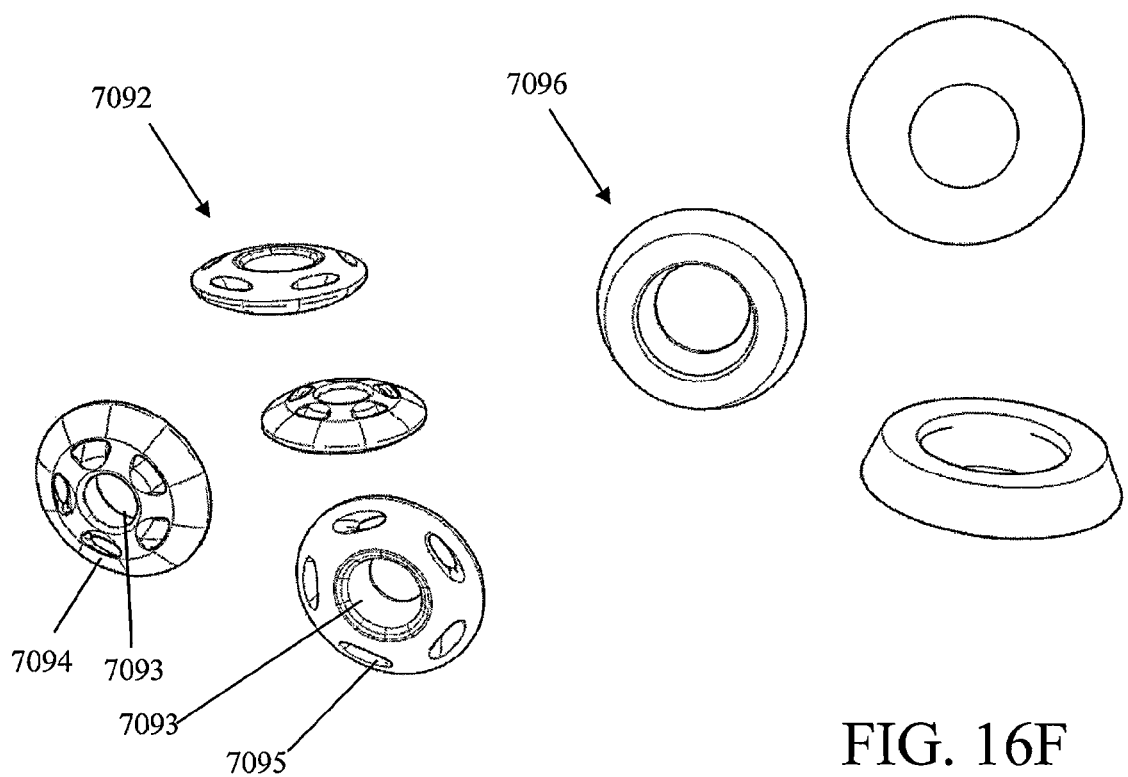
FIG. 16E are various views of a valve insert used in a sleep apnea mask, in accordance with a seventh embodiment of the present invention.
FIG. 16F are various views of a valve retainer used in a sleep apnea mask, in accordance with a seventh embodiment of the present invention.
Figure 16G:
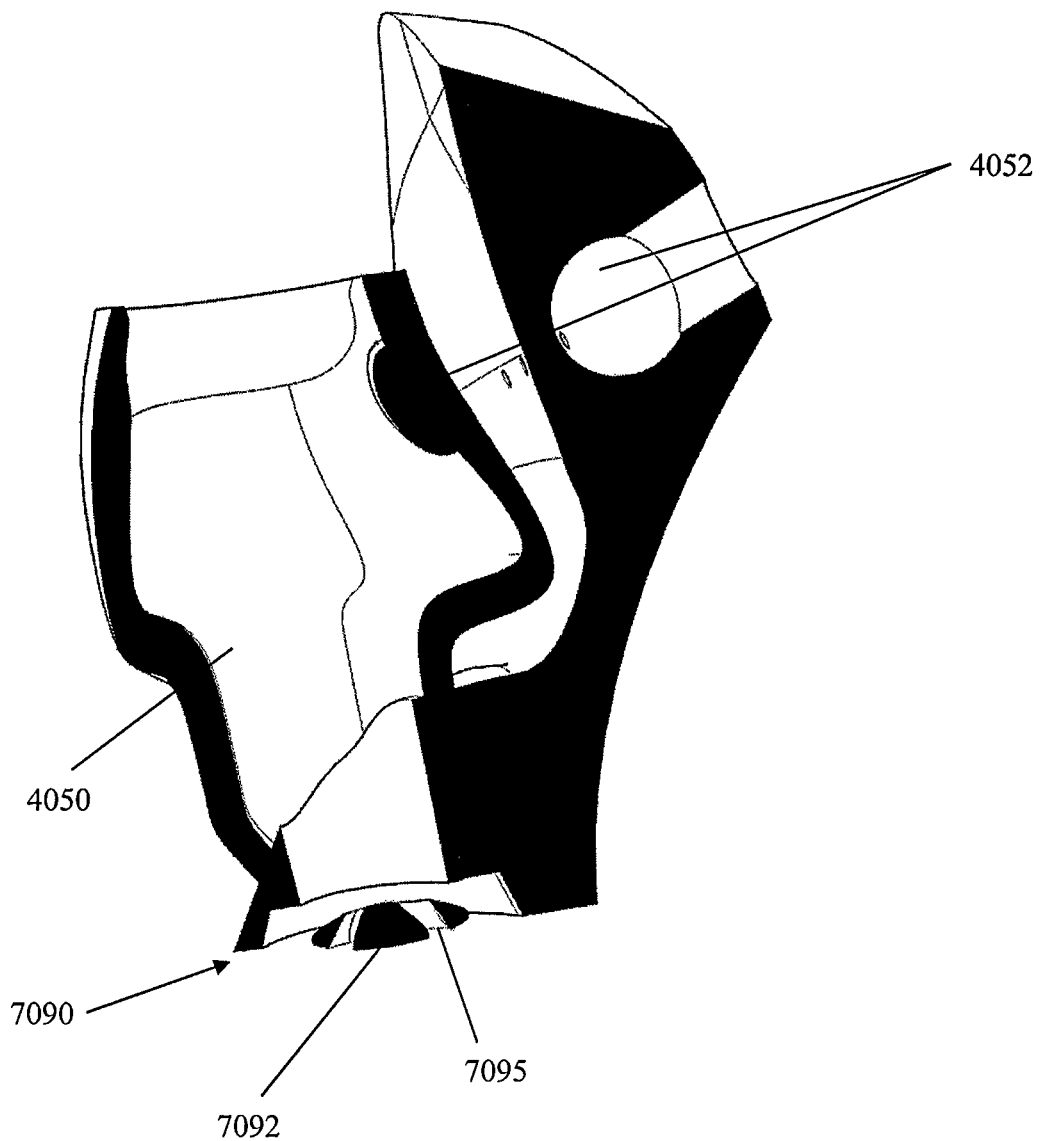
FIG. 16G is a cross sectional view of a nasal tube used in a sleep apnea mask, in accordance with a seventh embodiment of the present invention.

Referring to the cross section in FIG. 16G, one or more sleep apnea masks discussed above include a plurality of magnets 4052 configured to apply a biasing force to hold the mask in place. For example, magnets may be embedded in cavities in the nasal tubes 4050 and cavities in the mask in proximity to one another. The magnets are oriented so as to flex the nasal tubes toward the face mask which provides a gentle pinching force about the nose. The pinching force helps to secure the mask on the patient's face in addition to or instead of a headband. In addition to magnets, the gap between the nasal tubes and/or face mask may be adjusted to enhance the friction fit of the mask the patient's face.

In each of the seven embodiments above, the sleep apnea device directly contacts the patient's face. To enhance the seal, one or more embodiments may employ a pattern embossed on the inner side of the mask and/or headband where it contacts the user. The pattern may be designed to enhance the pressure seal between the mask and face or increase the friction fit of the mask to the face. The pattern may include parallel lines, hashing, or array of dots, for example.

Illustrated in FIGS. 17A-17B are perspective views of a pliable CPAP coupling used in some embodiments of the sleep apnea mask. The coupling 8000 includes a housing 8010 and an input port 8014 configured to connect to a CPAP machine output tube. The coupling is designed to detachably attach to the CPAP machine using a friction fit. When inserted into the recess 8012 of the coupling, the output of the CPAP machine is squeezed by the outer wall

8010 and inner wall of the input port 8014 to hold the CPAP output in place while the user sleeps. The coupling also includes a plurality of output ports 8020 configured to receive tubes, preferably polycarbonate tubing, that connects the coupling to the input of the air duct on the sleep apnea mask. The inner diameter and wall thickness of the output ports are configured to securely hold the polycarbonate tubing to avoid inadvertent detachment during use of the mask.

Figure 17D:
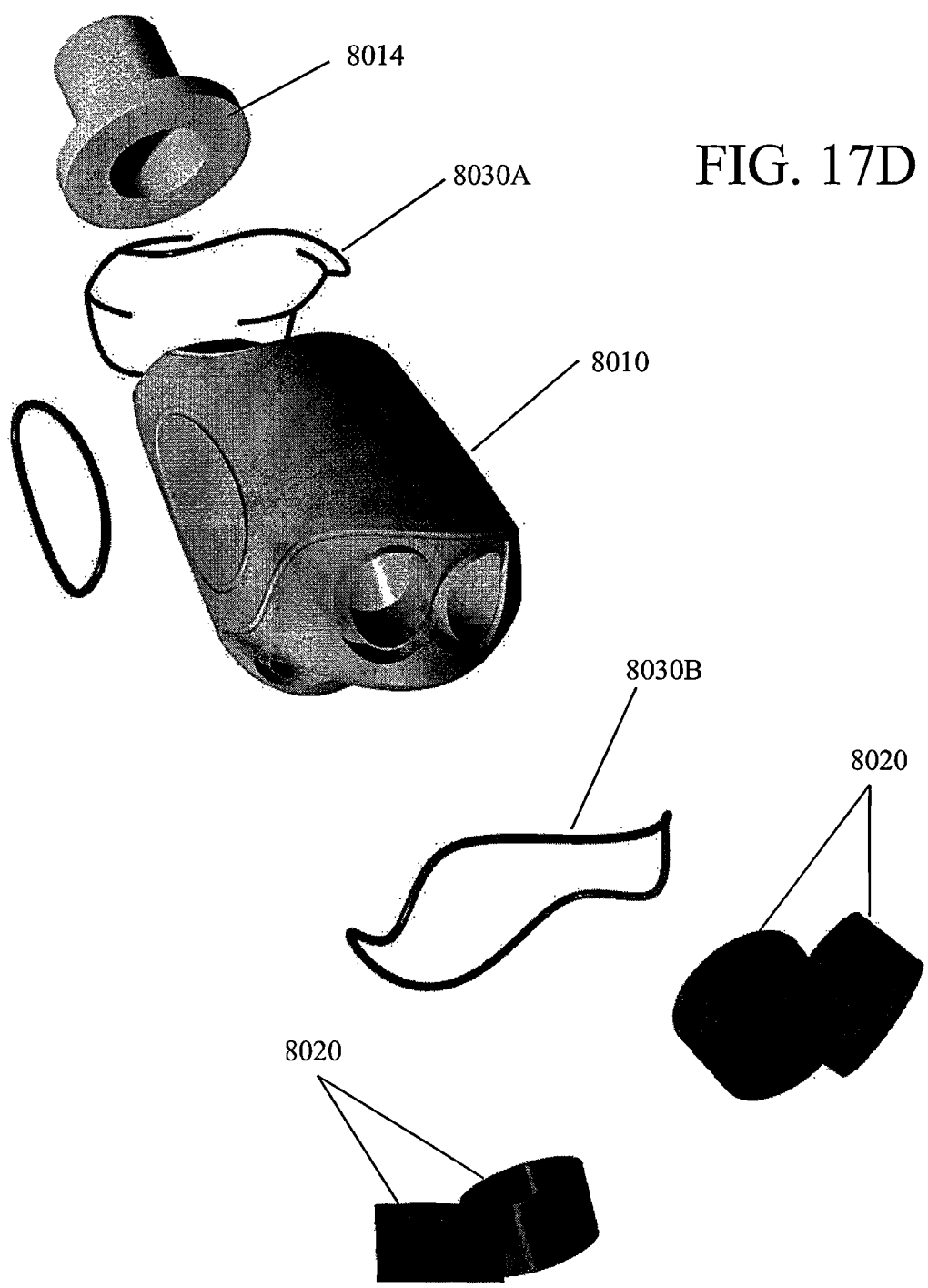
FIG. 17D is an exploded view of a CPAP coupling, in accordance with an embodiment of the present invention.

Illustrated in FIG. 17D is an exploded view of the CPAP coupling showing the various components including external webbing 8030A, 8030B used to maintain the structural integrity of the coupling. The webbing may be constructed from a relatively high tensile strength thermoset material. In the preferred embodiment, the entire CPAP coupling is constructed from highly elastic materials, primarily silicones. This provides for a pleasant user experience when touched by the patient, leaned on by the patient, or rolled against by the patient.

Figure 18:
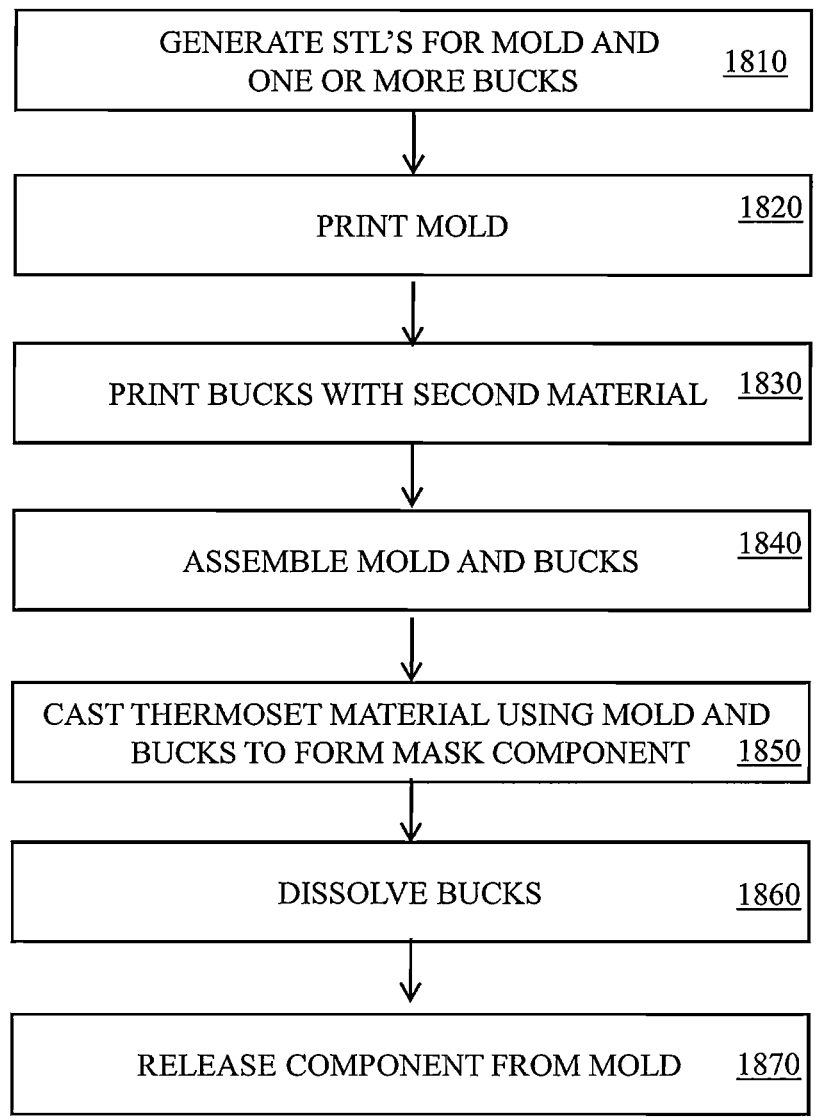
FIG. 18 is a flowchart of a method of a method of manufacturing a medical device or article of apparel, in accordance with a first embodiment.

Some of the sleep apnea devices and/or face mask above are produced directly using one or more layer-wise construction methods described above. In other embodiments, the sleep apnea devise and masks are produced using an investment molding technique illustrated in FIG. 18. In this embodiment, one or more ".STL" files are generated 1810, the set of ".STL" files defining the size and shape of molds and bucks from which mask components are cast. The molds are then 3D printed 1820 from any of a number of materials while the bucks are 3D printed 1830 from a second material that is capable of being dissolved by a first solvent. The mold and bucks are assembled 1840 and the mask component cast 1850. The casting material from which the component is made, preferably a thermoset material, is resistant to the first solvent. Thereafter, solvent is used to dissolve 1860 the bucks and release 1870 the mask. In some embodiments, the mold is made of a soluble material that is the same or different that the material from which the bucks are made. In addition, the component may subsequently be washed to remove all traces of solvent before the mask is used by the patient.

Figure 19:
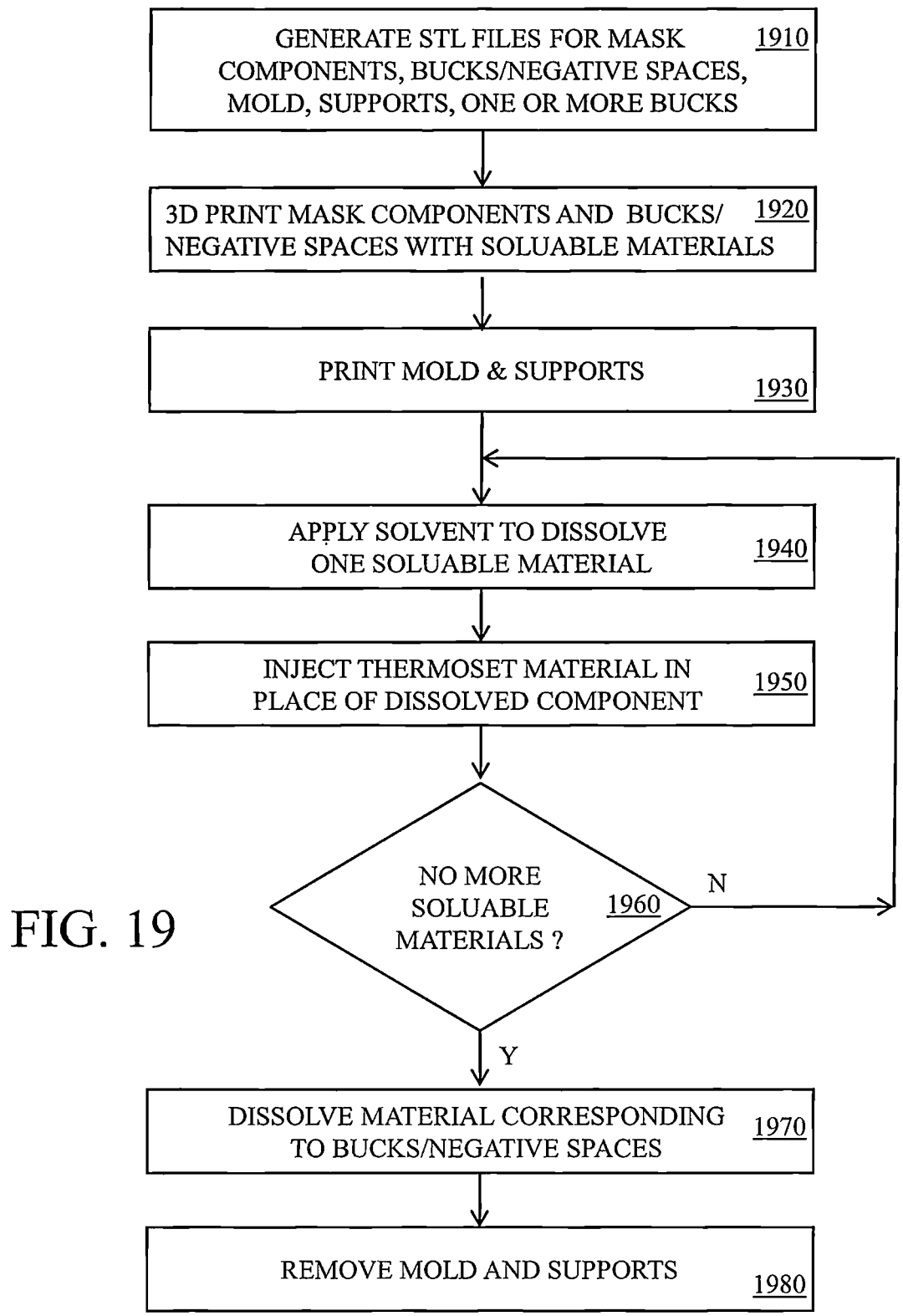
FIG. 19 is a flowchart of a method of a method of manufacturing a medical device or article of apparel, in accordance with a second embodiment.

Illustrated in FIG. 19 is a flowchart of a second embodiment of an investment molding technique. After the mask model has been determined using the DPDS 130 described above, the fabrication controller 136 generates 1910 ".STL" files defining the shape of one or mask components, negative spaces corresponding to air ducts, a mold if applicable, support structures if applicable, and one or more bucks if applicable. The mask components generally include a plurality of separate components corresponding to individual pieces, layers, or structures in the final mask. Thereafter, the ".STL" files for the mask components and negative spaces are concurrently 3D printed 1920 using one or more soluble materials. The negative spaces are generated as a solid structure using a soluble material that is later removed. The ".STL" files for the molds, supports, and bucks are printed 1930 either concurrently with the mask components or printed separately and assembled later. Once the components, negative mold, supports, and bucks are assembled, a first solvent is applied 1940 in order to remove one of the multiple mask components. When the solvent is removed, a new void is created. A thermoset material is then injected 1950 into this new void and the thermoset material allowed to cure in place. If there are additional soluble materials representing mask components remaining, decision block 1960 is answered in the negative. The next soluble material is dissolved and next thermoset material injected. The process is repeated until all mask components are produced.

Thereafter, the material corresponding to the negative space is dissolved 1970 using an additional solvent. As one skilled in the art will appreciate, thermoset structures must be resistant to any solvents that are applied subsequent to curing in order to prevent those thermoset materials from being removed unintentionally. If a mold or support structure was used, those materials may be separated 1980 from the remaining mask components. At this point, the resulting sleep apnea mask may be constructed from multiple materials that are completely bonded together, and the mask may contain one or more internal negative spaces.

In the preferred embodiment, combinations of soluble material/solvent include:
(1) PVA (Polyvinyl Alcohol)/water;
(2) HIPS (High Impact Polystyrene)/Lemonine or Terpene (citric acid);
(3) PLA (polylactic acid)||Sodium Hydroxide (caustic soda)
(4) ABS (acrylonitrile butadiene styrene)/Acetone;
(5) Nylon/Acetic Acid;
(6) Polycarbonate/Dichloromethane; and
(7) Glucose or glucose gelatin/enzymes.

Figure 20B:
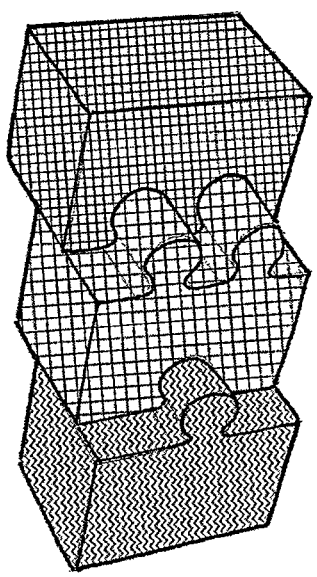
Figure 20A:
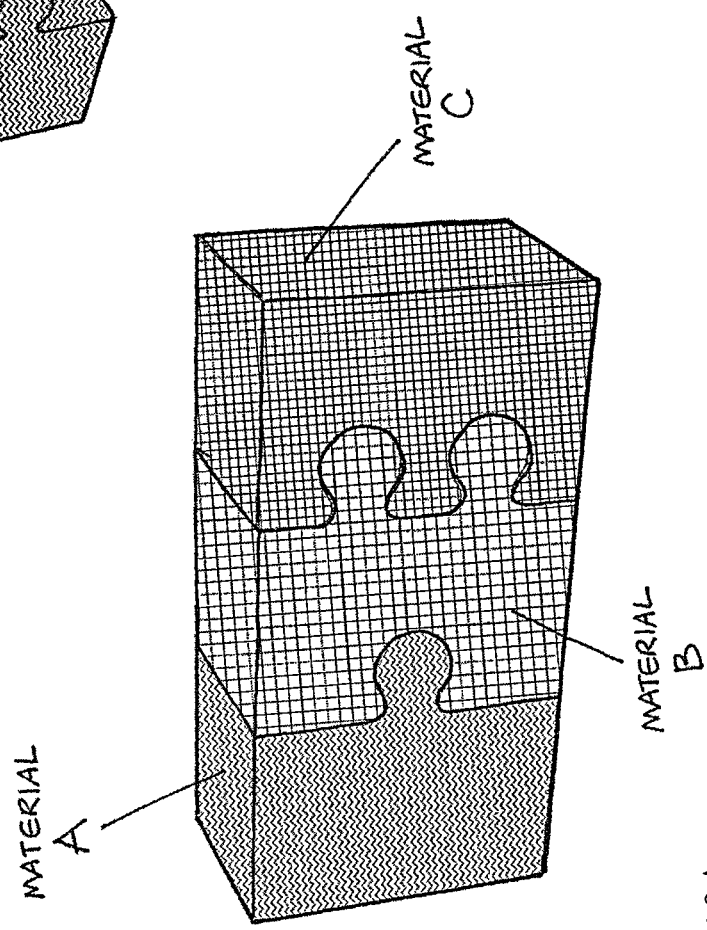

Illustrated in FIGS. 20A through 20L is a diagrammatic illustration of the 3D printing investment casting technique of the preferred embodiment. In brief, the final object is constructed by generating a set of temporary structures called "patterns" that are then sequentially removed and replaced using solvents and thermoset materials. FIG. 20A shows the final object after completion of the printing and casting. FIG. 20B shows a partial exploded view of the casting where the three materials that make up the casting are separated out to show the dimensionality of the component parts.

Figure 20E:
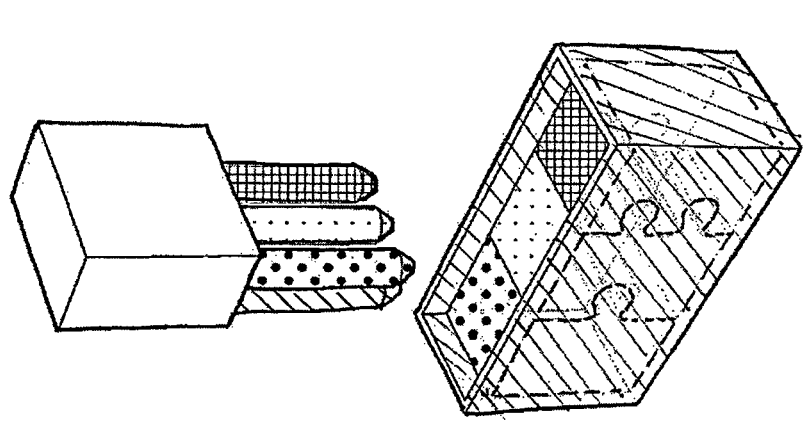
Figure 20D:
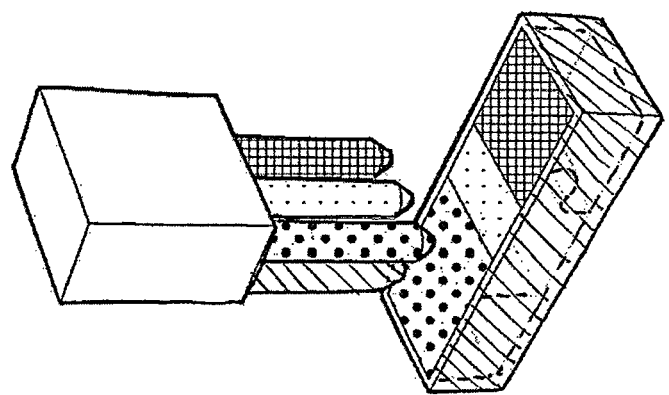
Figure 20C:
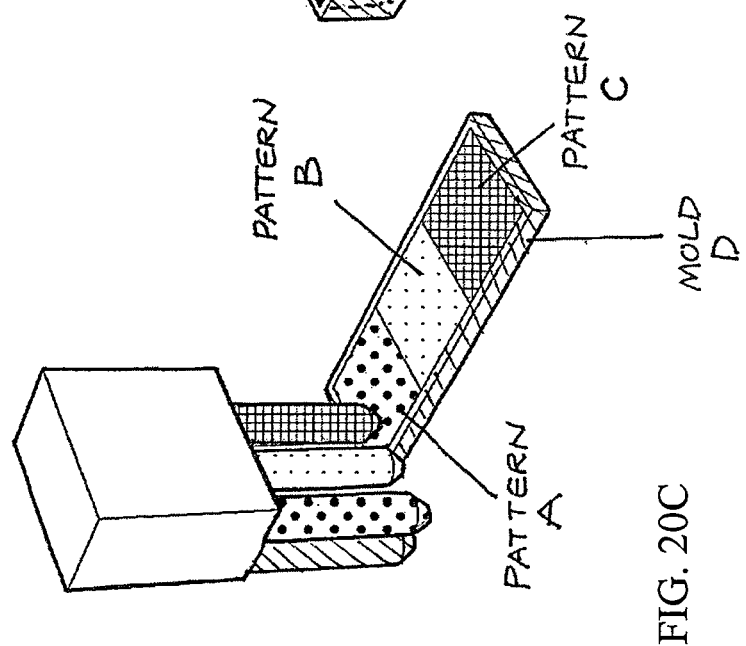
Figure 20F:
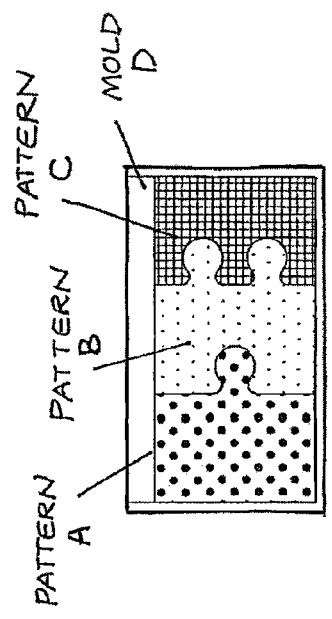

In accordance with the preferred embodiment, a multi-nozzle FDM machine, for example, is employed to generate three separate patterns by depositing three separate materials referred to here as "pattern A," "pattern B," and "pattern C" shown in FIGS. 20C-20E. Each of the three patterns represents a component of the final object. As shown, multiple nozzles are used to deposit the three separate pattern materials and generate the object in a layer-wise manner. The temporary object made of pattern materials is shown in FIG. 20F. The completed object resides in a mold, referred to herein as "mold D."

Figure 20G:
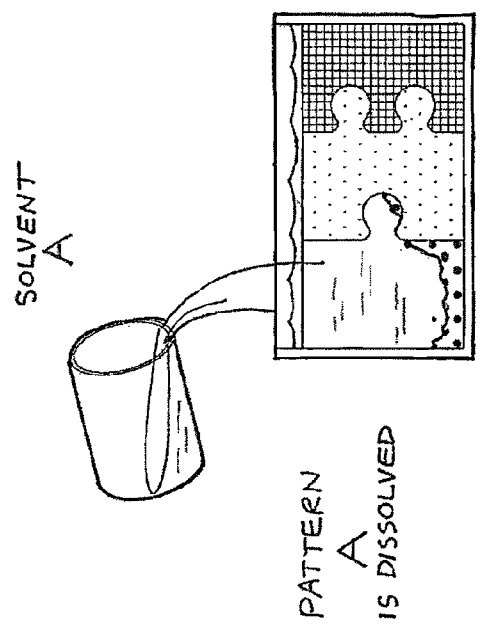
Figure 20H:
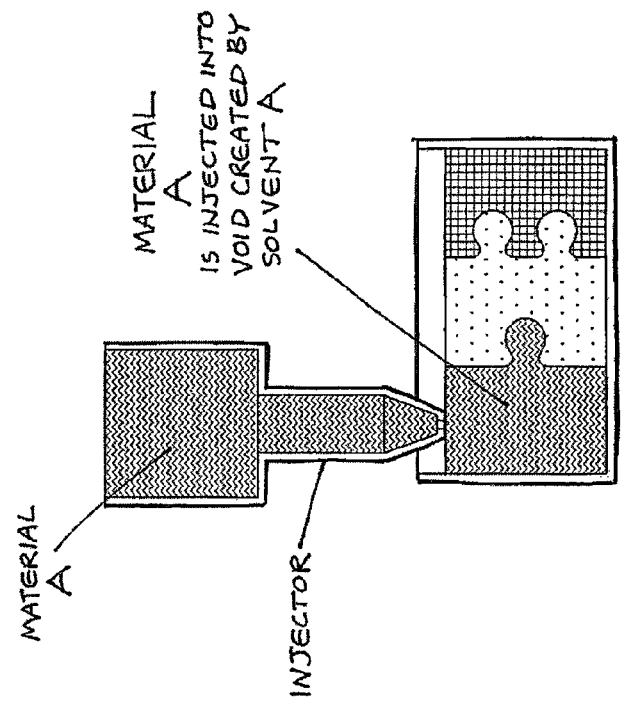

Referring to FIG. 20G, after the patterns are fully printed, a first solvent referred to as "solvent A" is used to dissolve pattern A. Referring to FIG. 20H, once the solvent is removed and the part cleaned, a nozzle injects "material A" into the negative space previously occupied by pattern A. As one skilled in the art will appreciate, pattern B and pattern C must be resistant to the solvent A.

Referring to FIG. 20I, a second solvent referred to as "solvent B" is then used to dissolve pattern B after material A has cured. Referring to FIG. 20J, once solvent B is removed and the part cleaned, a nozzle injects "material B" into the negative space previously occupied by pattern B. Material A and pattern C must be resistant to the solvent B.

Referring to FIG. 20K, a third solvent referred to as "solvent C" is then used to dissolve pattern C after material B has cured. Referring to FIG. 20L, once solvent C is removed and the part cleaned, a nozzle injects "material C" into the negative space previously occupied by pattern C. Material A and material B must be resistant to the solvent C. After material C has cured, the completed object may be released from the mold.

In the preferred embodiment, materials A, B, and C are thermoset materials, preferably a combination of hard and soft silicone thermoset materials. However, one skilled in the art will appreciate that a wide range of alternative materials may be employed and 3D printing techniques employed to produce the investment casting technique of the present invention.

Figures 21F, 21G:
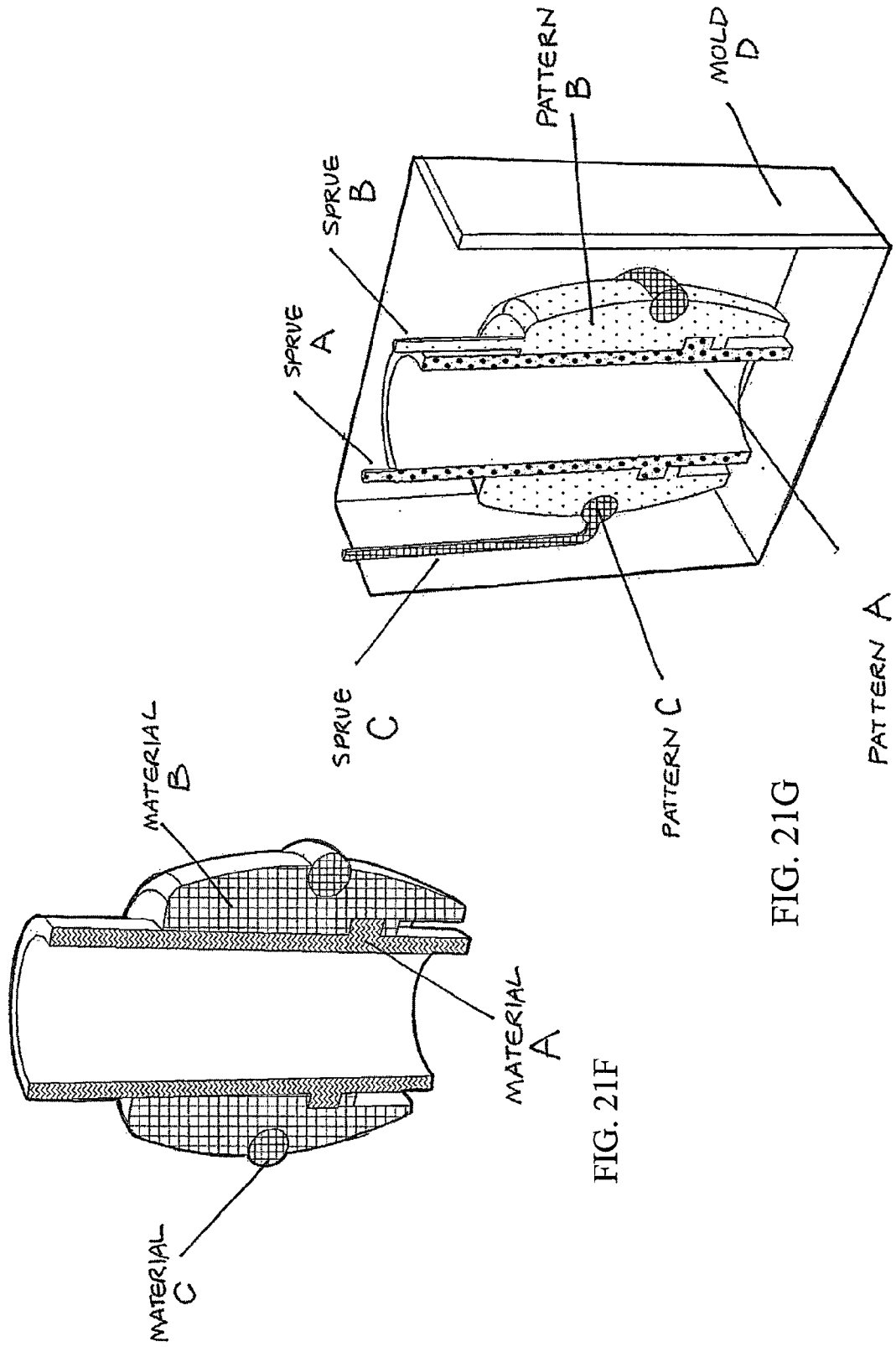
Figure 22B:
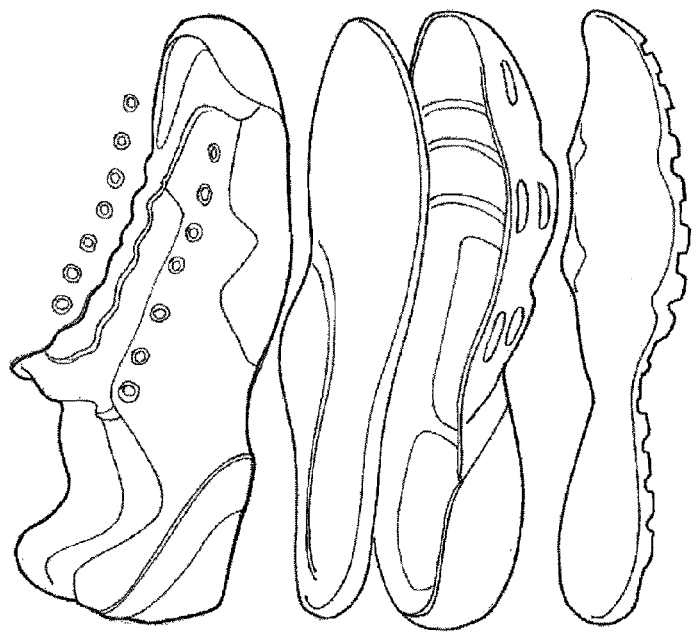
Figure 22A:
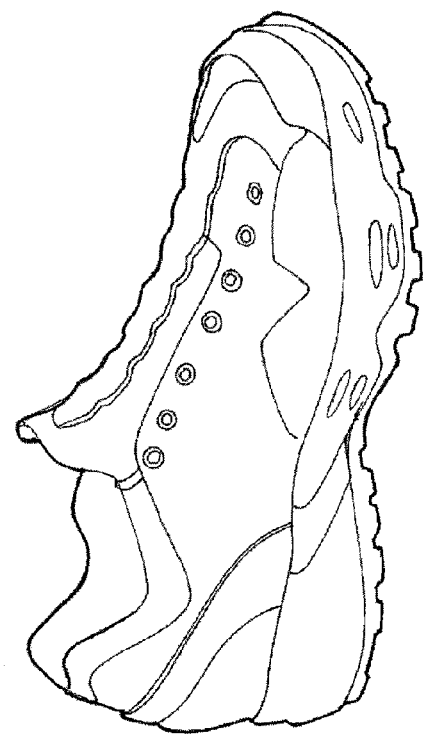

Illustrated in FIGS. 21A through 21M is a sequence of diagrammatic illustration showing the 3D printing investment casting technique used to make a CPAP coupling. The final coupling shown in FIG. 21B is shown in cross section in FIG. 21A. In this embodiment, the coupling is constructed from three silicone thermoset materials corresponding to three pattern materials—pattern A, pattern B, and pattern C. The three pattern materials are concurrently deposited in a layer-wise fashion using a FDM printing process shown in FIGS. 21C through 21E. A fourth material may be concurrently deposited to produce a mold around the patterns, referred to as mold D. The object constructed from pattern material is shown in perspective in FIG. 21F and cross section in FIG. 21G.

Referring to FIG. 21H, after the patterns are fully printed, a "solvent A" is used to dissolve pattern A. Referring to FIG. 21I, once the solvent is removed and the part cleaned, a nozzle pours or injects "material A" into the negative space previously occupied by pattern A. As one skilled in the art will appreciate, pattern B and pattern C are resistant to the solvent A. As shown, one or more sprues and gates may be used to inject the material and evacuate air, as needed.

Referring to FIG. 21J, "solvent B" is then used to dissolve pattern B after material A has cured. Referring to FIG. 21K, once solvent B is removed and the part cleaned, a nozzle injects "material B" into the negative space previously occupied by pattern B. Material A and pattern C are resistant to the solvent B.

Referring to FIG. 21L, "solvent C" is then used to dissolve pattern C after material B has cured. Referring to FIG. 21M, once solvent C is removed and the part cleaned, a nozzle injects "material C" into the negative space previously occupied by pattern C. Material A and material B must be resistant to the solvent C. After material C has cured, the completed object may be released from the mold and the remnants of the sprues and gates removed. The complete coupling may then be employed with a face mask produced using the same technique described above, for example.

Illustrated in FIGS. 22A through 22G is a diagrammatic illustration of the investment casting technique used to make a running shoe. The completed running shoe is shown in perspective FIG. 22A and in exploded view in FIG. 22B. FIG. 22C-FIG. 22G show each of five different materials being injected into the mold during assembly. Material A is injected to form the tread of the shoe in FIG. 22C, material B injected to form the sole of the shoe in FIG. 22D, material C injected to form the shoe "upper" in FIG. 22E, material D injected to form the insole of the shoe FIG. 11F, and material E injected to form the eyelets in FIG. 22G. Although not shown, each injection step is preceded by a step of dissolving a pattern, as shown in the figures above. After the final injection step, the completed shoe is removed from the mold and the sprues and gates remove. As one skilled in the art will appreciate, the investment casting technique described above can be employed to make shoes having a structure and composition that prior art techniques cannot produce do to limitations in materials and casting techniques.

The five materials correspond to the shoe tread, sole, padding, upper, and lace grommets. In the preferred embodiment, the first four materials injected are thermoset materials while the last material is nylon or other hard plastic.

Systems and user interfaces of the present invention may be implemented with one or more non-transitory computer readable media, wherein each medium may be configured to include thereon data or computer executable instructions for manipulating data. The computer executable instructions include data structures, objects, programs, routines, or other program modules that may be accessed by a processing system, such as one associated with a general-purpose computer or processor capable of performing various different functions or one associated with a special-purpose computer capable of performing a limited number of functions. Computer executable instructions cause the processing system to perform a particular function or group of functions and are examples of program code means for implementing steps for methods disclosed herein. Furthermore, a particular sequence of the executable instructions provides an example of corresponding acts that may be used to implement such steps. Examples of computer readable media include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing system. Examples of mass storage devices incorporating computer readable media include hard disk drives, magnetic disk drives, tape drives, optical disk drives, and solid state memory chips, for example. The term processor as used herein refers to a number of processing devices including personal computing devices, servers, general purpose computers, special purpose computers, application-specific integrated circuit (ASIC), and digital/analog circuits with discrete components, for example.

As one skilled in the art will appreciate, the various dimensions of a mask generally vary from person to person because those features are dictated by the size and locations of the features on each patient's face.

Therefore, the invention has been disclosed by way of example and not limitation, and reference should be made to the following claims to determine the scope of the present invention.

We claim:

1. A method of making a custom sleep apnea mask configured to operate with a CPAP machine, the method comprising:
    scanning at least a portion of a user's face;
    generating a surface model of the user's face;
    identifying a set of facial features from the surface model, the set comprising:
        a) a first point corresponding to the user's nose, and
        b) a second point corresponding to the user's lips;
    generating a first linear contour on the surface model based on the first point;
    generating a second linear contour on the surface model based on the second point;
    generating a third linear contour interposed between the first and second linear contours, wherein the third linear contour extends beyond the first point a determined offset;
    generating an outer surface of the mask, wherein the outer surface comprises the first, second, and third linear contours; and
    generating an inner surface of the mask, wherein the inner surface comprises at least a portion of the surface model between the first and second linear contours.

2. The method of claim 1, wherein the method further comprises:
   providing a surface model of a head;
   combining the surface model of the user's face with the surface model of the head; and
   wherein the generating of the inner surface of the mask is based on the combination of the surface model of the user's face with the surface model of the head.

3. The method of claim 1, wherein generating the third contour comprises:
   averaging the first contour and the second contour;
   adding a lateral offset in a direction away from the surface model of the user's face; and
   low-pass filtering.

4. The method of claim 1, further comprising:
   generating a surface model of nasal tubes;
   orientating the surface model of the nasal tubes based on at least the first point; and
   combining the surface model of the nasal tubes with the inner surface of the mask.

5. The method of claim 1, wherein the identifying of a set of facial features from the surface model comprises:
   identifying a tip of the nose, a bridge of the nose between eyes, an upper-most point of a set of lips, an underside of the nose, a width of the face, and center points of two nostrils.

* * * * *

UNITED STATES PATENT AND TRADEMARK OFFICE
CERTIFICATE OF CORRECTION

PATENT NO.         : 9,498,593 B2  
APPLICATION NO.    : 14/102370  
DATED              : November 22, 2016  
INVENTOR(S)        : Leslie Oliver Karpas et al.

It is certified that error appears in the above-identified patent and that said Letters Patent is hereby corrected as shown below:

In the Claims

Column 20, Line 60, after "the first point" add --by--.

Signed and Sealed this
Fourth Day of July, 2017

Joseph Matal
*Performing the Functions and Duties of the*
*Under Secretary of Commerce for Intellectual Property and*
*Director of the United States Patent and Trademark Office*